United States Patent
Sugiyama

(10) Patent No.: US 10,124,046 B2
(45) Date of Patent: Nov. 13, 2018

(54) HLA-DR-BINDING ANTIGEN PEPTIDE DERIVED FROM WT1

(71) Applicant: International Institute of Cancer Immunology, Inc., Osaka (JP)

(72) Inventor: Haruo Sugiyama, Minoo (JP)

(73) Assignee: International Institute of Cancer Immunology, Inc., Osaka (JP)

( * ) Notice: Subject to any disclaimer, the term of this patent is extended or adjusted under 35 U.S.C. 154(b) by 0 days.

(21) Appl. No.: 13/755,185

(22) Filed: Jan. 31, 2013

(65) Prior Publication Data

US 2013/0243800 A1 Sep. 19, 2013

Related U.S. Application Data

(62) Division of application No. 10/578,183, filed as application No. PCT/JP2004/016336 on Nov. 4, 2004.

(30) Foreign Application Priority Data

Nov. 5, 2003 (JP) .................................. 2003-375603

(51) Int. Cl.
*A61K 39/00* (2006.01)
*C07K 14/47* (2006.01)
*A61K 38/00* (2006.01)

(52) U.S. Cl.
CPC ...... *A61K 39/0011* (2013.01); *C07K 14/4748* (2013.01); *A61K 38/00* (2013.01)

(58) Field of Classification Search
CPC .................. C07K 14/4748; A61K 38/1764
See application file for complete search history.

(56) References Cited

U.S. PATENT DOCUMENTS

| | | | |
|---|---|---|---|
| 7,030,212 | B1 | 4/2006 | Sugiyama et al. |
| 7,063,854 | B1 | 6/2006 | Gaiger et al. |
| 7,342,092 | B2 | 3/2008 | Sugiyama |
| 7,378,384 | B2 | 5/2008 | Sugiyama et al. |
| 7,390,871 | B2 | 6/2008 | Sugiyama et al. |
| 7,420,034 | B2 | 9/2008 | Sugiyama et al. |
| 7,517,950 | B2 | 4/2009 | Sugiyama et al. |
| 7,608,685 | B1 | 10/2009 | Sugiyama et al. |
| 7,622,119 | B2 | 11/2009 | Sugiyama |
| 7,666,985 | B2 | 2/2010 | Sugiyama et al. |
| 7,939,627 | B2 | 5/2011 | Nishihara et al. |
| 8,105,604 | B2 | 1/2012 | Sugiyama |
| 8,388,975 | B2 | 3/2013 | Sugiyama |
| 8,765,687 | B2 | 7/2014 | Scheinberg et al. |
| 9,233,149 | B2 | 1/2016 | Scheinberg et al. |
| 2002/0128196 | A1 | 9/2002 | Call et al. |
| 2004/0097703 | A1 | 5/2004 | Sugiyama |
| 2004/0247609 | A1 | 12/2004 | Sugiyama |
| 2005/0002951 | A1 | 6/2005 | Sugiyama et al. |
| 2006/0121046 | A1 | 6/2006 | Gaiger et al. |
| 2006/0217297 | A1 | 9/2006 | Sugiyama et al. |
| 2007/0082860 | A1 | 4/2007 | Sugiyama et al. |
| 2007/0128207 | A1 | 6/2007 | Sugiyama |
| 2008/0070835 | A1 | 3/2008 | Sugiyama |
| 2008/0152631 | A1 | 6/2008 | Sugiyama |
| 2009/0099090 | A1 | 4/2009 | Sugiyama et al. |
| 2009/0143291 | A1 | 6/2009 | Sugiyama et al. |
| 2009/0263409 | A1 | 10/2009 | Sugiyama |
| 2009/0231043 | A1 | 11/2009 | Sugiyama |
| 2009/0281043 | A1 | 11/2009 | Sugiyama |
| 2010/0062013 | A1 | 3/2010 | Sugiyama |
| 2010/0092522 | A1 | 4/2010 | Scheinberg et al. |
| 2010/0190163 | A1 | 7/2010 | Sugiyama |
| 2010/0247556 | A1 | 9/2010 | Sugiyama |
| 2010/0292160 | A1 | 11/2010 | Sugiyama |
| 2011/0098233 | A1 | 4/2011 | Sugiyama |
| 2012/0045465 | A1 | 2/2012 | Sugiyama |
| 2012/0195918 | A1 | 8/2012 | Sugiyama |
| 2013/0196427 | A1 | 8/2013 | Sugiyama |
| 2013/0266958 | A1 | 10/2013 | Sugiyama et al. |
| 2015/0328278 | A1 | 11/2015 | Kubo et al. |

FOREIGN PATENT DOCUMENTS

| | | |
|---|---|---|
| CN | 1902313 A | 1/2007 |
| EP | 1 696 027 | 8/2006 |
| EP | 1 696 027 A1 | 8/2006 |
| EP | 2 098 595 | 9/2009 |
| EP | 2 098 595 A1 | 9/2009 |
| JP | 2002 525099 | 8/2002 |
| JP | 2002 525099 A | 8/2002 |

(Continued)

OTHER PUBLICATIONS

Healthline.com, "Non-hodgkin's Lymphoma: In Depth-Overview", pp. 1-3, http://www.healthline.com/channel/non-hodgkins-lymphoma_indepth-overview, retrieved Dec. 2, 2008.*

Knights et al., "Prediction of an HLA-DR-Binding Peptide Derived From Wilms' Tumour 1 Protein and Demonstration of In Vitro Immunogenicity of WT1 (124-138)-Pulsed Dendritic Cells Generated According to an Optimised Protocol", Cancer Immunol Immunother, vol. 51, pp. 271-281, 2002.

Sotiriadou et al., "Peptide HER2(776-788) Represents a Naturally Processed Broad MHC Class II-Restricted Cell Epitope", British Journal of Cancer, vol. 85, No. 10, pp. 1527-1534, 2001.

Hural et al., "Identification of Naturally Processed CD4 T Cell Epitopes From the Prostate-Specific Antigen Kallikrein 4 Using Peptide-Based In Vitro Stimulation", The Journal of Immunology, vol. 169, pp. 557-565, 2002.

(Continued)

*Primary Examiner* — Zachary S Skelding
(74) *Attorney, Agent, or Firm* — Oblon, McClelland, Maier & Neustadt, L.L.P.

(57) ABSTRACT

The present invention provides a method of treating or preventing cancer, by administering a peptide consisting of 16-25 contiguous amino acids in the amino acid sequence of human WT1 of SEQ ID NO: 1, which has the amino acid sequence of SEQ ID NO: 24, an expression vector having a polynucleotide encoding said peptide or a cell containing the expression vector to a subject in need thereof.

26 Claims, 27 Drawing Sheets

Specification includes a Sequence Listing.

(56) References Cited

FOREIGN PATENT DOCUMENTS

| | | |
|---|---|---|
| JP | 2006-280324 | 10/2006 |
| JP | 2006-280324 A | 10/2006 |
| WO | WO 00/18795 A2 | 4/2000 |
| WO | 01/62920 A2 | 8/2001 |
| WO | 01/62920 A3 | 8/2001 |
| WO | WO 01/62920 A2 | 8/2001 |
| WO | WO 02/099084 A2 | 12/2002 |
| WO | 03/002142 A1 | 1/2003 |
| WO | WO 03/002142 A1 | 1/2003 |
| WO | 03/028758 A1 | 4/2003 |
| WO | WO 03/028758 A1 | 4/2003 |
| WO | WO 03/106682 | 12/2003 |
| WO | WO 03/106682 A1 | 12/2003 |
| WO | WO 2005/045027 | 5/2005 |
| WO | WO 2005/045027 A1 | 5/2005 |
| WO | WO 2005/095598 | 10/2005 |
| WO | WO 2005/095598 A1 | 10/2005 |
| WO | WO 2007/097358 | 8/2007 |
| WO | WO 2007/097358 A1 | 8/2007 |
| WO | WO 2008/081701 | 7/2008 |
| WO | WO 2008/081701 A1 | 7/2008 |
| WO | WO 2008/105462 | 9/2008 |
| WO | WO 2008/105462 A1 | 9/2008 |
| WO | WO 2010/123065 | 10/2010 |
| WO | WO 2010/123065 A1 | 10/2010 |
| WO | WO 2012/046730 | 4/2012 |
| WO | WO 2012/046730 A1 | 4/2012 |

OTHER PUBLICATIONS

Glenn Y. Ishioka, et al., "Utilization of MHC Class I Transgenic Mice for Development of Minigene DNA Vaccines Encoding Multiple HLA-Restricted CTL Epitopes[1]", J. Immunol., vol. 162, 1999, pp. 3915-3925.
Craig L. Slingluff, Jr.,et al., "Phase I Trial of a Melanoma Vaccine with gp100 $_{280\text{-}288}$ Peptide and Tetanus Helper Peptide in Adjuvant: Immunologic and Clinical Outcomes[1]", Clinical Cancer Research, vol. 7, 2001, pp. 3012-3024.
Singh, et al., Bioinformatics Applications Note, "ProPred: prediction of HLA-DR binding sites", vol. 17, No. 12, 2001, pp. 1236-1237.
Rena J. May PhD., et al., "CD4+ Peptide Epitopes from the WT1 Oncoprotein Stimulate CD4+ and CD8+ T Cells That Recognize and Kill Leukemia and Solid Tumor Cells" Blood (ASH Annual Meeting Abstracts) 2006 108: Abstract 3706© 2006 American Society of Hematology, 1 pg.
Office Action dated Dec. 30, 2016, in co-pending U.S. Appl. No. 14/652,298.
Thomas Hoehler, et al., "HLA-DRB1*1301 and *1302 protect against chronic hepatitis B", vol. 26, pp. 503-507, Journal of Hepatology, 1997.
Del Rincôn, et al., "Ethnic Variation in the Clinical Manifestations of Rheumatoid Arthritis: Role of HLA-DRB1 Alleles," Arthritis & Rheumatism. vol. 49, No. 2, Apr. 15, 2003, pp. 200-208.
Nikbin, B., et al., "Human Leukocyte Antigen (HLA) Class I and II Polymorphism in Iranian Healthy Population from Yazd Province," Iran J Allergy Asthma Immunol, Feb. 2017, 16(1), pp. 1-13.
Marsh, S.G.E., et al., "Nomenclature for factors of the HLA system, 2004," Tissue Antigens, 2005. 65, pp. 301-369.
Yuhung Lin, et al., "HLA-DPB1*05:01-restricted WT1332-specific TCR-transduced CD4+ T Lymphocytes Display a Helper Activity for WT1-specific CTL Induction and a Cytotoxicity Against Leukemia Cells", J Immunother, vol. 36, No. 3, Apr. 2013, 159-170 www.immunotherapy-journal.com.
K. L. Knutson, et al., "Tumor antigen-specific T helper cells in cancer immunity and immunotherapy", Published online: Jan. 27, 2005, Cancer Immunol Immunother (2005) 54: 721-728.
Canadian Office Action dated Jan. 19, 2016 in Canadian patent application No. 2,544,214. Title: "HLA-DR-Binding Peptide Derived From WT1", 3 pp.
Canadian Office Action dated Mar. 12, 2014 in Canadian patent application No. 2,544,214. Title: "HLA-DR-Binding Peptide Derived From WT1", 2 pp.
Office Action dated Mar. 15, 2016, in corresponding Mexican Patent Application No. MX/a/2014/002596, filed Aug. 27, 2014 (with English translation).
Hearing Notice dated May 5, 2016 issued in Indian Patent Application No. 4956/CHENP/2009 corresponding to the related U.S. Appl. No. 12/449,765, filed Aug. 26, 2009.
Office Action dated May 25, 2016 issued in Mexican Patent Application No. MX/ A/20 13/003884 and English translation thereof.
Office Action dated May 31, 2016 issued in Chinese Patent Application No. 201410573477.9 and English translation thereof.
Extended European Search Report dated Jun. 6, 2016 issued in European Patent Application No. 13864968.6.
Office Action dated Jun. 2, 2016 issued in corresponding U.S. Appl. No. 13/877,768.
Restriction Requirement issued Aug. 9, 2016 in corr. U.S. Appl. No. 14/652,298, filed Jun. 15, 2015.
Office Action dated Sep. 6, 2016 [received by Applicant on Oct. 31, 2016] in corr. Colombian Patent Application No. 15162173, filed Jul. 14, 2015 (with English translation).
Office Action dated Dec. 5, 2016, issued in Eurasian Patent Application No. 201591168 (with its English translation), corresponding to U.S. Appl. No. 14/652,298.
Ludmil Müller et al., "Synthetic peptides derived from the Wilms' tumor 1 protein sensitize human T lymphocytes to recognize chronic myelogenous leukemia cells", The Hematology Journal, vol. 4, 2003, pp. 57-66 (with English translation).
Combined Chinese Office Action and Search Report dated Apr. 9, 2014 in Patent Application No. 201180058552.2 with English Translation.
Australian Patent Examination Report No. 1 dated Jun. 2, 2014 in Patent Application No. 2011313327.
Office Action dated Apr. 7, 2015 in Taiwanese Patent Application No. 100135857 (with English translation).
Oezdemir et al., "HLA-DRB1*0101 and *0405 As Protective Alleles in Japanese Patients With Renal Cell Carcinoma", Cancer Research, vol. 57, No. 4, pp. 742-746, 1997.
Friede et al., "Natural Ligand Motifs of Closely Related HLA-DR4 Molecules Predict Features of Rheumatoid Arthritis Associated Peptides", Biochimica Et Biophysica Acta, vol. 1316, No. 2, pp. 85-101, 1996.
Rammensee et al., "MHC Ligands and Peptide Motifs: First Listing", Immunogenetics, vol. 41, No. 4, pp. 178-228, 1995.
Call et al., "Isolation and Characterization of a Zinc Finger Polypeptide Gene at the Human Chromosome 11 Wilms' Tumor Locus", Cell Press, vol. 60, pp. 509-520, 1990.
Gessler et al., "Homozygous Deletion in Wilms Tumours of a Zinc-Finger Gene Identified by Chromosome Jumping", Letters to Nature, vol. 343, pp. 774-778, 1990.
Menke et al., "The Wilms' Tumor 1 Gene: Oncogene or Tumor Suppressor Gene?", International Review of Cytology, vol. 181, 151-212, 1998.
Sugiyama, "Cancer Immunotherapy Targeting WT1 Protein", International Journal of Hematology, vol. 76, pp. 127-132, 2002.
Gao et al., "Antigen-Specific CD4+ T-Cell Help Is Required to Activate a Memory CD8+ T Cell to a Fully Functional Tumor Killer Cell", Cancer Research, vol. 62, pp. 6438-6441, 2002.
Zeng, "MHC Class II-Restricted Tumor Antigens Recognized by CD4+ T Cells: New Strategies for Cancer Vaccine Design", Journal of Immunotherapy, vol. 24, No. 3, pp. 195-204, 2001.
Wymann et al., "Human B Cells Secrete Migration Inhibition Factor (MIF) and Present a Naturally Processed MIF Peptide on HLA-DRB1 *0405 by a FXXL Motif", Immunology, vol. 96, pp. 1-9, 1999.
Maffei et al., "Peptides Bound to Major Histocompatibility Complex Molecules", Peptides, vol. 19, No. 1, pp. 179-198, 1998.
May, Rena J. et al., "CD4+peptide epitopes from the WT1 oncoprotein stimulate CD4+ and CD8+T cells that recognize and kill leukemia and solid tumor cells", Blood, vol. 108, No. 11, Part 1, Nov. 2006 (Nov. 2006), p. 10S8A, XP009097422 & 48th Annual Meeting of

(56) References Cited

OTHER PUBLICATIONS the American-Society-of-Hematology; Orlando, FL, USA; Dec. 9-12, 2006, ISSN: 0006-4971, the whole document.
Feng Guang et al., "Antigen-specific CD4* T-Cell Help Is Required to Activate a Memory CD8* T Cell to a Fully Functional Tumor Killer Cell'," Cancel Research, 2002, vol. 62, pp. 6438-6441.
Database JPO Proteins [Online] Jul. 17, 2003, "Compositions and methods for WT1 specific immunotherapy", XP002473316.
Database JPO Proteins [Online] Jul. 17, 2003, "Cancer vaccine comprising cationic liposome and cancer antigen based on tumor suppressor gene WT1", XP002473130.
May, Rena J. et al., "CD4+peptide epitopes from the WT1 oncoprotein stimulate CD4+ and CD8+T cells that recognize and kill leukemia and solid tumor cells", Blood, vol. 108, No. 11, Part 1, Nov. 2006 (Nov. 2006), p. 1058A, XP009097422 & 48th Annual Meeting of the American-Society-of-Hematology; Orlando, FL, USA; Dec. 9-12, 2006, ISSN: 0006-4971, the whole document.
Jung-Hwan Kim, et al., "In Vitro Binding Analysis of Hepatitis B Virus PreS-derived Putative Helper T-cell Epitopes to MHC Class II Molecules Using Stable HLA-DRB1*0405/-DRA*0101 Transfected Cells", IUBMB Life, 50 (6), 2000, pp. 379-384.
Glenn Y. Ishioka, et al., "Utilization of MHC Class I Transgenic Mice for Development of Minigene DNA Vaccines Encoding Multiple HLA-Restricted CTL Epitopes1", J. Immunol., vol. 162, 1999, pp. 3915-3925.
Craig L. Slingluff, Jr.,et al., "Phase I Trial of a Melanoma Vaccine with gp100 280-288 Peptide and Tetanus Helper Peptide in Adjuvant: Immunologic and Clinical Outcomes1", Clinical Cancer Research, vol. 7, 2001, pp. 3012-3024.
Shabnam Tangri, et al., "Structural Features of Peptide Analogs of Human Histocompatibility Leukocyte Antigen Class I Epitopes that Are More Potent and Immunogenic than Wild-Type Peptide", J. Exp. Med., vol. 194, No. 6, 2001, pp. 833-846.
Oka, Y. "Human cytotoxic T-lymphocyte responses specific for peptides of the wild-type Wilms' tumor gene (WT1) product", Immunogenetics, vol. 51 (2) p. 99-107 (Feb. 2000). (with English translation).
Haber, D. A, et al., "An Internal Deletion within an 11 p13 Zinc Finger Gene Contributes to the Development of Wilms' Tumor", Cell, vol. 62, p. 1257-1269 (Jun. 29, 1990).
Yamagami, T., et al., "Growth Inhibition of Human Leukemic Cells by WT1 (Wilms Tumor Gene) Antisense Oligodeoxynucieotides: Implications for the Involvement of WT1 in Leukemogenesis", Blood, vol. 87, No. 7, p. 2878-2884.
Inoue, K., et al., "Wilms' Tumor Gene (WT1) Competes with Differentiation-Inducing Signal in Hematopoietic Progenitor Cells", Blood, vol. 91, No. 8, p. 2969-2976 (Apr. 15, 1998).
Tsuboi, A., et at, "Constitutive expression of the Wilms' tumor gene WT1 inhibits the differentiation of myeloid progenitor cells but promotes their proliferation in response to granulocyte-colony stimulating factor (G-CSF)", Leukemia Research 23, p. 499-505 (1999).
International Preliminary Report on Patentability issued in International Application No. PCT/JP2011/072874, dated Dec. 20, 2011, 9 pages. (with English translation).
International Search Report issued in International Application No. PCT/JP2011/072874, dated Dec. 20, 2011, 3 pages.
International Preliminary Report on Patentability dated May 16, 2013 in PCT/JP2011/072874 (English translation only).
International Search Report and Written Opinion of the International Searching Authority dated Dec. 20, 2011 in PCT/JP2011/072874 (English translations only).
Pakistani Office Action dated Jan. 10, 2013 in Patent Application No. 720/2011.
Rena J. May et al., "Peptide Epitopes from the Wilms' Tumor 1 Oncoprotein Stimulate CD4+ and CD8+ T Cells That Recognize and Kill Human Malignant Mesothelioma Tumor Cells", Clinical Cancer Res., vol. 13, No. 15, Aug. 1, 2007, pp. 4547-4555 and 5226 (with cover page).

International Patent Application No. PCT/JP2011/072874, filed Oct. 4, 2011, by International Institute of Cancer Immunology, Inc. et al.: International Search Report, dated Dec. 20, 2011 (3 pages).
Bruening et al., "Germline intronic and exonic mutations in the Wilm's tumor gene (WT1) affecting urogenital development", Nature Genetic, 1(2), pp. 144-148, 1992.
Office Action dated Aug. 21, 2011 issued in corresponding Israeli Application No. 200,161.
Office Action issued in corresponding European Application No. 08 712 039.0-2404.
Call, KM et al., "Antibodies Specific for Wilms' Tumor (WT) Protein Variant WT33, Useful in Immunoassays to Detect WT33 in Samples and Diagnose e.g. Sporadic Wilms' Tumors", Database Geneseq [Online] Apr. 12, 2002 (Apr. 12, 2002), "WT33 protein fragment sequence # 1.", XP002525441 retrieved from EBI accession No. GSN: AAG78450, Database accession No. AAG78450, abstract.
Penn S.G., et al., "Human Genome-Derived Single Exon Nucleic Acid Probes Useful for Analyzing Gene Expression in Human Adult Liver", Database Geneseq, Human Liver Peptide, SEQ ID No. 30961, DATABASE Geneseq [Online] Feb. 25, 2003 (Feb. 25, 2003), "Human liver peptide, SEQ 10 No. 30961.", XP002525442, retrieved from EBI accession No. GSN: ABG52313, Database accession No. ABG52313, abstract.
Call, KM et al., "Antibodies Specific for Wilms' Tumor (WT) Protein Variant WT33, Useful in Immunoassays to Detect WT33 in Samples and Diagnose e.g. Sporadic Wilms' Tumors", Database Geneseq [Online] Apr. 12, 2002 (Apr. 12, 2002), "WT33 Wilm's tumour protein.", XP002525443, retrieved from EBI accession No. GSP: AAG78443, Database accession No. AAG78443, abstract.
Sugiyama Haruo, et al., Office Action dated Jul. 27, 2010, in Japanese Patent Application No. 2005-515303, filed Nov. 4, 2004.
Chinese Office Action for Chinese Application No. 201310058504.4 dated Sep. 7, 2015, with English translation (4 pages).
Australian Patent Application No. 2011313327, by international Institute of Cancer immunology, Inc. et al.: Patent Examination Report No. 1, dated Jun. 2, 2014 (5 pages).
Taiwan Patent Application No. 100135857, by International Institute of Cancer Immunology, Inc., et al., Examination Report and Search Report, dated Apr. 7, 2015, with English translation (16 pages).
Canadian Patent Application No. 2677,075, by International Institute of Cancer Immunology, Inc.: Office Action, dated May 14, 2014 (3 pages).
Chinese Patent Application No. 201180058552.2, filed Oct. 4, 2011, by International institute of Cancer Immunology, Inc.: First Office Action; dated Apr. 9, 2014, with English translation (15 pages).
Chinese Patent Application No. 201310009095.9, tiled Feb. 27, 2008, by International Institute of Cancer Immunology, Inc.: Second Office Action, dated Jul. 31, 2014, with English translation (9 pages).
European Patent Application No. 11830662.0, by International institute of Cancer Immunology, Inc., et al.: Examination Report (Communication pursuant to Article 94(3) EPC), dated Jun. 23, 2015 (3 pages).
Fujiki, F. et al. (2004) "Identification of HLA class II restricted WT1 peptide which can induce WT1-specific CD4+ helper T cells" Proceedings of the Japanese Society tor immunology, 34:210, Abstract 2-G-W29-08-0/P, With English translation.
International Patent Application No. PCT/JP2011/072874, filed Oct. 4, 2011, by International Institute of Cancer Immunology, Inc. et al.: International Preliminary Report on Patentability, including Notification of Transmittal, dated May 16, 2013 (10 pages).
International Patent Application No. PCT/JP2013/083580, filed Dec. 16, 2013, by Otsuka Pharmaceutical Co., Ltd, et al.: International Search Report, dated Feb. 25, 2014 (5 pages).
International Patent Application No. PCT/JP2013/083580, filed Dec. 16, 2013, by Otauka Pharmaceutical Co., Ltd. et al.: International Preliminary Report on Patentability, including Notification of Transmittal, dated Jul. 2, 2015 (9 pages).
Canadian Office Action issued in corresponding Canadian Application No. 2,544,214, dated May 3, 2012, Sugiyama, Haruo, "HLA-DR-Binding Antigen Peptide Derived From WT1", 3 pp.

(56) References Cited

OTHER PUBLICATIONS

Call, KM et al., "Antibodies Specific for Wilms' Tumor (WT) Protein Variant WT33, Useful in Immunoassays to Detect WT33 in Samples and Diagnose e.g. Sporadic Wilms' Tumors", cited in European Search Report of EP 09003839.9, AAG78443 standard; protein; 345 AA, WT33 Wilms' Tumour Protein, Database Geneseq, XP-002525443, dated Apr. 12, 2002, 2 pages.
Penn S.G., et al., "Human Genome-Derived Single Exon Nucleic Acid Probes Useful for Analyzing Gene Expression in Human Adult Liver", cited in European Search Report of EP 09003839.9, ABG52313 standard; peptide; 37 AA, Database Geneseq, Human Liver Peptide, SEQ ID No. 30961, XP-002525442, dated Feb. 25, 2003, 1 page.
Call, KM et al., "Antibodies Specific for Wilms' Tumor (WT) Protein Variant WT33, Useful in Immunoassays to Detect WT33 in Samples and Diagnose e.g. Sporadic Wilms' Tumors", cited in European Search Report of EP 09003839.9, (MASI) Massachusetts Inst. Technology, Database Geneseq, WT33 Protein Fragment Sequence # 1, XP-002525441 , dated Apr. 12, 2002, 1 page.
Gaiger, A., et al., "Compositions and Methods for WT1 Specific Immunotherapy", cited in European Search Report of EP 04799497.5, Sequence 21 AA; dated Aug. 13, 2002, XP-002473316, 1 page.
Database JPO Proteins [Online] Jul. 17, 2003, Mayumi, T, et al., "Cancer vaccine comprising cationic liposome and cancer antigen based on tumor suppressor gene WT1", cited in European Search Report of EP 04799497.5, XP002473130, 1 pp.
Singh et al., "Propred: Prediction of HLA-DR Binding Sites", Bioinformatics Centre, Institute of Microbial Technology, Sector 39A, Chandigarh-160036, India, Bioinformatics Applications, vol. 17, No. 12, Oxford University Press 2001, pp. 1236-1237.
Peter G. Maslak, et al., "Vaccination with synthetic analog peptides derived from WT1 oncoprotein induces T-cell responses in patients with complete remission from acute myeloid leukemia" , www.bloodjournal.org, Blood, Jul. 15, 2010, vol. 116, No. 2, pp. 171-179.
Akihiro Tsuboi, et al., "Enhanced induction of human WT1-specific cytotoxic T lymphocytes with a 9-mer WT1 peptide modified at HLA-A*2402-binding residues", Cancer Immunol Immunother (2002) 51: 614-620.
Akiki Katsuhara, et al., "Transduction of a Novel HLA-DRB1*04:05-restricted, WT1-specific TCR Gene into Human CD4+ T Cells Confers Killing Activity Against Human Leukemia Cells", Anticancer Research 35: 1251-1262 (2015).
Junji Yatsuda, et al., "Establishment of HLA-DR4 Transgenic Mice for the Identification of CD4+ T Cell Epitopes of Tumor-Associated Antigens", PLOS ONE, www.plosone.org, Dec. 2013 , vol. 8 , Issue 12, e84908, 1-12.
Office Action issued in Examination Report in related Pakistan Patent Application No. 720/2011, dated Jan. 10, 2013, 2 pages.
May, R. J., et al., "Peptide Epitopes from the Wilms' Tumor 1 Oncoprotein Stimulate CD4 + and CD8 +• T Cells That Recognize and Kill Human Malignant Mesothelioma Tumor Cells", Clin. Cancer Res., vol. 13, No. 15, p. 4547-4555 (Aug. 1, 2007). (with English translation).
Lehe, C., et al., The Wilms' Tumor 1 Oncoprotein Stimulate CD44 Regulatory T Cells: Implications for Immunotherapy, Cancer Research, vol. 68(15), p. 6350-6359 (Aug. 1, 2008). (with English translation).
Knights, A. J., et al., "Prediction of an HIA-DR-binding peptide derived from Wilms' Tumour 1 protein and demonstration of in vitro immunogenicity of WT1(124-138)-pulsed dentritic cells generated according to an optimized protocol", Cancer Immunol, Immunother, vol. 51, p. 271-281 (2002). (with English translation).
English Translation of Office Action dated Nov. 29, 2013, issued in Chinese Patent Application No. 201310009095.9.
First Office Action issued by the State Intellectual Property Office, P.R. China in related Chinese Patent Application No. 20118005852.2, dated, Apr. 9, 2014, 15 pages. (with English translation).
Office Action issued by the Australian Government IP Australia in related Australian Patent Application No. 2011313327, dated, Jun. 2, 2014, 5 pages. (with English translation).
Office Action issued by the Taiwanese Intellectual Property Office in related Taiwanese Patent Application No. 100135857, dated Apr. 7, 2015, 16 pages. (with English translation).
Office Action issued by the Canadian Intellectual Property Office in related Canadian Patent Application No. 2,677,075, dated May 14, 2014, 3 pages.
Office Action issued by the State Intellectual Property Office, P.R. China, in related China Patent Application No. 201310009095.9, dated Jul. 31, 2014, 9 pages. (with English translation).
Office Action issued by the European Patent Office in related European Patent Application No. 11 830 662.0, dated Jun. 23, 2015, 3 pages.
Reexamination Decision, dated Feb. 17, 2015, issued in Chinese Patent Application No. 200860006098:5.
Summons to attend oral proceedings issued European Patent Application No. 08712039.0, dated Oct. 23, 2014 (6 pages).
Biology stack exchange_biology_stackexchange.com/questions/5612, 2014.
Office Action with search report dated Jun. 26, 2014, issued in Chinese Patent Application No. 201310058504.4.
Office Action dated Dec. 12, 2013, issued in Indian Patent Application No. 4956/CHENP/2009.
Office Action dated Aug. 14, 2013, issued in Russian Patent Application No. 2009135802.
Office Action dated May 28, 2013, issued in Vietnamese Patent Application No. 1-2009-01834.
Office Action dated May 28, 2013, issued in Colombian Patent Application No. 09103658.
Office Action dated Dec. 31, 2012, issued in Malaysian Patent Application No. P320093253.
Office Action dated Dec. 12, 2012, issued in Russian Patent Application No. 2009135602/10.
Office Action dated Oct. 2, 2012, issued in Australian Patent Application No. 2008220031.
Office Action dated Sep. 25, 2012, issued in Japanese Patent Application No. 2009-501276.
Correspondence dated Aug. 22, 2012, forwarding and describing Official Action issued in the corresponding Colombian Patent Application No. 09103858, 5 pages.
Office Action dated Dec. 12, 2011, issued in corresponding Russian Application No. 2009135802.
Office Action dated Nov. 29, 2011 issued in corresponding Ukrainian Application No. 200909812.
Office Action dated Jan. 9, 2012, issued in corresponding New Zealand Application No. 5787215.
Office Action dated Feb. 24, 2012 issued in corresponding Mexican Application No. MX/a/2009/009168.
Office Action dated Feb. 24, 2012 issued in corresponding European Application No. 08 712 039.0-2404.
Office Action issued in corresponding Mexican Application No. MX/a/2009/009168.
Office Action issued in corresponding New Zealand Application No. 578721.
Office Action dated Nov. 8, 2011 issued in corresponding Chinese Application No. 200880006096.5.
Examination Report dated Sep. 23, 2011 issued in corresponding New Zealand Application No. 578721.
Official Action dated Jun. 15, 2012, issued in the corresponding Russian Patent Application No. 2009135802, including the English translation thereof (9 pages).
English translation of Official Action dated Jun. 15, 2012, issued in the corresponding Russian Patent Application No. 2009135802 (9 pages).
English summary dated Jun. 21, 2012, of Office Action issued in the corresponding Mexican Patent Application No. MX/a/2009/009168.
Third Office Action dated Mar. 28, 2012, issued in the corresponding Chinese Patent Application No. 20088000609.5.
Office Action dated Mar. 2, 2012 issued in corresponding Ukrainian Patent Application No. 2009 09812.
Supplementary European Search Report dated Jul. 20, 2010 issued in corresponding European Patent Application No. 08712039.0-2404.

(56) References Cited

OTHER PUBLICATIONS

Office Action dated May 5, 2011 issued in corresponding Chinese Application No. 200880006096.5.
Biology Stack Exchange, Inc. "Do T-cells express MHC Molecules?" [online]biology.stackexchange.com/questions/5612. Retrieved Sep. 2014 (1 page).
Freshney, R.I., Culture of Animal Cells, A Manual of Basic Technique. New York: Alan R. Liss, Inc., 1983; p. 3-4.
Gao, F.G. et al. (Nov. 2002) "Antigen-specific CD4+ T-Cell Help Is Required to Activate a Memory CD8+ T Cell to a Fully Functional Tumor Killer Cell" Cancer Research, 62:6438-6441.
GENSEQ Accession No. AEA15677, First entry Date Jul. 28, 2005 (3 pages).
Marsh, S.E. et al., The HLA Facts Book. London, England: Academic Press, 2000; pp. 299 and 377 (4 pages, including cover and copyright pages).
Australian Patent Application No. 2008220031, by International Institute of Cancer Immunology, Inc.: Examination Report No. 1, dated Oct. 2, 2012 (3 pages).
Chinese Patent Application No. 200880006096.5, by International Institute of Cancer Immunology, Inc.: Office Action, dated May 5, 2011, with partial English translation.
Chinese Patent Application No. 200880006096.5, by International Institute of Cancer Immunology, Inc.: Second Office Action, dated Nov. 8, 2011, with English translation.
Chinese Patent Application No. 200880006096.5, by International Institute of Cancer Immunology, Inc.: Third Office Action, dated Mar. 28, 2012, with English translation.
Chinese Patent Application No. 200880006096.5, by International Institute of Cancer Immunology, Inc.: Reexamination Decision, dated Feb. 17, 2015, with English translation.
Chinese Patent Application No. 201310009095.9, by International Institute of Cancer Immunology, Inc.: English Translation of First Office Action and Search Report, dated Nov. 29, 2013.
Chinese Patent Application No. 201310058504.4, by International Institute of Cancer Immunology, Inc.: First Office Action and Search Report, dated Jun. 26, 2014, with English translation.
Chinese Patent Application No. 201310058504.4, by International Institute of Cancer Immunology, Inc.: Third Office Action, dated Sep. 7, 2015, with English translation.
Colombian Patent Application No. 09103858: Correspondence dated Aug. 22, 2012, from Cavelier to Aoyama & Partners, forwarding and describing Official Action (5 pages) (English).
Colombian Patent Application No. 09103858. Office Action dated May 28, 2013, with English translation (10 pages). European Patent Application No. 08712039.0, by International Institute of Cancer Immunology, Inc.: Extended European Search Report, including Supplementary European Search Report and Search Opinion, dated Jul. 20, 2010 (6 pages).
European Patent Application No. 08712039.0, by International Institute of Cancer Immunology, Inc.: Communication pursuant to Article 94(3) EPC, dated Feb. 24, 2012 (5 pages.).
European Patent Application No. 08712039.0, by International Institute of Cancer Immunology, Inc.: Summons to attend oral proceedings pursuant to Rule 115( 1) EPC, dated Oct. 23, 2014 (6 pages).
Indian Patent Application No. 4956/CHENP/2009: First Examination Report, dated Dec. 12, 2013 (2 pages) (English).
International Patent Application No. PCT/JP2013/083580, filed Dec. 16, 2013, by Otsuka Pharmaceutical Co., Ltd. et al.: International Preliminary Report on Patentability, including Notification of Transmittal, dated Jul. 2, 2015 (9 pages).
Israel Patent Application No. 200,161, by International Institute of Cancer Immunology, Inc.: Office Action, dated Aug. 21, 2011, with English summary letter from Dr. Yitzhak Hess & Partners to Aoyama & Partners, dated Sep. 4, 2011. (English language Summary).
Japanese Patent Application No. 2009-501276: Office Action, dated Sep. 25, 2012, with partial English translation.
Malaysian Patent Application No. PI20093253, by International Institute of Cancer Immunology, Inc.: Substantive Examination Adverse Report, including Search Report, dated Dec. 31, 2012 (3 pages) Mexican Patent Application No. MXIa/2009/009168, by International Institute of Cancer Immunology, Inc.: Correspondence dated Feb. 24, 2012, from Becerril, Coca & Becerril, S.C. to Aoyama & Partners providing an English summary of an official letter received from the Mexican Institute of Industrial Property (9 pages). (English).
Mexican Patent Application No. MX/a/2009/009168, by International Institute of Cancer Immunology, Inc.: Correspondence dated Feb. 24, 2012, from Becerril, Coca & Becerril, S.C. to Aoyama & Partners providing an English summary of an official letter received from the Mexican Institute of Industrial Property (9 pages).
Office Action dated Jul. 27, 2010, in Japanese Patent Application No. 2005-515303.
Office Action dated Mar. 7, 2014 issued in divisional U.S. Appl. No. 13/755,185, Applicant: Haruo Sugiyama, Filing date: Jan. 31, 2013, Entitled: HLA-DR-Binding Antigen Peptide Derived From WT1, 15 pp.
Gaiger, A. & Cheever, M., Database JPO Proteins [Online] Jul. 17, 2003, "Compositions and methods for WT1 specific immunotherapy", Sequence 21 AA, cited in European Search Report of EP 04799497.5, XP002473316.
Call, KM et al., "Antibodies Specific for Wilms' Tumor (WT) Protein Variant WT33, Useful in Immunoassays to Detect WT33 in Samples and Diagnose e.g. Sporadic Wilms' Tumors", Database Geneseq, WT33 Wilms' Tumour Protein, XP-002525443, Apr. 12, 2002, 2 pages, cited in EP Search Report EP 09003839.9.
Penn S.G., et al., "Human Genome-Derived Single Exon Nucleic Acid Probes Useful for Analyzing Gene Expression in Human Adult Liver", Database Geneseq, Human Liver Peptide, SEQ ID No. 30961, XP-002525442, Feb. 25, 2003, 1 page, cited in EP Search Report EP 09003839.9.
Call, KM et al., "Antibodies Specific for Wilms' Tumor (WT) Protein Variant WT33, Useful in Immunoassays to Detect WT33 in Samples and Diagnose e.g. Sporadic Wilms' Tumors", Database Geneseq, WT33 Protein Fragment Sequence # 1, XP-002525441, Apr. 12, 2002, 1 page.
Mayumi, T, et al., "Cancer vaccine comprising cationic liposome and cancer antigen based on tumor suppressor gene WT1", Jul. 17, 2003, cited in European Search Report of EP 04799497.5, (WO03002142-A2), XP002473130, 1 pp.
Rena J. May PhD., et al., "CD4+ Peptide Epitopes from the WT1 Oncoprotein Stimulate CD4+ and CD8+ T Cells That Recognize and Kill Leukemia and Solid Tumor Cells" Blood (ASH Annual Meeting Abstracts) 2006 108: Abstract 3706© 2006 American Society of Hematology, 1 pg., cited in EP Search Report EP04799497.5., XP009097422.
Janeway et al., "Antigen Recognition by B-Cell and T-Cell Receptors", Immune Biology, 5th edition, pp. 116-117, Garland Science; New York; Eds., Janeway, et al., 2001, (Plus Cover Letter), 3 pages total.
Office Action dated Mar. 7, 2014 issued in divisional U.S. Appl. No. 13/755,185, filed Jan. 31, 2013, Inventor: Haruo Sugiyama , et al., Titled: "HLA-DR-Binding Antigen Peptide Derived From WT1", 15 pp.
Healthline.com, "Non-hodgkin's Lymphoma: In Depth-Overview", pp. 1-3, http://www.healthline.com/channel/non-hodgkins-lymphoma_indepth-overview, retrieved Dec. 2, 2008. Cited in U.S. Appl. No. 13/755,185 on PTO-892 Mar. 7, 2014.
Mexican Patent Application No. MXIa/2009/009168, by International Institute of Cancer Immunology, Inc.: Correspondence dated Jun. 21, 2012, from Becerril, Coca & Becerril, S.C. to Aoyama & Partners providing an English summary of a second official letter received from the Mexican Institute of Industrial Property (5 pages).
New Zealand Application No. 5787215, by International Institute of Cancer Immunology, Inc.: Report, dated Sep. 23, 2011 (2 pages).
New Zealand Application No. 5787215, by International Institute of Cancer Immunology, Inc.: Examination Report, dated Jan. 9, 2012 (3 pages).

(56) References Cited

OTHER PUBLICATIONS

Russian Patent Application No. 2009135802, by International Institute of Cancer Immunology: Office Action dated Dec. 12, 2011, including English translation (15 pages).
Russian Patent Application No. 2009135802, by International Institute of Cancer Immunology: Notification About Results of a Check of Patentability, received Dec. 12, 2012, with English translation (9 pages).
Russian Patent Application No. 2009135802, by International Institute of Cancer Immunology: Official Action, dated Jun. 15, 2012, including the English translation (9 pages).
Russian Patent Application No. 2009135802, by International Institute of Cancer Immunology: Decision on Rejection to Grant a Patent for Invention, dated Aug. 14, 2013, with English translation (13 pages).
Ukrainian Patent Application No. 200909812, by International Institute of Cancer Immunology, Inc.: Official Action, dated Nov. 29, 2011, with English translation (6 pages).
Ukrainian Patent Application No. 200909812, by International Institute of Cancer Immunology, Inc.: Official Action, dated Mar. 2, 2012, with English translation (8 pages).
Vietnamese Patent Application No. 1-2009-01834, by International Institute of Cancer Immunology, Inc.: Office Action, dated May 28, 2013, with English translation (2 pages).
U.S. Appl. No. 12/449,765, filed Aug. 26, 2009, by Sugiyama: Non-Final Rejection, dated Apr. 3, 2012 (15 pages).
U.S. Appl. No. 12/449,765, filed Aug. 26, 2009, by Sugiyama: Final Rejection, dated Sep. 26, 2012 (11 pages).
U.S. Appl. No. 12/449,765, filed Aug. 26, 2009, by Sugiyama: Non-Final Rejection, dated Sep. 8, 2014 (14 pages).
U.S. Appl. No. 12/449,765, filed Aug. 26, 2009, by Sugiyama: Final Rejection, dated Mar. 17, 2015 (11 pages).
International Preliminary Report on Patentability issued in corresponding International Application No. PCT/JP2013/083580, dated Feb. 25, 2014,10 pages.
International Preliminary Report issued in corresponding International Application No. PCT/JP2013/083580, dated Feb. 25, 2014, 5 pages.
Fujiki, F., "A Wt1 protein-derived, naturally processed 16-mer peptide, WT1 $_{332}$, is a promiscuous helper peptide for induction of WT1-specific Th 1-type CD4 T cells", Microiol. Immunol., vol. 52, p. 591-600, 10 pages (2008).
Sugiyama, H., "WT1 Peptide-Based Cancer Immunotherapy", Biotherapy, vol. 21(5), pp. 299-306, (Sep. 2007).
Fujiki, F., "Identification of WT1 peptide which can induce WT1-specific CD4+ helper T cells in an HLA-class II-restricted manner and examination of the usefulness of the peptide", Proceedings of the Japanese Society for Immunology, 35, p. 187, 3 pages (2005).
Office Action dated Sep. 8, 2014 in co-pending U.S. Appl. No. 12/449,765.
Office Action dated Apr. 3, 2012 in co-pending U.S. Appl. No. 12/449,765.
Office Action dated Mar. 17, 2015 in co-pending U.S. Appl. No. 12/449,765.
Office Action dated Sep. 26, 2012 in co-pending U.S. Appl. No. 12/449,765.
Office Action dated Sep. 7, 2015 in Chinese Patent Application No. 201310058504.4 (with English language translation).
Office Action dated May 14, 2014 in Canadian Patent Application No. 2,677,075.
Office Action dated Jul. 31, 2014 in Chinese Patent Application No. 201310009095.9 (with English language translation).
Office Action dated Jun. 23, 2015 in European Patent Application No. 11 830 662.0.
International Search Report dated May 13, 2008 in PCT/JP2008/053417 (with English language translation).
International Preliminary Report on Patentability and Written Opinion dated Sep. 1, 2009 in PCT/JP2008/053417 filed Feb. 27, 2008 (with English language translation).
International Search Report dated Feb. 25, 2014 in PCT/JP2013/083580 (submitting English translation only).
International Preliminary Report on Patentability and Written Opinion dated Jul. 2, 2015 in PCT/JP2013/083580 filed Dec. 16, 2013 (submitting English translation only).
Reexamination Decision dated Feb. 17, 2015 in Chinese Patent Application No. 200880006096.5 (with English language translation).
Office Action dated Oct. 23, 2014 in European Patent Application No. 08712039.0.
Combined Chinese Office Action and Search report dated Jun. 26, 2014 in Patent Application No. 201310058504.4 (with English language translation).
Office Action dated Dec. 12, 2013 in Indian Patent Application No. 4956/CHENP/2009.
Combined Chinese Office Action and Search Report dated Nov. 29, 2013 in Patent Application No. 201310009095.9 (with English language translation).
Office Action dated Aug. 14, 2013 in Russian Patent Application No. 2009135802/10 (with English language translation).
Office Action dated May 28, 2013 in Vietnamese Patent Application No. 1-2009-01834 (with English language translation).
Office Action dated May 28, 2013 in Colombian Patent Application No. 09-103858 (with partial English translation).
Office Action dated Dec. 31, 2012 in Malaysian Patent Application No. PI 20093253.
Office Action dated Dec. 12, 2012 in Russian Patent Application No. 2009135802/10 (with English language translation).
Office Action dated Oct. 2, 2012 in Australian Patent Application No. 2008220031.
Office Action dated Sep. 25, 2012 in Japanese Patent Application No. 2009-501276 (with partial English translation).
Office Action dated Aug. 22, 2012 in Colombian Patent Application No. 09-103858 (submitting English translation only).
Office Action dated Jun. 15, 2012 in Russian Patent Application No. 2009135802/10 (with English language translation).
Summary of Office Action dated Jun. 21, 2012 in Mexican Patent Application No. MX/a/2009/009168 (submitting English translation only).
Office Action dated Mar. 28, 2012 in Chinese Patent Application No. 200880006096.5 (with English language translation).
Extended European Search Report dated Jul. 20, 2010 in Patent Application No. 08712039.0.
Office Action dated May 5, 2011 in Chinese Patent Application No. 200880006096.5 (with English language translation).
Examination Report dated Sep. 23, 2011 in New Zealand Patent Application No. 578721.
Office Action dated Aug. 21, 2011 in Israeli Patent Application No. 200,161 (with partial English translation).
Office Action dated Nov. 8, 2011 in Chinese Patent Application No. 200880006096.5 (with English language translation).
Office Action dated Dec. 12, 2011 in Russian Patent Application No. 2009135802/10 (submitting English translation only).
Office Action dated Nov. 29, 2011 in Ukrainian Patent Application No. 200909812 (with English language translation).
Examination Report dated Jan. 9, 2012 in New Zealand Patent Application No. 578721.
Summary of Office Action dated Feb. 24, 2012 in Mexican Patent Application No. MX/a/2009/009168 (submitting English translation only).
Office Action dated Feb. 24, 2012 in European Patent Application No. 08 712 039.0.
Office Action dated Mar. 2, 2012 in Ukrainian Patent Application No. 200909812 (with English language translation).
"Do T-cells express MHC molecules?" Biology Stack Exchange, http://biology.stackexchange.com/questions/5612/do-t-cells-express-mhc-molecules, 2014, 1 Page.
Gerald B. Dermer "The Last Word: Another Anniversary for the War on Cancer" Bio/Technology, vol. 12, Mar. 1994, p. 320.
Marie Marchand, et al., "Biological and Clinical Developments in Melanoma Vaccines" Expert Opinion on Biological Therapy, vol. 1, No. 3, Ashley Publications Ltd. 1471-2598, 2001, pp. 497-510.

(56) References Cited

OTHER PUBLICATIONS

Philippe Fournier, et al., "Randomized clinical studies of anti-tumor vaccination: State of the art in 2008" Expert Reviews Vaccines, vol. 8, No. 1, 2009, pp. 51-66.
Taylor H. Schrieber, et al., "Tumor immunogenicity and responsiveness to cancer vaccine therapy: The state of the art" Seminars in Immunology, vol. 22, 2010, pp. 105-112.
Christopher A. Klebanoff, et al., "Therapeutic Cancer Vaccines: Are We There Yet?" Immunological Reviews, vol. 239, 2011, pp. 27-44.
Fumihiro Fujiki, et al., "Identification and Characterization of a WT1 (Wilms Tumor Gene) Protein-derived HLA-DRBI *0405-restricted 16-mer Helper Peptide That Promotes the Induction and Activation of WT1-specific Cytotoxic T Lymphocytes" Journal of Immunotherapy, vol. 30 No. 3, Apr. 2007, pp. 282-293.
Marie Marchand, et al., "Tumor regressions observed in patients with metastatic melanoma treated with an antigenic peptide encoded by gene MAGE-3 and presented by HLA-A1" International Journal of Cancer, vol. 80, No. 2, Jan. 1999, pp. 219-230.
Bela Bodey, et al., "Failure of Cancer Vaccines: The Significant Limitations of this Approach to Immunotherapy" Anticancer Research, vol. 20, 2000, pp. 2665-2676.
Ping Gao, et al., "Tumor Vaccination That Enhances Antitumor T-Cell Responses Does Not Inhibit the Growth of Established Tumors Even in Combination With Interleukin-12 Treatment: The Importance of Inducing Intratumoral T-Cell Migration" Journal of Immunotherapy, vol. 23, No. 6, http://ovidsp.tx.ovid.com/spa/ovidweb.cgi, 2000, pp. 643-653.
Esteban Celis "Getting Peptide Vaccines to Work: Just a Matter of Quality Control?" Journal of Clinical Investigation, vol. 110, No. 12, Dec. 15, 2002, pp. 1765-1768.
A_GENSEQ AEA15677, Jul. 28, 2005, 3 Pages.
Maresa Altomonte, et al., "Targeted therapy of solid malignancies via HLA class II antigens; a new biotherapeutic approach?" Oncogene, vol. 22, 2003, pp. 6564-6569.
Marlene Silva Bardi, et al., "HLA-A, B and DRB1 allele and haplotype frequencies in volunteer bone marrow donors from the north of Parana State" Revista Brasileira de Hematologia e Hemoterapia, vol. 34, No. 1, 2012, pp. 25-30.
Jörn Dengjel, et al., "Unexpected Abundance of HLA Class II Presented Peptides in Primary Renal Cell Carci nomas" Clinical Cancer Research, vol. 12, No. 14, Jul. 15, 2006, pp. 4163-4170 and Cover Page.
Fumihiro Fujiki, et al., "Identification of HLA-class II restricted WT1 peptide which can induce WT1-specific CD4+ helper T cells" Abstract 2-G-W29-08-O/P, Proceedings of the Japanese Society for Immunology, vol. 34, 2004, p. 210 and Cover Page (with English language translation).
Fumihiro Fujiki, et al. "Identification of WT1 peptide which can induce WT1-specific CD4+ helper T cells in an HLA-class II-restricted manner and examination of the usefulness of the peptide" Abstract 2-F-W27-8-O/P, Proceedings of the Japanese Society for Immunology, vol. 35, 2005, p. 187 and Cover Page (with English language translation).
Fang Han, et al., "HLA-DQ association and allele competition in Chinese narcolepsy" Tissue Antigens, vol. 80, 2012, pp. 328-335 (with English Translation).
Peter Wendelboe Hansen, et al., "Cytotoxic Human HLA Class II Restricted Purified Protein Derivative-Reactive T-Lymphocyte Clones: IV. Analysis of HLA Restriction Pattern and Mycobacterial Antigen Specificity" Scandinavian Journal of Immunology, vol. 25, No. 3, 1987, pp. 295-303 and Cover Page.
Kimberley D. House, et al., "The search fora missing HLA-DRB1*09 Allele" Abstract 23-OR, 38th Annual Meeting of the American Society for Histocompatibility and Immunogenetics, Abstracts/Human Immunology, vol. 73, Oct. 8-12, 2012, p. 20 and Cover Pages.
Atsushi Irie, et al., "Establishment of HLA-DR4 transgenic mice having antigen-presenting function to HLA-DR4-restricted CD4+ Th cell" Abstract O-36(P-80), MHC (Major Histocompatibility Complex), Official Journal of the Japanese Society for Histocompatibility and Immunogenetics, vol. 19, No. 2, Aug. 10, 2012, p. 94 and Cover Pages (with English language translation).
Akiko Katsuhara, et al., "Transduction of a Novel HLA-DRB1*04:05-restricted, WT1-specific TCR Gene into Human CD4+ T Cells Confers Killing Activity Against Human Leukemia Cells" Anticancer Research, vol. 35, 2015, pp. 1251-1261.
Keith L. Knutson, et al., "Tumor antigen-specific T helper cells in cancer immunity and immunotherapy" Cancer Immunology, Immunotherapy, vol. 54, No. 8, 2005, pp. 721-728.
Yuhung Lin, et al., "HLA-DPB1*05:01-restricted $WT1_{332}$-specific TCR-transduced CD4+ T Lymphocytes Display a Helper Activity for WT1-specific CTL Induction and a Cytotoxicity Against Leukemia Cells" Journal of Immunotherapy, vol. 36, No. 3, Apr. 2013, pp. 159-170.
Peter S. Master, et al., "Patterns of Membrane Antigen Expression by AML Blasts: Quantitation and Histogram Analysis" Leukemia and Lymphoma, vol. 5, 1991, pp. 317-325.
Francesca Megiorni, et al., "HLA-DQA1 and HLA-DQB1 in Celiac disease predisposition: practical implications of the HLA molecular typing" Journal of Biomedical Science, vol. 19, No. 88, 2012, 5 pages.
A. S. Mustafa, et al., "BCG induced CD4+ cytotoxic T cells from BCG vaccinated healthy subjects: relation between cytotoxicity and suppression in vitro" Clinical and Experimental Immunology, vol. 69, No. 2, 1987, pp. 255-262.
Katayoun Rezvani, et al., "T-Cell Responses Directed against Multiple HLA-A*0201-Restricted Epitopes Derived from Wilms' Tumor 1 Protein in Patients with Leukemia and Healthy Donors: Identification, Quantification, and Characterization" Clinical Cancer Research, vol. 11, No. 24, Dec. 15, 2005, pp. 8799-8807 and Cover Page.
Shinji Sogo, "Final Study Report: Effect of OVT-101 on the Helper-activity Against WT1-specific CTL From Human Peripheral Blood Mononuclear Cells" Otsuka Pharmaceutical Co. Ltd., Study No. 030697, Report No. 025539, completed on Dec. 9, 2010 (22 pages).
Shinji Sogo, "Final Study Report: Cytolytic Activity of OCV-501-Specific Th1 Clones" Otsuka Pharmaceutical Co. Ltd., Study No. 035171, Report No. 028745, completed on Mar. 15, 2013 (39 pages).
Haruo Sugiyama, "WT1-targeting cancer vaccine" Japanese Journal of Clinical Medicine, vol. 70, No. 12, 2012, pp. 2105-2113 (Japanese with English abstract).
Haruo Sugiyama, "WT1 Peptide-Based Cancer Immunotherapy" Biotherapy, vol. 21, No. 5, Sep. 2007, pp. 299-306 (Japanese with English abstract).
K. L. Yang, et al., "An HLA-A*02:01-B*13:01-DRB1*14:01:03 haplotype conserved in Taiwanese and a possible close relationship between DRB1*14:01:03 and DRB1*14:54" International Journal of Immunogenetics, vol. 38, 2010, pp. 69- 71.
Takuya Yazawa, et al., "Lack of class II transactivator causes severe deficiency of HLA-DR expression in small cell lung cancer" Journal of Pathology, vol. 187, 1999, pp. 191-199.
Sachiko Futami, et al., "HLA-DRB1*1502 Allele, Subtype of DR15, Is Associated with Susceptibility to Ulcerative Colitis and Its Progression" Digestive Diseases and Sciences, vol. 40, No. 4, Apr. 1995, pp. 814-818.
R. Sotiriadou, et al., "Peptide HER2(776-788) represents a naturally processed broad MHC class II-restricted T cell epitope" British Journal of Cancer, vol. 85, No. 10, 2001, pp. 1527-1534.
John A. Hural, et al., "Identification of Naturally Processed CD4 T Cell Epitopes from the Prostate-Specific Antigen Kallikrein 4 Using Peptide-Based in Vitro Stimulation" The Journal of Immunology, vol. 169, No. 1, 2002, pp. 557-565 and Cover Page.
Paul H. Naylor, et al., "Peptide Based Vaccine Approaches for Cancer-A Novel Approach Using a WT-1 Synthetic Long Peptide and the IRX-2 Immunomodulatory Regimen", Cancers 2011, 3, 3991-4009; doi:10.3390/Cancers3043991.
U.S. Appl. No. 13/877,768, Non-Final Rejection dated Nov. 20, 2017.
Karin N. et al., The Journal of Experimental Medicine, Dec. 1, 1994, 180 (6): 2227-2237 (Cited in D1).

(56) References Cited

OTHER PUBLICATIONS

Patel S. D. et al., Proc, Natl. Acad. Sci. USA, vol. 94, Jul. 1997 (Jul. 1, 1997), pp. 8082-8087 (Cited in D1).
Del Rincón et al., Arthritis & Rheumatism (2003) vol. 49, pp. 200-208.
Nikbin et al., Iran J Allergy Asthma Immunol (2017) 16(1), pp. 1-13.
Marsh et al., Tissue Antigens (2005) 65, pp. 301-369.
U.S. Appl. No. 10/578,183, Non-Final Rejection dated Sep. 13, 2017.
U.S. Appl. No. 13/877,768, Final Rejection dated Dec. 28, 2016.
Final Office Action dated Jun. 11, 2018 issued in U.S. Appl. No. 13/877,768.
M. DiBrino, et al. "HLA-A1 and HLA-A3 T Cell Epitopes Derived from Influenza Virus Proteins Predicted from Peptide Binding Motifs", J. Immunology, vol. 151, No. 11, Dec. 1, 1993, pp. 5930-5935.
E. Celis, et al., "Identification of Potential CTL Epitopes of Tumor-Associated Antigen Mage-1 for Five Common HLA-A Alleles", Molec. Immunol., vol. 31, No. 18, 1994, pp. 1423-1430.
U.S. Appl. No. 13/877,768, filed Jun. 21, 2013, by Sugiyama et al.: Final Rejection dated Dec. 28, 2016.
U.S. Appl. No. 13/877,768, filed Jun. 21, 2013, by Sugiyama et al.: Non-Final Rejection dated Jun. 2, 2016.
U.S. Appl. No. 13/877,768, filed Jun. 21, 2013, by Sugiyama et al.: Non-Final Rejection dated Nov. 20, 2017.
U.S. Appl. No. 12/449,765, filed Aug. 26, 2009, by Sugiyama: Final Rejection, dated Mar. 17, 2015.
U.S. Appl. No. 12/449,765, filed Aug. 26, 2009, by Sugiyama: Final Rejection, dated Sep. 26, 2012.
U.S. Appl. No. 12/449,765, filed Aug. 26, 2009, by Sugiyama: Non-final Rejection, dated Apr. 3, 2012.
U.S. Appl. No. 12/449,765, filed Aug. 26, 2009, by Sugiyama: Non-final Rejection, dated Nov. 16, 2016.
U.S. Appl. No. 12/449,765, filed Aug. 26, 2009, by Sugiyama: Non-Final Rejection, dated Sep. 8, 2014.
U.S. Appl. No. 14/652,298, filed Jun. 15, 2015, by Kubo: Requirement for Restriction/Election, dated Aug. 9, 2016, with Notice of References Cited(PTO-982).
Altomonte M. et al. (2003) "Targeted therapy of solid malignancies via HLA class II antigens: a new biotherapeutic approach?" Oncogene, 22:6564-6569.
Bardi, M.S. et al. (2012) "HLA-A, B and DRB1 allele and haplotype frequencies in volunteer bone marrow donors from the north of Parana State" Rev. Bras. Hematol. Hemoter., 34(1):25-30.
Biology Stack Exchange. biology.stackexchange.com/questions/5612, (2014).
Bodey, B. et al. (Jul. 2000) "Failure of cancer vaccines: the significant limitations of this approach to immunotherapy" Anticancer Research; 20(4):2665-2676.
Bruening, W. et al, (May 1992) "Germline intronic and exonic mutations in the Wilms' tumour gene (WT1) affecting urogenital development"; Nature Genetics 1:144-148.
Celts, E (Dec. 2002) "Getting peptide vaccines to work: just a matter of quality control?" The Journal of Clinical Investigation, 110(12):1765-1768.
Database GenBank Accession No. AAC60604.1 (Jul. 23, 1993) "Wilms' tumor suppressor, partial [*Homo sapiens*]" [online]. National Center for Biotechnology Information (NCBI), U.S. National Library of Medicine; ncbi.nlm.nih.gov/protein/AAC60604.1; retrieved on Feb. 15, 2016.
Database JPO Proteins Accession No. BD589960 [Online] (Jul. 17, 2003), "Cancer vaccine comprising cationic liposome and cancer antigen based on tumor suppressor gene WT1" [online]. Retrieved from EBI on Mar. 17, 2008, Accession No. JPOP: BD589960.
Database JPO Proteins Accession No. BD619917 (Jul. 17, 2003) "Compositions and methods for WT1 specific immunotherapy" [online]. Retrieved from EBI on Mar. 17, 2008, Accession No. JPOP:BD619917.

Dengjel, J. et al. (2006) "Unexpected Abundance of HLA Class II Presented Peptides in Primary Renal Cell Carcinomas" Clin. Cancer Res., 12:4163-4170.
Dermer, G.B. (1994) "Another Anniversary for the war on Cancer" Bio/Technology, 12: 320.
Fournier, P. et al. (2009) "Randomized clinical studies of anti-tumor vaccination" Expert Review of Vaccines, 8(1): 51-66.
Freshney, R.I. (1983) "Culture of animal cells: A manual of basic technique" Alan R. Liss; Inc., New York, p. 4.
Fujiki, F. et al. (2004) "Identification of HLA-class II restricted WT1 peptide which can induce WT1-specific CD4+ helper T cells" Proceedings of the Japanese Society for Immunology, 34:210, Abstract 2-G-W29-08-O/P. Japanese with English translation.
Fujiki, F. et al. (2005) "Identification of WT1 peptide which can induce WT1-specific CD4+ helper T cells in an HLA-class II-restricted manner and examination of the usefulness of the peptide" Proceedings of the Japanese Society for Immunology, 35:187, Abstract 2-F-W27-8-O/P. Japanese with English translation.
Fujiki, F. et al. (2007) "Identification and characterization of a WT1 (Wilms Tumor Gene) protein-derived HLA-DRB1*0405-restricted 16-mer helper peptide that promotes the induction and activation of WT1-specific cytotoxic T lymphocytes" J. Immunother., 30(3):282-293.
Fujiki, F. et al. (Dec. 2008) "A WT1 protein-derived, naturally processed 16-mer peptide, WT1(332), is a promiscuous helper peptide for induction of WT1-specific Th1-type CD4(+) T cells" Microbiol Immunol, 52(12):591-600.
Futami, S. et al. (Apr. 1995)"HLA-DRB1*1502 allele, subtype of DR15, is associated with susceptibility to ulcerative colitis and its progression" Digestive Diseases and Sciences, 40(4):814-818.
Gao, P. et al. (2000) "Tumor Vaccination That Enhances Antitumor T-Cell Responses Does Not Inhibit the Growth of Established Tumors Even in Combination With Interleukin-12 Treatment: The Importance of Inducing Intratumoral T-Cell Migration" Journal of Immunotherapy, 23(6):643-653.
Genseq Accession No. AEA15677, First entry Date Jul. 28, 2005.
Haber, D.A. et al. (Jun. 29, 1990) "An internal deletion within an 11p13 zinc finger gene contributes to the development of Wilms' tumor." 61(7):1257-69.
Han, F. et al. (2012) "HLA-DQ association and allele competition in Chinese narcolepsy" Tissue Antigens, 80:328-335.
Hansen, P.W. et al. (1987) "Cytotoxic Human HLA Class II Restricted Purified Protein Derivative-Reactive T-Lymphocyte Clones" Scan. J. Immunol., 25:295-303.
House, K.D. et al. (2012) "The search for a missing HLA-DRB1*09 Allele" 38th Annual Meeting of the American Society for Histocompatibility and Immunogenetics, Oct. 8-12, 2012, San Juan, Puerto Rico. Abstracts/Human Immunology, 73:20, Abstract 23-OR.
Inoue; K. et al. (1998) "Wilms' Tumor Gene (WT1) Competes With Differentiation-Inducing Signal in Hematopoietic Progenitor Cells" Blood, 91:2969-2976.
Irie, A et al. (Aug. 2012) "Establishment of HLA-DR4 transgenic mice having antigen-presenting function to HLA-DR4-restricted CD4+ Th cell" MHC (Major Histocompatibility Complex). Official Journal of the Japanese Society for Histocompatibility and Immunogenetics, 19(2):94, Abstract O-36(P-80) Japanese with English translation.
Janeway, C.A. et al. (2001) "Chapter 3: Antigen Recognition by B-Cell and T-Cell Receptors" in Immunobiology, 5th Ed., New York; Garland Science, 116-117.
Karin, N. et al. (Dec. 1994) "Reversal of experimental autoimmune encephalomyelitis by a soluble peptide variant of a myelin basic protein epitope: T cell receptor antagonism and reduction of interferon gamma and tumor necrosis factor alpha production" J Exp Med. 1;180(6):2227-2237.
Klebanoff C.A. et al. (2011) "Therapeutic cancer vaccines: are we there yet?" Immunological Reviews, 239:27-44.
Lee, K.H. et al., (1999) "Increased Vaccine-Specific T Cell Frequency After Peptide-Based Vaccination Correlates with Increased Susceptibility to In Vitro Stimulation But Does Not Lead to Tumor Regression" The Journal of Immunology; 163 (11) 6292-6300.

(56) References Cited

OTHER PUBLICATIONS

Lehe, C. et al. (2008) "The Wilms' Tumor Antigen Is a Novel Target for Human CD4+ Regulatory T Cells: Implications for Immunotherapy" Cancer Res, 68(15): 6350-6359.

Marchand, M. et al. (1999) "Tumor regressions observed in patients with metastatic melanoma treated with an antigenic peptide encoded by gene MAGE-3 and presented by HLA-A1" International Journal of Cancer, 80:219-230.

Marchand, M. et al. (2001) "Biological and clinical developments in melanoma vaccines" Expert Opinion on Biological Therapy, 1(3)497-510.

Marsh, S.G.E. et al. (2000) "The HLA Facts Book" Academic Press, England; pp. 299 and 377.

Master, P.S. et at. (1991) "Patterns of Membrane Antigen Expression by AML Blasts: Quantitation and Histogram Analysis" Leukemia and Lymphoma, 5:317-325.

May R.J. et al. (2007) "Peptide Epitopes from the Wilms' Tumor 1 Oncoprotein Stimulate CD4+ and CD8+ T Cells That Recognize and Kill Human Malignant Mesothelioma Tumor Cells" Clin Cancer Res, 13(15):4547-4555, 5226.

Megiorni, F. and A. Pizzuti (2012) "HLA-DQA1 and HLA-DQB1 in Celiac disease predisposition: practical implications of the HLA molecular typing" J. Biomed. Sci., 19:88.

Müller, L. et al. (2003) "Synthetic peptides derived from the Wilms' tumor 1 protein sensitize human t lymphocytes to recognize chronic myelogenous leukemia cells", Hematology Journal, Mcmillan, Basingstoke, GB, 4(1):57-66.

Mustafa, A.S. and T. Godal (1987) "BCG induced CD4+ cytotoxic T cells from BCG vaccinated healthy subjects: relation between cytotoxicity and suppression in vitro" Clin. Exp. Jmmunol., 69:255-262.

Naylor, P.H. et al. (2011) "Peptide Based Vaccine Approaches for Cancer—A Novel Approach Using a WT-1 Synthetic Long Peptide and the IRX-2 Immunomodulatory Regimen" Cancers, 3(4): 3991-4009.

Oka, Y, et al. (Feb. 2000) "Human cytotoxic T-lymphocyte responses specific for peptides of the wild-type Wilms' tumor gene (WT1) product" Immunogenetics, 51:99-107.

Patel S.D. et al. (1997) "Identification of immunodominant T cell epitopes of human glutamic acid decarboxylase 65 by using HLA-DR (alpha1*0101, beta1*0401) transgenic mice", Proc. Natl. Acad. Sci. USA, 94:8082-8087.

Rezvani, K. et al. (2005) "T-Cell Responses Directed against Multiple HLA-A*0201-Restricted Epitopes Derived from Wilms' Tumor 1 Protein in Patients with Leukemia and Healthy Donors: Identification, Quantification, and Characterization" Clin. Cancer Res., 11:8799-8807.

Schreiber, T.H. et al. (2010) "Tumor immunogenicity and responsiveness to cancer vaccine therapy: The state of the art" Seminars in Immunology, 22:105-112.

Sogo, Shinji, Study Director, Otsuka Pharmaceutical Co. ltd. "Final Study Report: Cytolytic Activoy of OCV-501 -Specific Th1 Clones" Study No. 035171 Report No. 028745; completed on Mar. 15, 2013 (39 pages).

Sogo, Shinji; Study Director, Otsuka Pharmaceutical Co. Ltd. "Final Study Report: Effect of OVT-101 on the Helper-activity Against WT1-specific CTL From Human Peripheral Blood Mononuclear Cells" Study No. 030697, Report No. 025539; completed on Dec. 9, 2010 (22 pages).

Sugiyama, H. (Sep. 2007) "WT1 Peptide-Based Cancer Immunotherapy" Biotherapy, 21 (5):299-306. Japanese with English abstract on p. 299.

Sugiyama, H. (2012) "WT1-targeting cancer vaccine" Japanese Journal of Clinical Medicine, 70(12):2105-2113. Japanese with English abstract on p. 2105.

Tsuboi A. et al. (May 1999) "Constitutive expression of the Wilms' tumor gene WT1 inhibits the differentiation of myeloid progenitor cells but promotes their proliferation in response to granulocyte-colony stimulating factor (G-CSF)" Leukemia Research, 23:499-505.

Wang, Li-Xin et al. (2007)"Adoptive transfer of tumor-primed, in vitro—activated, CD4 T effector cells (TEs) combined with CD8 TEs provides intratumoral TE proliferation and synergistic antitumor response" Blood, 109: 4865-4872.

Yamagami, T. et al. (May 1996)"Growth inhibition of human leukemic cells by WT1 (Wilms tumor gene) antisense oligodeoxynucleotides: Implications for the involvement of WT1 in leukemogenesis" Blood, 87(7):2878-84.

Yang, K. L. et al. (2010) "An HLA-A*02:01-B*13:01-DRB1*14:01:03 haplotype conserved in Taiwanese and a possible close relationship between DRB1*14:01:03 and DRB1*14:54" Intl. J. Immunogenetics, 38:69-71.

Yazawa, T. et al. (1999) "Lack of class II transactivator causes severe deficiency of HLA-DR expression in small cell lung cancer" J. Palhol., 187:191-199.

Office Action dated Feb. 26, 2018, issued in the corresponding Mexican Patent Application No. MX/A/2013/003884 with English translation.

Office Action dated Jan. 24, 2018, issued in the corresponding Russian Patent Application No. 2014104572/10, with English translation.

Lee K.H. et, al. "The Journal of Immunology", Dec. 1, 1999, 163 (11) 6292-6300.

* cited by examiner

SEQUENCE LISTING

```
<160> NUMBER OF SEQ ID NOS: 56

<210> SEQ ID NO 1
<211> LENGTH: 449
<212> TYPE: PRT
<213> ORGANISM: Homo sapiens

<400> SEQUENCE: 1
```

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile

```
            130                 135                 140
Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                    165                 170                 175

Lys His Glu Asp Pro Met Gly Gln Gln Gly Ser Leu Gly Glu Gln Gln
                180                 185                 190

Tyr Ser Val Pro Pro Val Tyr Gly Cys His Thr Pro Thr Asp Ser
            195                 200                 205

Cys Thr Gly Ser Gln Ala Leu Leu Leu Arg Thr Pro Tyr Ser Ser Asp
        210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Gly Ser Ser Ser
                245                 250                 255

Ser Val Lys Trp Thr Glu Gly Gln Ser Asn His Ser Thr Gly Tyr Glu
                260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Arg Val Pro
        290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
                340                 345                 350

Tyr Gln Cys Asp Phe Lys Asp Cys Glu Arg Arg Phe Ser Arg Ser Asp
            355                 360                 365

Gln Leu Lys Arg His Gln Arg Arg His Thr Gly Val Lys Pro Phe Gln
        370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
                420                 425                 430

Arg His His Asn Met His Gln Arg Asn Met Thr Lys Leu Gln Leu Ala
            435                 440                 445

Leu

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

Leu Val Arg His His Asn Met His Gln
1               5

<210> SEQ ID NO 3
<211> LENGTH: 9
<212> TYPE: PRT
<213> ORGANISM: Artificial Sequence
```

```
<220> FEATURE:
<223> OTHER INFORMATION: Synthetic Peptide

<400> SEQUENCE: 3

Leu Tyr Gln Met Thr Ser Gln Leu Glu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 4

Phe Lys His Glu Asp Pro Met Gly Gln
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Leu Val Arg Ser Ala Ser Glu Thr Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 6

Met Gly Gln Gln Gly Ser Leu Gly Glu
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 7

Val Tyr Gly Cys His Thr Pro Thr Asp
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 8

Leu Arg Thr Pro Tyr Ser Ser Asp Asn
1               5

<210> SEQ ID NO 9
<211> LENGTH: 9
<212> TYPE: PRT
<213> ORGANISM: Artificial Sequence
<220> FEATURE:
```

```
<223> OTHER INFORMATION: Synthetic Peptide

<400> SEQUENCE: 9

Phe Ile Lys Gln Glu Pro Ser Trp Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 10

Trp Gly Gly Ala Glu Pro His Glu Glu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 11

Phe Lys Leu Ser His Leu Gln Met His
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 12

Tyr Phe Lys Leu Ser His Leu Gln Met
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 13

Leu Glu Cys Met Thr Trp Asn Gln Met
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 14

Phe Arg Gly Ile Gln Asp Val Arg Arg
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Peptide
```

<400> SEQUENCE: 15

Leu Leu Pro Ala Val Pro Ser Leu Gly
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 16

Leu Ser Ala Phe Thr Val His Phe Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 17

Met Asn Leu Gly Ala Thr Leu Lys Gly
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 18

Val Arg Ser Ala Ser Glu Thr Ser Glu
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 19

Leu Pro Ala Val Pro Ser Leu Gly Gly
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 20

Tyr Gly Cys His Thr Pro Thr Asp Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Peptide

```
<400> SEQUENCE: 21

Phe Ser Gly Gln Phe Thr Gly Thr Ala
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 22

Phe Met Cys Ala Tyr Pro Gly Cys Asn
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 23

Tyr Gln Met Thr Ser Gln Leu Glu Cys
1               5

<210> SEQ ID NO 24
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 24

Lys Arg Tyr Phe Lys Leu Ser His Leu Gln Met His Ser Arg Lys His
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 25

Pro Asn His Ser Phe Lys His Glu Asp Pro Met Gly Gln Gln Gly
1               5                   10                  15

<210> SEQ ID NO 26
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 26

Asn Leu Tyr Gln Met Thr Ser Gln Leu Glu Cys Met Thr Trp Asn Gln
1               5                   10                  15

Met Asn Leu

<210> SEQ ID NO 27
<211> LENGTH: 9
<212> TYPE: PRT
<213> ORGANISM: Artificial Sequence
<220> FEATURE:
<223> OTHER INFORMATION: Synthetic Peptide
```

<400> SEQUENCE: 27

Cys Met Thr Trp Asn Gln Met Asn Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 28

Cys Tyr Thr Trp Asn Gln Met Asn Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 29

Arg Met Phe Pro Asn Ala Pro Tyr Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 30

Arg Tyr Pro Ser Cys Gln Lys Lys Phe
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 31

Ala Tyr Thr Trp Asn Gln Met Asn Leu
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 32

Ala Tyr Thr Trp Asn Gln Met Asn Leu
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Peptide
<220> FEATURE:

<221> NAME/KEY: MISC_FEATURE
<222> LOCATION: (1)..(1)
<223> OTHER INFORMATION: Xaa = Abu
<220> FEATURE:
<221> NAME/KEY: MISC_FEATURE
<222> LOCATION: (1)..(1)
<223> OTHER INFORMATION: Xaa is Abu

<400> SEQUENCE: 33

Xaa Tyr Thr Trp Asn Gln Met Asn Leu
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 34

Arg Tyr Thr Trp Asn Gln Met Asn Leu
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 35

Lys Tyr Thr Trp Asn Gln Met Asn Leu
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 36

Arg Tyr Phe Pro Asn Ala Pro Tyr Leu
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 37

Arg Tyr Pro Gly Val Val Pro Thr Leu
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 38

Ala Tyr Leu Pro Ala Val Pro Ser Leu
1               5

```
<210> SEQ ID NO 39
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 39

Asn Tyr Met Asn Leu Gly Ala Thr Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 40

Arg Val Pro Gly Val Ala Pro Thr Leu
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 41

Arg Tyr Pro Ser Ser Gln Lys Lys Phe
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 42

Arg Tyr Pro Ser Ala Gln Lys Lys Phe
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: Xaa = Abu
<220> FEATURE:
<221> NAME/KEY: MISC_FEATURE
<222> LOCATION: (5)..(5)
<223> OTHER INFORMATION: Xaa is  Abu

<400> SEQUENCE: 43

Arg Tyr Pro Ser Xaa Gln Lys Lys Phe
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Peptide
```

<400> SEQUENCE: 44

Ser Leu Gly Glu Gln Gln Tyr Ser Val
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 45

Asp Leu Asn Ala Leu Leu Pro Ala Val
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 46

Tyr Arg Ile His Thr His Gly Val Phe
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 47

Leu Val Arg His His Asn Met His Gln
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 48

Tyr Gln Met Thr Ser Gln Leu Gly Cys
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 49

Leu Gln Met His Ser Arg Lys His Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic Peptide

```
<400> SEQUENCE: 50

Tyr Phe Lys Leu Ser His Leu Gln Met
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 51

Val Lys Pro Phe Gln Cys Lys Thr Cys
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 52

Leu Lys Arg His Gln Arg Arg His Thr
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 53

Leu Lys Thr His Thr Arg Thr His Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 54

Tyr Gly Pro Phe Gly Pro Pro Pro Pro
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 55

Val Arg His His Asn Met His Gln Arg
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 56
```

```
Phe Pro Asn Ala Pro Tyr Leu Pro Ser
1               5
```

HLA-DR-BINDING ANTIGEN PEPTIDE DERIVED FROM WT1

CROSS-REFERENCE TO RELATED APPLICATIONS

The present application is a division of U.S. Ser. No. 10/578,183, filed Feb. 27, 2007, which is a National Stage (371) of PCT/JP04/16336, filed Nov. 4, 2004, and claims priority to JP 2003-375603, filed Nov. 15, 2003.

TECHNICAL FIELD

The present invention relates to HLA-DRB1*0405-binding antigen peptides derived from WT1.

BACKGROUND ART

WT1 gene (Wilms' tumor gene 1) has been identified as one of causative genes of Wilms' tumor that is a childhood renal tumor (*Cell* 60: 509, 1990, *Nature* 343: 774, 1990). WT1 gene encodes the transcription factor WT1 which plays an important role in many processes such as proliferation, differentiation and apoptosis of cells, and development of tissues (*Int. Rev. Cytol.* 181: 151, 1998). WT1 gene was originally defined as a tumor suppressor gene. However, subsequent studies revealed that WT1 gene is highly expressed in leukemia and various solid cancers including lung cancer and breast cancer, indicating that WT1 gene rather exerts an oncogenic function that promotes cancer growth. In addition, it was demonstrated that, when peripheral blood mononuclear cells positive for HLA-A*0201 or HLA-A*2402 were stimulated in vitro with WT1-derived peptides, peptide-specific cytotoxic T-lymphocytes (CTLs) were induced and killed leukemic or solid tumor cells which endogenously express WT1. These results demonstrated that WT1 is a promising target molecule of cancer immunotherapy (*Int. J. Hematol* 76: 127, 2002).

It has been reported that presence of helper T cells specific to cancer antigen is essential for effective induction of CTLs (*Cancer. Res.* 62: 6438, 2002).

Helper T cells (CD4-positive T cells) are induced (made proliferate) and activated when they recognize a complex of MHC class II molecule and antigen peptide on antigen-presenting cells. The activated helper T cells produce cytokines such as IL-2, IL-4, IL-5, IL-6, and/or interferons and mediate the growth, differentiation, and maturation of B cells. The activated helper T cells also function to promote the growth, differentiation or maturation of other subsets of T cells such as Tc and TD cells. Thus, the activated helper T cells can activate the immune system through the promotion of growth and activation of B and T cells. Therefore, it was suggested to be helpful to enhance functions of helper T cells being under the influence of MHC-class II-binding antigen peptide (also referred to as "helper peptide"), whereby efficacy (potency) of cancer vaccine in cancer immunotherapy (cancer vaccine therapy) is increased (*J. Immunother.*, 24:195, 2001).

As for WT1-derived peptides, only one antigen peptide is known to bind to a subtype of MHC class II molecule, i.e., HLA-DRB1*0401 (*Cancer Immunol. Immunother.* 51:271, 2002). There are no WT1-derived peptides which have been reported to bind to different subtypes.

DISCLOSURE OF INVENTION

The purpose of the present invention is to provide HLA-DRB1*0405-binding antigen peptides derived from WT1, and use of the peptide as an enhancer of cancer vaccine efficacy (an agent for enhancing efficacy of cancer vaccine).

The present inventor has conducted intensive study on WT1-derived antigen peptides ("helper peptides") having an activity of binding to MHC class II antigen and enhancing the cancer vaccine efficacy (potency) in cancer immunotherapy. In consequence, the present inventor has for the first time found that WT1 contains an antigen peptide portion(s) which has an activity of binding to HLA-DRB1*0405 among a number of MHC class II subclasses and inducing helper T cells. This finding led to the development of a novel therapeutic method by which WT1-specific helper T cells are induced and enhanced in HLA-DRB1*0405-positive cancer patients.

Recent researches revealed that there exists promiscuous helper peptides which are helper peptides capable of binding to plural HLA-class II molecules and inducing helper CD4-positive T cells (*British J. cancer*, 85(10), p 1527-1534 (2001); *J. Immunol.*, 169, p 557-565 (2002)). The present inventor made investigation into $WT1_{332-347}$, which is one of the above-described HLA-DRB1*0405-binding antigen peptides (helper peptides), to elucidate whether or not it is potentially a promiscuous helper peptide. As a result, said peptide proved to be a promiscuous helper peptide that binds not only to HLA-DRB1*0405 molecule but also to HLA-DRB1*1502. Thus, the $WT1_{332-347}$ peptide of the present invention is a helper peptide applicable to patients having HLA-DRB1*1502 as well as those having HLA-DRB1*0405. The present inventor also found that WT1 contains an antigen peptide portion(s) capable of binding to HLA-DRB1*1502, one of a number of MHC class II subclasses, and inducing helper T cells for the first time.

The present invention has been established on the basis of these findings.

The present invention encompasses the followings.

(1) A peptide consisting of 10-25 contiguous amino acids in the amino acid sequence of human WT1 shown in SEQ ID NO: 1, which binds to HLA-DRB1*0405 and induces helper T cells.

(2) The peptide of (1) above, which comprises an amino acid sequence set forth in any one of SEQ ID NOS: 2-23.

(3) The peptide of (2) above, which comprises the amino acid sequence set forth in SEQ ID NO: 24.

(4) A peptide of 10-25 amino acids, which comprises an amino acid sequence wherein the amino acid residue at position 1, 4, 6 and/or 9 of an amino acid sequence set forth in any one of SEQ ID NOS: 2-23 is substituted by another amino acid residue, and which binds to an HLA-DRB1*0405 and induces helper T cells.

(5) The peptide of (4) above, which comprises an amino acid sequence wherein the amino acid residue at position 1, 4, 6 and/or 9 of an amino acid sequence set forth in any one of SEQ ID NOS: 2-23 is substituted by an amino acid residue selected from the following amino acids:
phenylalanine, tyrosine, tryptophan, valine, isoleucine, leucine and methionine for the position 1;
valine, isoleucine, leucine, methionine, aspartic acid and glutamic acid for the position 4;
asparagine, serine, threonine, glutamine, lysine and aspartic acid for the position 6; and
aspartic acid, glutamic acid and glutamine for the position 9.

(6) The peptide of (5) above, which comprises an amino acid sequence wherein the amino acid residue at position 3, 6, 8 and/or 11 of the amino acid sequence set forth in SEQ ID NO: 24 is substituted by an amino acid residue selected from the following amino acids:

phenylalanine, tryptophan, valine, isoleucine, leucine and methionine for the position 3;
valine, isoleucine, methionine, aspartic acid and glutamic acid for the position 6;
asparagine, serine, threonine, glutamine, lysine and aspartic acid for the position 8; and
aspartic acid, glutamic acid and glutamine for the position 11.

(7) A peptide consisting of 10-25 contiguous amino acids in the amino acid sequence of human WT1 shown in SEQ ID NO: 1, which binds to HLA-DRB1*1502 and induces helper T cells.

(8) The peptide of (7) above, which comprises an amino acid sequence set forth in any one of SEQ ID NOS: 46-56.

(9) The peptide of (7) above, which comprises the amino acid sequence set forth in SEQ ID NO: 24.

(10) A peptide comprising a peptide described in any one of (1) to (9) above together with a cancer antigen peptide.

(11) A polynucleotide encoding a peptide described in any one of (1) to (10) above.

(12) An expression vector containing the polynucleotide described in (11) above.

(13) A cell containing the expression vector described in (12) above.

(14) A process for producing a peptide described in any one of (1) to (10) above, which comprises culturing the cell described in (13) above under the condition where the peptide can be expressed.

(15) An antibody which specifically binds to a peptide described in any one of (1) to (9) above.

(16) A pharmaceutical composition which comprises a peptide described in any one of (1) to (10) above, an expression vector described in (12) above or a cell described in (13) above, in association with a pharmaceutically acceptable carrier.

(17) The pharmaceutical composition of (16) above, which is a therapeutic or preventive agent for cancer.

(18) The pharmaceutical composition of (16) above, which is an inducer of helper T cells, and which comprises a peptide described in any one of (1) to (9) above; an expression vector described in (12) related to a peptide of any one of (1) to (9) above; or a cell described in (13) above related to a peptide of any one of (1) to (9) above, in association with a pharmaceutically acceptable carrier.

(19) The pharmaceutical composition of (16) above, which is an enhancer of cancer vaccine efficacy, and which comprises a peptide described in any one of (1) to (9) above; an expression vector described in (12) related to a peptide of any one of (1) to (9) above; or a cell described in (13) above related to a peptide of any one of (1) to (9) above, in association with a pharmaceutically acceptable carrier.

(20) The pharmaceutical composition of (16) above, which is a therapeutic or preventive agent for cancer, and which comprises a peptide described in (10) above; an expression vector described in (12) related to a peptide of (10) above; or a cell described in (13) above related to a peptide of (10) above, in association with a pharmaceutically acceptable carrier.

(21) Use of a peptide described in any one of (1) to (10) above, an expression vector described in (12) above or a cell described in (13) above for the manufacture of a therapeutic or preventive agent for cancer.

(22) A method of treating or preventing cancer, which comprises administering a peptide described in any one of (1) to (10) above, an expression vector described in (12) above or a cell described in (13) above to a subject in need thereof.

(23) A pharmaceutical composition which comprises a peptide described in any one of (1) to (9) above in combination with a cancer antigen peptide.

(24) The pharmaceutical composition of (23) above, which is used for treating or preventing cancer.

(25) A kit for treating or preventing cancer, which comprises a pharmaceutical composition comprising a peptide of any one of (1) to (9) above in association with a pharmaceutically acceptable carrier, and a pharmaceutical composition comprising a cancer antigen peptide in association with a pharmaceutically acceptable carrier.

(26) Use of a peptide of any one of (1) to (9) above in combination with a cancer antigen peptide in the manufacture of a therapeutic or preventive agent for cancer.

(27) A method of treating or preventing cancer, which comprises administering a peptide of any one of (1) to (9) above in combination with a cancer antigen peptide to a subject in need thereof.

The present invention provides an HLA-DRB1*0405-binding antigen peptide derived from WT1, a polynucleotide encoding the peptide, an inducer of helper T cells ("helper T cell inducer") comprising said peptide or polynucleotide, and the like. The helper T cell inducer of the present invention is useful as an enhancer of cancer vaccine efficacy. The enhancer of cancer vaccine efficacy of the present invention is applicable to many HLA-DRB1*0405-positive patients, and is particularly useful for enhancing efficacy of WT1 vaccine.

BRIEF DESCRIPTION OF DRAWINGS

FIG. 15 shows the results of examination into the responsiveness of E15.1 cell line or E15.2 cell line to autologous PBMCs pulsed with WT1-derived $WT1_{332-347}$ peptide. In the figure, "-" represents the results obtained by using autologous PBMCs not pulsed with a peptide, and "332" the results obtained using autologous PBMCs pulsed with $WT1_{332-347}$ peptide. The vertical axis indicates the amount of [$^3$H]-thymidine uptake (cpm) by separated cell lines.

BEST MODE FOR CARRYING OUT THE INVENTION

Figure 1:
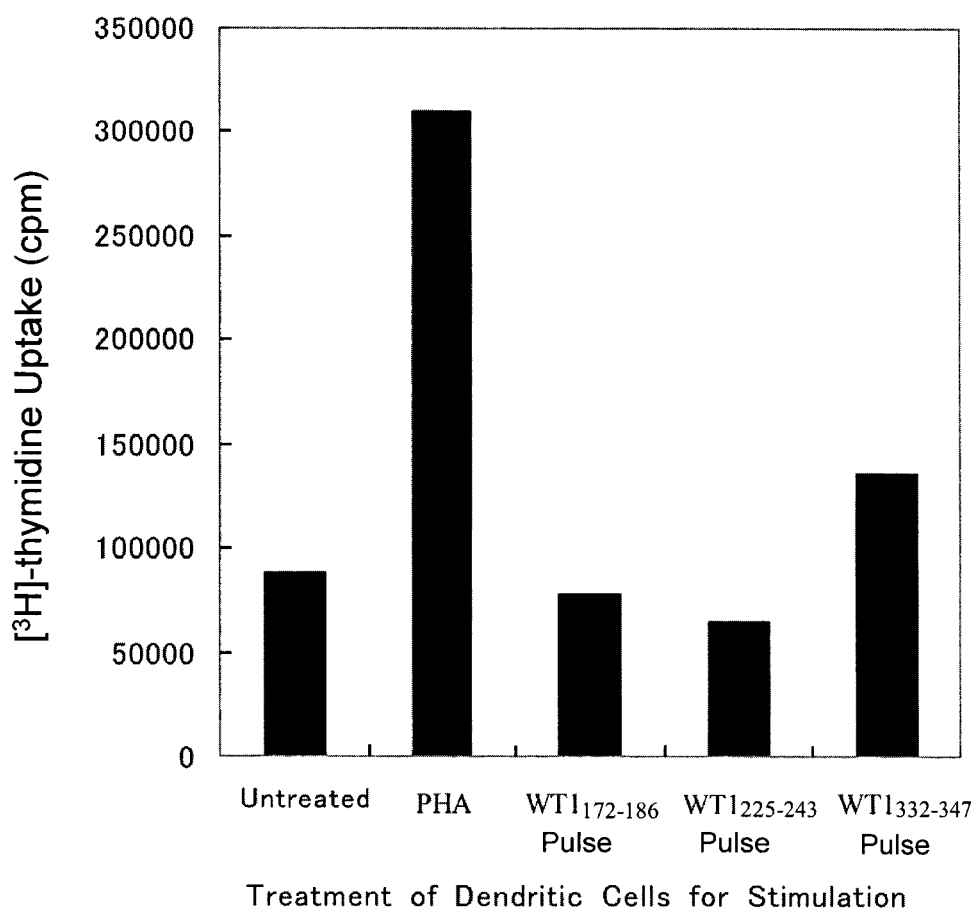
FIG. 1 shows the results of examination into responsiveness of CD4-positive T cells (helper T cells) stimulated with a WT1-derived $WT1_{332-347}$ peptide to various dendritic cells. In the figure, "Untreated" represents the responsiveness to dendritic cells not pulsed with a peptide; "PHA" the results of examination wherein CD4 positive T cells were treated with PHA instead of dendritic cells, "$WT1_{172-186}$ pulse" the responsiveness to dendritic cells pulsed with $WT1_{172-186}$ peptide, "$WT1_{225-243}$ pulse" the responsiveness to dendritic cells pulsed with $WT1_{225-243}$ peptide, and "$WT1_{332-347}$ pulse" the responsiveness to dendritic cells pulsed with "$WT1_{332-347}$ peptide. The vertical axis indicates the amount of [$^3$H]-thymidine uptake (cpm) by CD4-positive T cells.

The present invention provides a peptide consisting of 10-25 contiguous amino acids in the amino acid sequence of human WT1 set forth in SEQ ID NO: 1, said peptide binding to HLA-DRB1*0405 and inducing helper T cells. The present invention encompasses peptides wherein the N-terminal and/or C-terminal amino acid residue is modified or those wherein a particular amino acid residue(s) is altered.

Hereinafter, "a peptide that induces helper T cells (or a peptide that induces CD4-positive T cells)" may be referred to as "a helper peptide".

The amino acid sequence of human WT1 set forth in SEQ ID NO: 1 is a known sequence as described in *Cell*, 60:509, 1990, and NCBI data base (Accession Nos. XP_034418 and P19544).

The peptide of the present invention is a partial peptide which consists of 10-25 contiguous amino acids present in the amino acid sequence of human WT1 set forth in SEQ ID NO: 1. The definition of "10-25 amino acids" is based on the facts that peptides having an activity of binding to MHC class II generally consist of 10 to 25 amino acids (*Immunogenetics*, 41: 178-228, 1995, *Biochimica et Biophysica Acta* 1316, 85-101 (1996), *Immunology*, 96, 1-9 (1999), *Peptides*, Vol. 19, 179-198 (1998), *Immunobiology*, 5th Edt., 116-117, Garland Publishing (2001)). Preferred peptides are those consisting of 13-17 contiguous amino acids in the amino acid sequence of human WT1.

The peptide of the present invention can be identified by synthesizing a peptide (candidate peptide) consisting of 10-25 contiguous amino acids in the amino acid sequence set forth in SEQ ID NO: 1, and assaying whether or not the peptide is capable of binding to HLA-DRB1*0405 and inducing helper T cells.

The synthesis of a peptide can be conducted according to processes generally used in the field of peptide chemistry. Such a method can be found in literatures including *Peptide Synthesis*, Interscience, New York, 1966; *The Proteins*, Vol. 2, Academic Press Inc., New York, 1976; *Peptide Synthesis*, Maruzen, Inc., 1975; *Peptide-Gosei no Kiso to Jikken*, Maruzen, Inc., 1985; and *Iyakuhin no Kaihatsu* (Zoku), Vol. 14, Peptide Synthesis, Hirokawa-syoten, 1991.

It can be examined whether or not a candidate peptide binds to HLA-DRB1*0405 and induces helper T cells using a method described in, for example, *Cancer. Immunol. Immunother.* 51: 271 (2002), the method described in the working Examples, or the method described just below.

Specifically, dendritic cells (adherent cells) are prepared by isolating peripheral blood mononuclear cells (PBMCs) from a human subject positive for HLA-DRB1*0405, and removing non-adherent cells. Separately, helper T cells (CD4-positive T cells) are prepared from the same HLA-DRB1*0405-positive subject by density gradient centrifugation with Ficoll-Paque, and so on.

The above-described dendritic cells are cultured after addition of a candidate peptide, and further cultured with the above-described helper T cells. The helper T cells are then recovered and stimulated several times with dendritic cells pulsed with the candidate peptide in a similar manner. It is possible to evaluate whether or not helper T cells are induced (activated) in response to stimulation with a peptide by measuring, for example, (1) growth activity of helper T cells or (2) cytokine-producing-activity of helper T cells. Specifically, the growth activity (1) can be examined by measuring the amount of [$^3$H]-thymidine uptake by helper T cells. The cytokine-producing activity (2) can be examined by measuring the amount of cytokine such as IFN-γ produced by activated helper T cells by enzyme enzyme-linked immunosorbent assay (ELISA) or the like.

The amino acid sequence of antigen peptides binding to MHC class I or MHC class II molecule and being presented obeys a certain rule (binding motif). There are terminal amino acid residues at the both ends of peptides binding to MHC class I molecule which play a significant role in the binding with MHC class I molecule; however, there are no such amino acids at either end of peptides binding to MHC class II molecule, and the terminal amino acids do not bind to MHC class II molecule. Such a peptide rather is accommodated and immobilized (fixed) in a peptide-binding groove longitudinally. The immobilization of a peptide in a peptide-binding groove can be achieved through the binding of the side chains of amino acids constituting the peptide to the peptide-binding groove and the binding of the main chain of the peptide to the side chains of amino acids well-preserved in the entire peptide-binding groove for MHC class II molecules. A peptide-binding groove has small or large pockets and there is amino acid polymorphism in the amino acid residues constituting the pockets depending on the MHC class II molecule.

X-ray crystallography obtained so far revealed that side chains of amino acid residues at positions 1, 4, 6 and 9 of the smallest MHC class II-binding peptide engage with these binding pockets.

The amino acid motif of peptides binding to a pocket(s) of peptide-binding groove can be estimated by analyzing the pattern of amino acid residues commonly found in the binding peptides for respective MHC class II molecules originated in different alleles. It is considered that, because peptides of about 9 amino acids having such a motif is accommodated in the peptide-binding groove in such a manner that the both termini protrude from the both sites of groove, there are basically no limitations regarding the length of peptides which can bind to MHC class II molecules. However, in many cases, a long peptide is cleaved into peptides of 13-17 amino acid length by peptidases (*Immunobiology*, 5th Edt., 116-117, Garland Publishing (2001)).

Regarding the peptide which has the binding activity for HLA-DRB1*0405, the amino acids at positions 1, 4, 6 and 9 in the HLA(MHC)-binding domain consisting of 9-amino acids are expected to have the following regularities (motifs) (*Immunogenetics*, 41, 178-228 (1995), *Biochimica et Biophysica Acta* 1316, 85-101 (1996)).

Position 1: phenylalanine (F), tyrosine (Y), tryptophan (W), valine (V), isoleucine (I), leucine (L) and methionine (M)
Position 4: valine (V), isoleucine (I), leucine (L), methionine (M), aspartic acid (D) and glutamic acid (E)
Position 6: asparagine (N), serine (S), threonine (T), glutamine (Q), lysine (K) and aspartic acid (D)
Position 9: aspartic acid (D), glutamic acid (E) and glutamine (Q)

Recently, it has become possible to search for peptide sequences expected to bind to MHC class II antigen using software for predicting MHC class II binding peptides (Propred, *Bioinformatics* 17: 1236, 2001).

The present invention is based on the finding that WT1 (SEQ ID NO: 1) contains antigen peptide portions which bind to HLA-DRB1*0405 (a kind of MHC class II) and induce helper T cells for the first time. Examples of putative HLA-DRB1*0405-binding 9-amino-acid portions in the amino acid sequence of said WT1 include the 9-amino-acid portions derived from WT1 as shown in SEQ ID NOS: 2-23. Thus, as a specific embodiment of the peptide of the present invention, the present invention provides a peptide which comprises an amino acid sequence set forth in any one of SEQ ID NOS: 2-23, and which binds to HLA-DRB1*0405 and induces helper T cells.

There are no limitations regarding the length of such a peptide on the condition that said peptide is a partial peptide of WT1 and comprises an amino acid sequence set forth in any one of SEQ ID NOS: 2-23, and has an activity of binding to HLA-DRB1*0405 and inducing helper T cells. As mentioned above, a peptide of about 9 amino acids with a binding motif can accommodate in a peptide-binding groove with the both ends extruding from the both sites of groove, and hence there are essentially no limitations regarding the length of the peptides capable of binding to MHC class II molecule. However, long peptides are generally cleaved by peptidases, and the MHC class II-binding peptides having been reported so far are about 10-25 amino acids in length (*Immunogenetics*, 41, 178-228 (1995), *Biochimica et Biophysica Acta* 1316, 85-101 (1996), *Immunology*, 96, 1-9 (1999), *Peptides*, Vol. 19, 179-198 (1998), *immunobiology*, 5th Edt., 116-117, Garland Publishing (2001)). Taking this into account, the peptides of the present invention preferably consist of about 10-25 amino acids, and more preferably about 13-17 amino acids.

Accordingly, examples of a preferred embodiment of the peptide of the present invention which comprises an amino acid sequence set forth in any one of SEQ ID NOS: 2-23 include partial peptides derived from WT1 consisting of 10-25 amino acids (preferably, 13-17 amino-acids), which comprise an amino acid sequence set forth in any one of SEQ ID NOS: 2-23, and which have an activity of binding to HLA-DRB1*0405 and inducing helper T cells.

Examples of more preferred embodiments include partial peptides derived from WT1 consisting of 10-25 amino acids (preferably, 13-17 amino-acids), which comprise an amino acid sequence set forth in SEQ ID NO: 12, and which have an activity of binding to HLA-DRB1*0405 and inducing helper T cells. Examples of still more preferred embodiments include partial peptides derived from WT1 consisting of 16-25 amino acids (preferably, 16-17 amino-acids), which comprise the amino acid sequence set forth in SEQ ID NO: 24, and which have an activity of binding to HLA-DRB1*0405 and inducing helper T cells. The amino acid sequence set forth in SEQ ID NO: 24 represents a 16-amino-acid partial peptide derived from WT1 and includes the amino acid sequence set fort in SEQ ID NO: 12.

Further preferred embodiment is the peptide consisting of the amino acid sequence set forth in SEQ ID NO: 24.

The peptides of the present invention may be altered as appropriate within a range that the activity is maintained. As used herein the "alteration" of amino acid residue means substitution, deletion and/or addition of amino acid residue(s) (the addition is inclusive of addition of amino acid(s) at the N- and/or C-terminus of a peptide). The substitution of amino acid residue(s) is preferred. When the alteration involves substitution of an amino acid residue(s), any number of amino acid residues at any position can be replaced on the condition that the activity as a helper peptide is retained. However, since a peptide which binds to HLA class II molecule is generally about 10-25 amino acids in length, the alteration is preferably involves one to several amino acids.

When altering amino acid residue by substitution, it is preferred that the amino acid residue at position 1, 4, 6 and/or 9 of a 9 amino acid peptide having the structure for the binding motif of HLA-DRB1*0405 is substituted.

Specific examples of substitution-related peptides of the present invention include peptides of 10-25 amino acids, which comprise an amino acid sequence wherein the amino acid residue at position 1, 4, 6 and/or 9 of an amino acid sequence set forth in any one of SEQ ID NOS: 2-23 is substituted by another amino acid residue, and which bind to an HLA-DRB1*0405 and induce helper T cells.

Preferred examples include peptides of 10-25 amino acids, which comprise an amino acid sequence wherein the amino acid residue at position 1, 4, 6 and/or 9 of an amino acid sequence set forth in any one of SEQ ID NOS: 2-23 is substituted by an amino acid residue selected from the following amino acids:
phenylalanine, tyrosine, tryptophan, valine, isoleucine, leucine and methionine for the position 1;
valine, isoleucine, leucine, methionine, aspartic acid and glutamic acid for the position 4;
asparagine, serine, threonine, glutamine, lysine and aspartic acid for the position 6; and
aspartic acid, glutamic acid and glutamine for the position 9, and which bind to an HLA-DRB1*0405 and induce helper T cells.

For example, the substitution of amino acid residue at position 1, 4, 6 and/or 9 can be conducted for the purpose of improving the binding activity to HLA-DRB1*0405 or enhancing the activity of the above-mentioned natural-type helper peptides of the present invention which consist of partial sequences of WT1. The parts other than the substituted amino acid at position 1, 4, 6 and/or 9 of a peptide may remain to have the natural-type sequence (i.e., being kept to have the partial sequence of WT1), or may be further altered as far as the activity is retained.

More preferred examples include peptides of 10-25 amino acids, which comprise an amino acid sequence wherein the amino acid residue at position 1, 4, 6 and/or 9 of the amino acid sequence set forth in SEQ ID NO: 12 is substituted by an amino acid residue selected from the following amino acids:

phenylalanine, tryptophan, valine, isoleucine, leucine and methionine for the position 1;
valine, isoleucine, methionine, aspartic acid and glutamic acid for the position 4;
asparagine, serine, threonine, glutamine, lysine and aspartic acid for the position 6; and
aspartic acid, glutamic acid and glutamine for the position 9, and which bind to an HLA-DRB1*0405 and induce helper T cells.

Still more preferred examples include peptides wherein the amino acid residue at position 3, 6, 8 and/or 11 of the 16-amino-acid partial peptide derived from WT1 set forth in SEQ ID NO: 24, which comprises the amino acid sequence set forth in SEQ ID NO: 12, is substituted by an amino acid residue selected from the following amino acids:
phenylalanine, tryptophan, valine, isoleucine, leucine and methionine for the position 3;
valine, isoleucine, methionine, aspartic acid and glutamic acid for the position 6;
asparagine, serine, threonine, glutamine, lysine and aspartic acid for the position 8; and
aspartic acid, glutamic acid and glutamine for the position 11. Preferred examples may include peptides of 16-25 amino acids comprising the altered amino acid sequence derived from SEQ ID NO: 24.

The present invention also provides a peptide (so-called an epitope peptide) comprising a helper peptide (natural- or altered-peptide) of the present invention together with a cancer antigen peptide.

Recently, it has been reported that an epitope peptide wherein a cancer antigen peptide(s) (also called as "CTL epitope") and a helper peptide(s) (also called as "helper epitope") are linked together can induce CTLs efficiently. That is, helper T cells (CD4-positive T cells) activated by a helper peptide exert various activities including induction of differentiation and maintenance of CTLs, and activation of effectors such as macrophages, etc, and hence are considered to enhance the CTL-induction by cancer antigens. As a concrete example of a peptide wherein a helper peptide(s) and cancer antigen peptide(s) are linked together, it is reported that a DNA (minigene) encoding an epitope peptide composed of HBV-originated HLA-A2-restricted antigen peptides (6 peptides), HLA-A11-restricted antigen peptides (3 peptides) and a helper peptide induced in vivo CTLs directed to the respective epitopes efficiently (*Journal of Immunology* 1999, 162: 3915-3925). Practically, a peptide wherein a CTL epitope (tumor antigen peptide corresponding to position 280-288 of melanoma antigen gp100) and a helper epitope (tetanus toxin-originated T helper epitope) are linked has been subjected to clinical test (*Clinical Cancer Res.*, 2001, 7:3012-3024).

Accordingly, as a specific embodiment, the peptides of the present invention also include epitope peptides comprising a helper peptide of the present invention and a cancer antigen peptide.

As the cancer antigen peptide, any of known cancer antigen peptides can be used; however, it is preferred to use a cancer antigen peptide derived from WT1 (natural or altered peptide). Concrete examples include WT1-derived peptides restricted to HLA-A1, -A0201, -A0204, -A0205, -A0206, -A0207, -A11, -A24, -A31, -A6801, -B7, -B8, -B2705, -B37, -Cw0401, -Cw0602, and the like.

Examples of WT1-derived cancer antigen peptides include those listed in Table II-Table XLVI of WO2000/18795 and altered peptides thereof which have the activity as a cancer antigen peptide (an activity of binding to an HLA antigen and inducing CTLs).

More concrete examples of WT1-derived cancer antigen peptides include the followings.

```
                                           (SEQ ID NO: 27)
   Cys Met Thr Trp Asn Gln Met Asn Leu (SEQ ID NO: 28)
   Cys Tyr Thr Trp Asn Gln Met Asn Leu (SEQ ID NO: 29)
   Arg Met Phe Pro Asn Ala Pro Tyr Leu (SEQ ID NO: 30)
   Arg Tyr Pro Ser Cys Gln Lys Lys Phe (SEQ ID NO: 31)
   Ser Tyr Thr Trp Asn Gln Met Asn Leu (SEQ ID NO: 32)
   Ala Tyr Thr Trp Asn Gln Met Asn Leu (SEQ ID NO: 33)
   Abu Tyr Thr Trp Asn Gln Met Asn Leu (SEQ ID NO: 34)
   Arg Tyr Thr Trp Asn Gln Met Asn Leu (SEQ ID NO: 35)
   Lys Tyr Thr Trp Asn Gln Met Asn Leu (SEQ ID NO: 36)
   Arg Tyr Phe Pro Asn Ala Pro Tyr Leu (SEQ ID NO: 37)
   Arg Tyr Pro Gly Val Ala Pro Thr Leu (SEQ ID NO: 38)
   Ala Tyr Leu Pro Ala Val Pro Ser Leu (SEQ ID NO: 39)
   Asn Tyr Met Asn Leu Gly Ala Thr Leu (SEQ ID NO: 40)
   Arg Val Pro Gly Val Ala Pro Thr Leu (SEQ ID NO: 41)
   Arg Tyr Pro Ser Ser Gln Lys Lys Phe (SEQ ID NO: 42)
   Arg Tyr Pro Ser Ala Gln Lys Lys Phe (SEQ ID NO: 43)
   Arg Tyr Pro Ser Abu Gln Lys Lys Phe (SEQ ID NO: 44)
   Ser Leu Gly Glu Gln Gln Tyr Ser Val (SEQ ID NO: 45)
   Asp Leu Asn Ala Leu Leu Pro Ala Val
```

In the above, "Abu" refers to "α-aminobutyric acid.

Among them, the peptides set forth in SEQ ID NOS: 27 and 29 are HLA-A24 antigen- and HLA-A2 antigen-binding peptides, and the peptides set forth in SEQ ID NOS: 44 and 45 are HLA-A2 antigen-binding peptides. The other peptides are HLA-A24 antigen-binding peptides.

Preferred cancer antigen peptide is the one set forth in SEQ ID NO: 27, 28, 29, 30, 44 or 45.

More specific examples of epitope peptides of the present invention include those which comprise a helper peptide that is a WT1-derived partial peptide of 10-25 amino acids comprising an amino acid sequence set forth in any one of SEQ ID NOS: 2-23 and has an activity of binding to HLA-DRB1*0405 and inducing helper T cells, together with a cancer antigen peptide set forth in any one of SEQ ID NOS: 27-45 above.

Epitope peptides preferably comprise a helper peptide consisting of the amino acid sequence set forth in SEQ ID NO: 24 together with a cancer antigen peptide set forth in any one of SEQ ID NOS: 27-45.

More preferably, epitope peptides comprise a helper peptide consisting of the amino acid sequence set forth in SEQ ID NO: 24 together with a cancer antigen peptide set forth in any one of SEQ ID NOS: 27-30, 44 and 45.

The epitope peptides can be prepared by aforementioned usual method for peptide synthesis. It can also be prepared by a usual method for DNA synthesis and genetic engineering on the basis of sequence information of a polynucleotide encoding an epitope peptide wherein multiple epitopes are ligated. Specifically, an epitope peptide wherein a multiple epitopes are ligated can be prepared by inserting a polynucleotide encoding the peptide into a known expression vector, transforming a host cell with the resultant recombinant expression vector, culturing the transformants, and recovering the objective peptide from the culture. These processes can be conducted according to, for example, a method described in a literature (*Molecular Cloning*, T. Maniatis et al., CSH Laboratory (1983), *DNA Cloning*, D M. Glover, IRL PRESS (1985)), or that described hereinafter.

The activity of said epitope peptide as a helper peptide can be confirmed according to the above-mentioned method. Further, the activity of said epitope peptide as a cancer antigen peptide can be confirmed by subjecting the peptide to model animals for human described in WO02/47474 or *Int J. Cancer.* 100, 565-570, 2002.

An epitope peptide of the present invention is considered to be useful to establish more efficient treatment or prevention of cancer, because a helper peptide portion in the helper epitope peptide can activate helper T cells (CD4-positive T cells) to give activated helper T cells which exert various activities including induction of differentiation and maintenance of CTLs and activation of effectors such as macrophages, whereby it enhances CTL-induction by cancer antigen peptides further.

The amino group of the N-terminal amino acid or the carboxyl group of the C-terminal amino acid of the above-described peptide of the present invention (natural-, altered- or epitope-peptide) may be modified. The peptides wherein the N-terminal and/or C-terminal amino acid residue is modified fall within the scope of the peptide of the present invention.

Examples of a group usable in the modification of amino group of the N-terminal amino acid include 1 to 3 groups selected from $C_{1-6}$ alkyl group, phenyl group, cycloalkyl group and acyl group. Acyl groups include $C_{1-6}$ alkanoyl group, $C_{1-6}$ alkanoyl group substituted by phenyl group, carbonyl group substituted by $C_{5-7}$ cycloalkyl group, $C_{1-6}$ alkylsulfonyl group, phenylsulfonyl group, $C_{2-6}$ alkoxycarbonyl group, alkoxycarbonyl group substituted by phenyl group, carbonyl group substituted by $C_{5-7}$ cycloalkoxy group, phenoxycarbonyl group, and the like.

Examples of peptides modified at the carboxyl group of C-terminal amino acid include esters and amides. Esters specifically include $C_{1-6}$ alkyl esters, $C_{0-6}$ alkyl esters substituted by phenyl group, $C_{5-7}$ cycloalkyl esters, and the like. Amides specifically include amides, amides substituted by one or two $C_{1-5}$ alkyl groups, amides substituted by one or two $C_{0-6}$ alkyl groups that are substituted by phenyl group, amides forming 5- to 7-membered azacycloalkane inclusive of nitrogen atom of amide group, and the like.

The present invention also provides a polynucleotide encoding the above-mentioned peptide (natural-, altered- or epitope-peptide) of the present invention. The polynucleotide encoding a peptide of the present invention may be in the form of DNA or RNA. The polynucleotides of the present invention can be easily prepared on the basis of information about amino acid sequence of the present peptide or polynucleotide sequence of DNA encoding the same. Specifically, synthesis can be carried out using usual method of DNA synthesis or amplification by PCR.

Concrete examples of polynucleotides include those encoding the above-mentioned epitope peptides. More specifically, examples of polynucleotide include those encoding epitope peptides which comprise a helper peptide that is a WT1-derived partial peptide of 10-25 amino acids comprising an amino acid sequence set forth in any one of SEQ ID NOS: 2-23 and has an activity of binding to HLA-DRB1*0405 and inducing helper T cells, together with a cancer antigen peptide set forth in any one of SEQ ID NOS: 27-45 above.

Preferred examples include a polynucleotide encoding an epitope peptide which comprises a helper peptide consisting of the amino acid sequence set forth in SEQ ID NO: 24 and a cancer antigen peptide set forth in any one of SEQ ID NOS: 27-45.

More preferred examples include a polynucleotide encoding an epitope peptide which comprise a helper peptide consisting of the amino acid sequence set forth in SEQ ID NO: 24 and a cancer antigen peptide set forth in any one of SEQ ID NOS: 27-30, 44 and 45.

The "polynucleotide encoding the peptide of the present invention" encompasses polynucleotides that can hybridize under the stringent conditions to the complementary sequence of the said polynucleotide and that encode peptides which have activities equivalent to the peptide of the present invention. In relation to "hybridize under the stringent condition", the "hybridization" herein used can be carried out according to conventional method described in, for example, Sambrook J., Frisch E. F., Maniatis T. ed. *Molecular Cloning* 2nd edition, Cold Spring Harbor Laboratory press. The term "stringent conditions" means that hybridization is conducted in a solution containing 6×SSC (10× SSC=1.5 M NaCl, 1.5 M trisodium citrate), 50% formamide at 45° C., followed by washing in a solution of 2×SSC at 50° C. (*Molecular Biology*, John Wiley & Sons, N.Y. (1989), 6.3.1-6.3.6)), or the like.

A recombinant expression vector for expressing the peptide of the present invention can be constructed by incorporating a polynucleotide prepared above into an expression vector.

As expression vectors usable herein include plasmids, phage vectors, virus vectors, and the like.

When the host is *Escherichia coli*, examples of vector include plasmid vectors such as pUC118, pUC119, pBR322, pCR3, and the like; and phage vectors such as λZAPII, λgt11, and the like. When the host is yeast, examples of vector include pYES2, pYEUra3, and the like. When the host is insect cells, examples of vector include pAc-SGHisNT-A, and the like. When the host is animal cells, examples of vector include plasmid vectors such as pKCR, pCDM8, pGL2, pcDNA3.1, pRc/RSV, pRc/CMV, and the like; and virus vectors such as retrovirus vector, adenovirus vector, adeno-associated virus vector, and the like.

The expression vector may optionally contain a factor(s) such as promoter capable of inducing expression, a gene encoding a signal sequence, a marker gene for selection, terminator, and the like.

Furthermore, the expression vector may contain an additional sequence for allowing the peptide to express as a fusion protein with thioredoxin, His tag, GST (glutathione S-transferase), or the like, so as to facilitate the isolation and purification. Vectors usable in such a case include GST fusion protein vectors containing an appropriate promoter (lac, tac, trc, trp, CMV, SV40 early promoter, etc) that functions in host cells, such as pGEX4T; vectors containing Tag sequence (Myc, His, etc) such as pcDNA3.1/Myc-His; and vectors capable of expressing a fusion protein between thioredoxin and His tag such as pET32a.

Transformed cells containing the vector of the present invention can be prepared by transforming host cells with an expression vector obtained in the above.

Host cells usable herein include *Escherichia coli*, yeast, insect cells and animal cells. Examples of *Escherichia coli* include strains of *E. coli* K-12 such as HB101, C600, JM109, DH5α and AD494 (DE3). Examples of yeast include *Saccharomyces cerevisiae*. Examples of animal cells include L929, BALB/c3T3, C127, CHO, COS, Vero and Hela cells. Examples of insect cells include sf9.

Introduction of an expression vector into host cells can be done using a conventional method suited for the respective host cells above. Specifically, introduction can be done using calcium phosphate method, DEAE-dextran method, electroporation method, and a method using lipid for gene transfer (Lipofectamine, Lipofectin; Gibco-BRL). Following the introduction, the cells are cultured in a conventional medium containing a selection marker, whereby transformants containing the expression vector can be selected.

The peptide of the present invention can be produced by culturing the transformed cells under appropriate conditions (conditions under which peptides can be expressed). The resultant peptide may be further isolated and purified according to standard biochemical purification procedures. The purification procedures include salting out, ion exchange chromatography, absorption chromatography, affinity chromatography, gel filtration chromatography, etc. When the polypeptide of the present invention has been expressed as a fusion peptide with thioredoxin, His tag, GST, or the like, as mentioned above, the peptide can be isolated and purified by appropriate purification procedures making use of the characteristics of the fusion protein or tags.

The present invention provides an antibody which specifically binds to a peptide of the present invention. The antibody of the present invention is not restricted to any form and may be polyclonal or monoclonal antibody raised against a peptide of the present invention as an antigen.

As mentioned above, there is no limitation regarding the antibody of the present invention on the condition that it specifically binds to a peptide of present invention. Examples of preferred antibody include those specifically bind to a helper peptide that is a WT1-derived partial peptide of 10-25 amino acids comprising an amino acid sequence set forth in any one of SEQ ID NOS: 2-23 and has an activity of binding to HLA-DRB1*0405 and inducing helper T cells. Antibodies specifically bind to a helper peptide consisting of the amino acid sequence set forth in SEQ ID NO: 24 is more preferred.

Methods of preparation of antibodies are well known in the art and the antibodies of the present invention can be prepared according to any one of conventional methods (*Current protocols in Molecular Biology* edit. Ausubel et al. (1987) Publish. John Wiley and Sons. Section 11.12-11.13, Antibodies; *A Laboratory Manual*, Lane, H, D. et al., ed., Cold Spring Harber Laboratory Press, New York 1989).

Specifically, antibodies of the present invention can be obtained by immunizing a non-human animal such as rabbit using a peptide of the present invention as an antigen, and recovering the antibodies from serum of the immunized animal in a conventional manner. In the case of monoclonal antibodies, they can be obtained by immunizing a non-human animal such as mouse with a peptide of the present invention, subjecting the resultant splenocytes to cell fusion with myeloma cells, and recovering monoclonal antibodies from the resultant hybridoma cells (*Current protocols in Molecular Biology* edit. Ausubel et al. (1987) Publish. John Wiley and Sons. Section 11.4-11.11).

The antibodies against the peptide of the present invention can also be produced while enhancing the immunological response using different adjuvants depending on the host. Examples of adjuvants include Freund adjuvants; mineral gels such as aluminium hydroxide; surfactants such as lysolecithin, Pluronic® polyol, polyanion, peptide, oil emulsion, keyhole limpet hemocyanin and dinitorophenol; human adjuvants such as BCG (Bacille de Calmette-Guerin) or *Corynebacterium*, etc.

As mentioned above, antibodies that recognize a peptide of the present invention and antibodies that neutralize the activity thereof can easily be prepared by immunizing an animal in a conventional manner. The antibodies may be used in affinity chromatography, immunological diagnostic method, and the like. Immunological diagnostic method may be selected as appropriate from immunoblotting, radioimmunoassay (RIA), enzyme-linked immunosorbent assay (ELISA), a fluorescent or luminescent assay, and the like. The immunological diagnostic method is effective in the diagnosis of cancer expressing WT1 gene such as gastric cancer, colon cancer, lung cancer, breast cancer, embryonal cancer, skin cancer, bladder cancer, prostate cancer, uterine cancer, cervical cancer, ovarian cancer, and the like.

The present invention provides a pharmaceutical composition comprising a peptide (natural-, altered-, and epitope-type peptides) of the present invention, an expression vector containing a polynucleotide of the present invention or a cell containing an expression vector of the present invention, in association with a pharmaceutically acceptable carrier. The pharmaceutical composition can be used effectively as an inducer of helper T cells or an enhancer of cancer vaccine efficacy, as described in detail below.

(1) An Inducer of Helper T Cells Comprising as an Active Ingredient a Peptide of the Present Invention (an Enhancer of Cancer Vaccine Efficacy)

The peptide of the present invention has an activity of inducing helper T cells, and the induced helper T cells in turn are able to enhance the CTL-inducing activity, which is the effects of cancer vaccine, through the induction of differentiation and maintenance of CTLs and the activation of effectors such as macrophages. Thus, the present invention provides an enhancer of cancer vaccine efficacy comprising as an active ingredient a peptide of the present invention (pharmaceutical composition as an agent for enhancing efficacy of cancer vaccine). When the enhancer of the present invention is administered to an HLA-DRB1*0405-positive and WT1-positive patient, the peptide is presented to HLA-DRB1*0405 antigen of an antigen-presenting cell; specific helper T cells (CD4-positive T cells) recognizing a complex of the peptide and HLA-DRB1*0405 antigen are induced and activated; and the activated helper T cells can exert the activity concerning induction of differentiation and maintenance of CTLs and activation of effectors such as macrophages. In this manner, the activity of activating and inducing CTLs as the effect of cancer vaccine is enhanced.

The enhancer of cancer vaccine efficacy of the present invention can be used in the prevention or treatment of cancer accompanied by elevated expression level of WT1 gene, for example, blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

The enhancer of cancer vaccine efficacy of the present invention can be administered concurrently with, before or after the administration of cancer vaccine.

The enhancer of cancer vaccine efficacy comprising as an active ingredient a peptide of the present invention may contain as an active ingredient a helper peptide(s) or an epitope peptide wherein a peptide(s) is ligated with a cancer antigen peptide(s) (CTL epitope(s)) As mentioned above, it has recently been shown that an epitope peptide wherein a cancer antigen peptide (CTL epitope) and a helper peptide (helper epitope) can induce CTLs efficiently. When an epitope peptide of this form is administered, said peptide is incorporated into antigen-presenting cells; among the antigen peptides generated by intracellular degradation, helper peptides bind to MHC class II antigen (HLA-DRB1*0405) while cancer antigen peptides to MHC class I antigen; and respective complexes thus formed are presented on the surface of antigen-presenting cells in high density. When helper T cells recognize the complex of HLA-DRB1*0405 antigen and helper peptide, the CTL-inducing activity that is the effect of cancer vaccine is further enhanced as a result of induction of differentiation and maintenance of CTLs and the activation of effectors such as macrophages. On the other hand, when CTLs recognize the complex of cancer antigen peptides and MHC class I antigen, CTLs proliferate and destroy the cancer cells. Thus, the pharmaceutical composition of the present invention comprising as an active ingredient an epitope peptide of the present invention can be used as a cancer vaccine per se, as well as an enhancer of cancer vaccine efficacy.

The enhancer of cancer vaccine efficacy which comprises as an active ingredient a peptide of the present invention may be administered together with a pharmaceutically acceptable carrier, for example, an appropriate adjuvant, or in the form of particles so that the cellular immunity can be established effectively. As an adjuvant, those described in a literature (*Clin. Microbiol. Rev.*, 7:277-289, 1994), and the like are applicable. Concrete examples include microorganism-derived components, cytokines, plant-derived components, marine organism-derived components, mineral gels such as aluminium hydroxide, surfactants such as lysolecithin and Pluronic® polyols, polyanions, peptides, oil emulsion (emulsion preparations) and the like. Liposomal preparations, particulate preparations in which the ingredient is bound to beads having a diameter of several µm, preparations in which the ingredient is attached to lipids, and the like, are also contemplated.

Administration may be achieved, for example, intradermally, subcutaneously, intramuscularly, or intravenously. Although the dosage of the peptide of the present invention in the formulation may be adjusted as appropriate depending on, for example, the disease to be treated, the age and the body weight of a patient, it is usually within the range of 0.0001 mg-1000 mg, preferably 0.001 mg-1000 mg, more preferably 0.1 mg-10 mg, which can be preferably administered once in every several days to every several months.

The present invention also provides a pharmaceutical composition comprising a combination of a peptide of the present invention and a cancer antigen peptide. According to the combined use of the present invention, the effect of a cancer antigen peptide as cancer vaccine (i.e., activity of inducing and activating CTLs) is enhanced by the peptide of the present invention, and the treatment or prevention of cancer can be achieved more effectively.

The term "combination" encompasses the both forms where a peptide of the present invention and a cancer antigen peptide are administered in a mixed form or discrete forms.

Administration of the peptides in the mixed form can be conducted using a previously prepared formulation containing the peptides as a mixture, or combining previously prepared formulations each comprising the respective peptides before use.

In the case where peptides are administered in discrete forms, the discrete formulations may be administered successively with a time-interval, or administered concurrently. When administration is conducted with a time-interval, a peptide of the present invention (enhancer of cancer vaccine efficacy) and a cancer antigen peptide (cancer vaccine) may be administered in this order or in reverse order.

An embodiment of the combination of a peptide of the present invention and a cancer antigen peptide includes a kit.

As a cancer antigen peptide usable in combination with a peptide of the present invention, any cancer antigen peptides conventionally known can be used, and examples include WT1-derived cancer antigen peptides (natural-, altered-type). Concrete examples include a cancer antigen peptide set forth in any one of SEQ ID NOS: 27-45, preferably, SEQ ID NOS: 27-30, 44 and 45.

(2) Inducer of Helper T Cells (Enhancer of Cancer Vaccine Efficacy) Comprising as an Active Ingredient an Expression Vector of the Present Invention An expression vector containing a polynucleotide encoding a peptide of the present invention, similar to the above-mentioned peptide of the present invention, has an activity of inducing helper T cells and is useful as an active ingredient of an enhancer of cancer vaccine efficacy of the present invention. Thus, the present invention provides an enhancer of cancer vaccine efficacy (i.e., a pharmaceutical composition as an agent enhancing efficacy of cancer vaccine) comprising as an active ingredient an expression vector containing a polynucleotide encoding a peptide of the present invention.

Recently, a polynucleotide encoding an epitope peptide wherein a cancer antigen peptide (CTL epitope) and a helper peptide (helper epitope) are ligated has been shown to have an activity of inducing CTLs in vivo efficiently. For example, it is reported that a DNA (minigene) encoding an epitope peptide wherein HBV-originated HLA-A2-restricted antigen peptides (6 peptides), HLA-A11-restricted antigen peptides (3 peptides) and a helper epitope are ligated induced in vivo CTLs directed to the respective epitopes efficiently (*Journal of Immunology* 1999, 162: 3915-3925).

Accordingly, an active ingredient of enhancer of cancer vaccine efficacy can be obtained by incorporating a polynucleotide encoding the above-described epitope peptide of present invention into an appropriate expression vector.

When administering an expression vector containing a polynucleotide of the present invention as an active ingredient of enhancer of cancer vaccine efficacy, the following methods can be used.

As a method for introducing an expression vector containing the polynucleotide of the present invention into cells, any means including those utilizing viral vectors or other methods are applicable (*Nikkei-Science*, April, 1994, p 20-45; *Gekkan-Yakuji*, 36(1), p 23-48 (1994); *Jikken-Igaku-Zokan*, 12(15), 1994, and references cited therein).

Examples of means utilizing a viral vector include those wherein a DNA of the present invention is incorporated into DNA or RNA virus such as retrovirus, adenovirus, adeno-associated virus, herpes virus, vaccinia virus, poxvirus, poliovirus, or Sindbis virus, and then introduced into cells. Above all, a method utilizing retrovirus, adenovirus, adeno-associated virus, or vaccinia virus, or the like, is particularly preferred.

Examples of other methods include those wherein an expression vector is directly injected intramuscularly (DNA vaccination), liposome method, Lipofectin method, microinjection, calcium phosphate method and electroporation. DNA vaccination and liposome method are particularly preferred.

Regarding a method to make the expression vector of the present invention act as a medicament in practice, there are an in vivo method wherein the expression vector is directly introduced into the body and an ex vivo method wherein the expression vector is introduced extracorporeally into a certain cells removed from human, and the cells are reintroduced into the body (*Nikkei-Science*, April, 1994, 20-45; *Gekkan-Yakuji*, 36(1), 23-48 (1994); *Jikkenn-Igaku-Zokan*, 12(15), 1994; and references cited therein). The in vivo method is more preferred.

In the case of in vivo method, the administration can be effected through any appropriate routes depending on the disease and symptoms to be treated. For example, it may be administered via intravenous, intraarterial, subcutaneous, intracutaneous, intramuscular route, or the like. When the administration is carried out by in vivo method, the compositions may be administered in various forms such as solution, and are typically formulated, for example, in the form of injection containing, as an active ingredient, an expression vector of the present invention to which conventional carriers may also be added, if necessary. As for the liposomes or membrane-fused liposomes (such as Sendai virus (HVJ)-liposomes) containing an expression vector of the present invention, they may be in the form of liposomal formulation such as suspension, frozen drug, centrifugally-concentrated frozen drug, or the like.

Although the content of an expression vector in a formulation may be adjusted as appropriate depending on, for example, the disease to be treated, age and body weight of a patient, usually, 0.0001 mg-100 mg, preferably 0.001 mg-10 mg of an expression vector of the present invention can be administered once in every several days to every several months.

When the above-mentioned expression vector of the present invention is administered to an HLA-DRB1*0405-positive and WT1-positive patient, the peptide of the present invention is presented to HLA-DRB1*0405 antigen of an antigen-presenting cell; specific helper T cells (CD4-positive T cells) recognizing a complex of the peptide and HLA-DRB1*0405 antigen are induced and activated; the activated helper T cells can exert the activity concerning induction of differentiation and maintenance of CTLs and activation of effectors such as macrophages. In this manner, the activity of inducing CTLs as an effect of cancer vaccine is enhanced. The enhancer of cancer vaccine efficacy comprising as an active ingredient an expression vector containing a polynucleotide of the present invention can be used in the prevention or treatment of cancer accompanied by elevated expression level of WT1 gene, for example, blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

In the above case where an expression vector containing a polynucleotide encoding an epitope peptide is administered, antigen presenting cells incorporate the same and generate antigen peptides through intracellular degradation, of which helper peptides and cancer antigen peptides bind to MHC class II antigen (HLA-DRB1*0405) and MHC class I antigen, respectively, to form complexes. The so formed complexes are presented on the surface of antigen presenting cells in high density. When helper T cells recognize the complex of HLA-DRB1*0405 antigen and helper peptide, the CTL-inducing activity that is the effect of cancer vaccine is further enhanced through the induction of differentiation and maintenance of CTLs and the activation of effectors such as macrophages. On the other hand, when CTLs recognize the complex of cancer antigen peptides and MHC class I antigen, CTLs proliferate and destroy the cancer cells. Thus, the pharmaceutical composition of the present invention comprising as an active ingredient an expression vector containing a polynucleotide encoding an epitope peptide of the present invention can be used as a cancer vaccine per se, as well as an enhancer of cancer vaccine efficacy.

The present invention also provides a peptide consisting of 10-25 contiguous amino acids in the amino acid sequence of human WT1 set forth in SEQ ID NO: 1, said peptide binding to HLA-DRB1*1502 and inducing helper T cells. The present invention encompasses antigen peptides binding to HLA-DRB1*1502 wherein the N-terminal and/or C-terminal amino acid residue is modified or those wherein a particular amino acid residue(s) is altered.

The synthesis and determination of activity of antigen peptides binding to HLA-DRB1*1502 of the present invention can be carried out in a manner similar to that described in relation to the above-mentioned antigen peptides binding to HLA-DRB1*0405 of the present invention.

The HLA-DRB1*1502-binding antigen peptides of the present invention is a partial peptide which consists of 10-25 contiguous amino acids in the amino acid sequence of human WT1 set forth in SEQ ID NO: 1. Preferred peptides are those consisting of 13-17 contiguous amino acids in the amino acid sequence of human WT1.

The present invention is based on the finding that human WT1 contains an antigen peptide portion having activity of binding to HLA-DRB1*1502 and inducing helper T cells. Search for 9-amino-acid portions potentially binding to HLA-DRB1*1502 (9-amino-acid portions capable of being accommodated in a peptide-binding groove of MHC class II molecule) was conducted using a software for predicting MHC class II binding peptides (Propred, *Bioinformatics* 17: 1236, 2001). Examples of the identified 9-amino-acid portions of WT1 are shown in SEQ ID NOS: 46-56. Thus, specific examples of HLA-DRB1*1502-binding antigen peptides of the present invention include a peptide which comprises an amino acid sequence set forth in any one of SEQ ID NOS: 46-56, and which binds to HLA-DRB1*1502 and induces helper T cells.

The said peptides preferably consist of about 10-25 amino acids, and more preferably about 13-17 amino acids. Examples of more preferred embodiments include partial peptides derived from WT1 consisting of 10-25 amino acids (preferably, 13-17 amino-acids), which comprise the amino acid sequence set forth in SEQ ID NO: 50, and which have an activity of binding to HLA-DRB1*1502 and inducing helper T cells. Examples of still more preferred embodiments include partial peptides derived from WT1 consisting of 16-25 amino acids (preferably, 16-17 amino-acids), which comprise the amino acid sequence set forth in SEQ ID NO:

24, and which have an activity of binding to HLA-DRB1*1502 and inducing helper T cells. The amino acid sequence set forth in SEQ ID NO: 24 represents a 16-amino-acid partial peptide derived from WT1 and includes the amino acid sequence set fort in SEQ ID NO: 50.

Further preferred embodiment is the $WT1_{332-347}$ peptide consisting of the amino acid sequence set forth in SEQ ID NO: 24.

The said $WT1_{332-347}$ peptide is a promiscuous helper peptide which binds not only to HLA-DRB1*0405 molecule but also to HLA-DRB1*1502 molecule. Accordingly, $WT1_{332-347}$ is a helper peptide applicable to patients having HLA-DRB1*0405 and those having HLA-DRB1*1502 as well, and hence is useful from the viewpoint of wide application range of patients.

The epitope peptide, polynucleotide, antibody, and pharmaceutical composition regarding the HLA-DRB1*1502-binding antigen peptide of the present invention can be made and use (put into effect) in a manner similar to above-mentioned HLA-DRB1*0405-binding antigen peptide of the present invention.

EXAMPLES

The present invention is further illustrated by the following examples, but should not be construed as being limited thereto.

Example 1

1. Preparation of Dendritic Cells

Peripheral blood mononuclear cells (PBMCs) were isolated by density gradient centrifugation with Ficoll-Paque from blood of an HLA-DRB1*0405-positive healthy volunteer. The resultant $8 \times 10^6$ PBMCs were suspended in 2 ml of X-VIVO 15™ medium (Camblex) containing 1% AB serum, seeded in a 6-well culture plate, and cultured for 2 hours. After cultivation, non-adherent cells were removed, and the adherent cells were washed with Hanks solution. Adherent cells were cultured in X-VIVO 15™ medium containing 1% AB serum, 1000 U/ml IL-4 and 1000 U/ml GM-CSF. On days 2 and 4 of cultivation, one-half of medium was replaced by fresh medium. On day 6, TNF-α was added to make the final concentration of 100 U/ml. Cells existing on day 7 were used as dendritic cells in the experiment.

2. Preparation of CD4-Positive T Cells (Helper T Cells)

Blood obtained from the same healthy volunteer as in (1) above was used. Blood was diluted by 2-times with RPMI medium. To about 100 ml of the diluted blood was added antibody cocktail, RosetteSep™ (Stemcell) for separation of CD4-positive T cells, and the mixture was left to stand at room temperature for 20 minutes. CD4-positive T cells were then collected by density gradient centrifugation with Ficoll-Paque.

3. Induction of WT1 Peptide-Specific CD4-Positive T Cells

Amino acid sequence of WT1 protein (NCBI database, Accession No. P19544, XP_034418, SEQ ID NO: 1) was searched for peptides potentially binding to HLA-DRB1*0405 using a prediction program (Propred, *Bioinformatics* 17: 1236, 2001). Three peptides were selected and synthesized. These peptides have the same amino acid sequences as those present at the following positions of WT1:

Position 172-186:
($WT1_{172-186}$, SEQ ID NO: 25)
PNHSFKHEDPMGQQG;

Position 225-243:
($WT1_{225-243}$, SEQ ID NO: 26)
NLYQMTSQLECMTWNQMNL;
and

Position 332-347:
($WT1_{332-347}$, SEQ ID NO: 24)
KRYFKLSHLQMHSRKH.

Dendritic cells prepared in (1) above were seeded in 24-well culture plate at $3 \times 10^5$ cells/well, and a peptide of SEQ ID NO: 24 was added up to 50 μg/ml. After 4-hour-cultivation, cell growth was stopped by X-ray irradiation (25 Gy). CD4-positive cells prepared in (2) above were added to each well at $3 \times 10^6$ cells/well and cocultured with dendritic cells. As medium, X-VIVO 15™ medium containing 1% AB serum was used. After the cultivation was started, one half of medium was replaced with fresh medium every 2 days and IL-2 was added up to 20 U/ml. On days 7 and 14 from the beginning of cultivation, T cells were collected and seeded in 24-well plate at $3 \times 10^6$ cells/well, and thereto were added $3 \times 10^5$ dendritic cells having been pulsed with 20 μg/ml of a peptide (SEQ ID NO: 24) and undergone X-ray irradiation (25 Gy). The cells were then cocultured. As medium, X-VIVO 15™ medium containing 1% AB serum and 20 U/ml IL-2 was used.

After the third stimulation, T cells were recovered and seeded in 96-well plate at $3 \times 10^4$ cells/well. Dendritic cells having been pulsed with 20 μg/ml of a peptide (SEQ ID NO: 24) and undergone X-ray irradiation (25 Gy) were added at $3 \times 10^4$ cells/well, followed by coculture. As a negative control group, T cells were cocultured with dendritic cells not pulsed with the peptide, and as a positive control group, 0.2% PHA was added instead of dendritic cells. After 80-hour-cultivation, [$^3$H]-thymidine (37 kBq/well) was added, and the cells were cultured for another 16 hours. [$^3$H]-thymidine incorporated by cells was then measured using β-scintillation counter. The results are shown in FIG. 1. CD4-positive T cells stimulated with a peptide at position 332-347 of WT1 ($WT1_{332-347}$, SEQ ID NO: 24) showed proliferative response when cocultured with dendritic cells pulsed with $WT1_{332-347}$. However, CD4-positive T cells did not show proliferative response when cocultured with dendritic cells not pulsed with the peptide, or dendritic cells pulsed with a peptide having amino acid sequence of SEQ ID NO: 25 or 26 which is different from that of SEQ ID NO: 24. These results demonstrate that the $WT1_{332-347}$ peptide (SEQ ID NO: 24) induces specific CD4-positive T cells as an antigen peptide.

Example 2

Establishment of CD4-Positive T-Cell Lines Specific for WT1 Peptides

Figure 2:
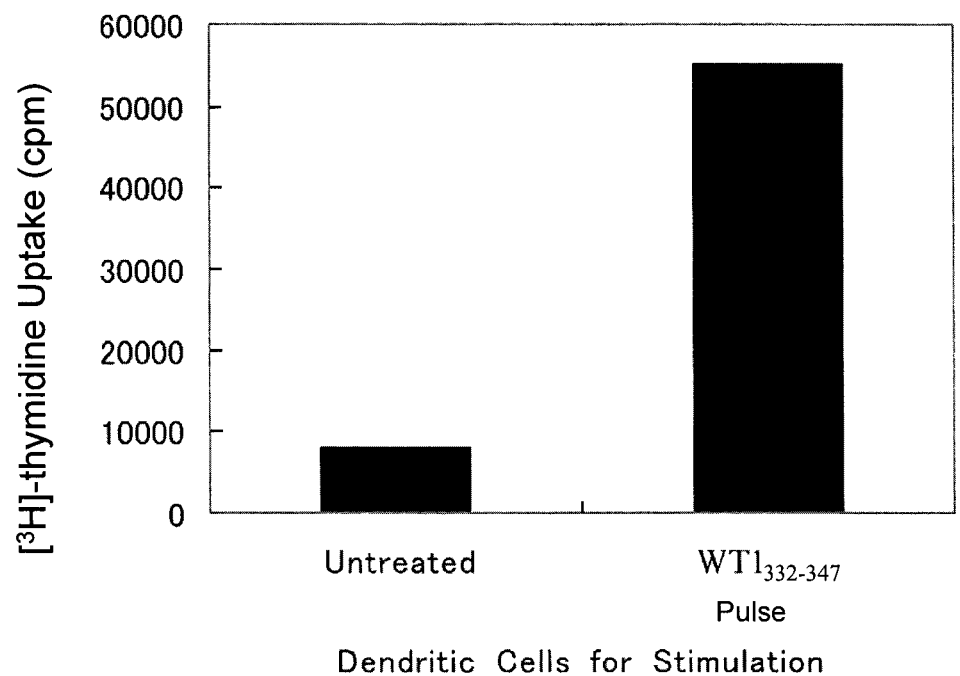
FIG. 2 shows the results of examination into responsiveness of G2 cell lines to dendritic cells pulsed with a WT1-derived $WT1_{332-347}$ peptide. In the figure, "Untreated" represents the results obtained using dendritic cells not pulsed with a peptide; and "$WT1_{332-347}$ pulse" to the results obtained using dendritic cells pulsed with $WT1_{332-347}$. The vertical axis indicates the amount of [$^3$H]-thymidine uptake (cpm) by G2 cell lines.

Dendritic cells prepared in a manner similar to Example 1 were seeded in 96-well plate at $10^4$ cells/well, and then CD4-positive T cells induced by $WT1_{332-347}$ peptide (SEQ ID NO: 24) were seeded at $10^3$ cells/well. As medium, X-VIVO 15™ medium containing 1% AB serum, 20 U/ml IL-2 and 5 μg/ml PHA was used. CD4-positive T-cell line was established by continued cultivation and named as "G2 cell line". Responsiveness of G2 cell line to dendritic cells pulsed with a peptide was measured by a similar method to Example 1. The results are shown in FIG. 2. G2 cell line showed proliferative response when cocultured with dendritic cells pulsed with $WT1_{332-347}$ peptide, but did not when cocultured with dendritic cells not-pulsed with the peptide.

These results demonstrate that G2 cell line is a CD4-positive T-cell line specific for $WT1_{332-347}$ peptide.

Example 3

Antigen Presentation of WT1 Peptide to HLA-DR Molecule

Figure 3:
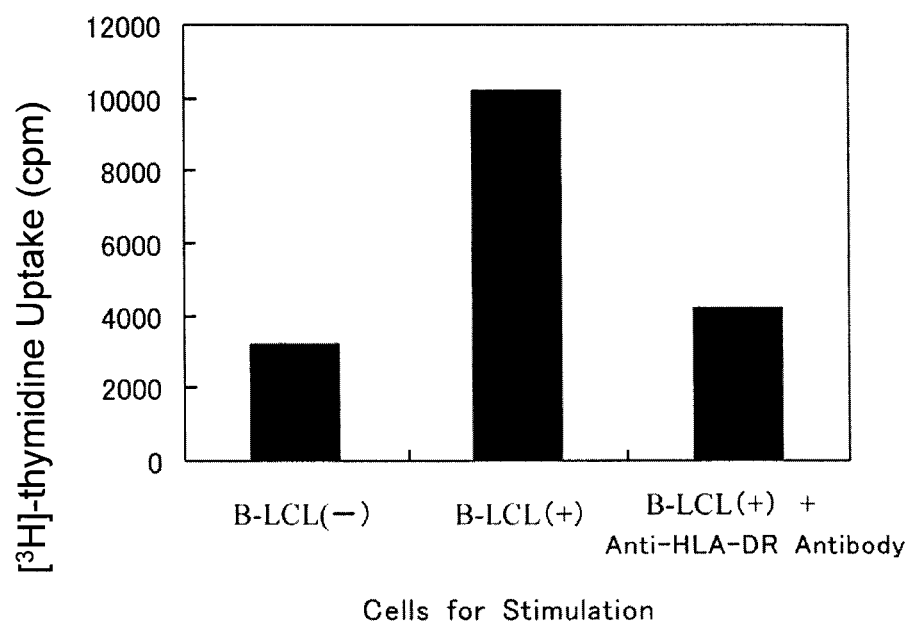
FIG. 3 shows the results of examination into responsiveness of G2 cell line to B-LCL(+) cells expressing WT1 gene. In the figure, "B-LCL(−)" represents the results obtained using B-LCL(−) cells not-expressing WT1 gene, "B-LCL (+)" the results obtained using B-LCL(+) cells expressing WT1 gene, and "B-LCL(+)+anti-HLA-DR antibody" to the results obtained using B-LCL(+) cells treated with anti-HLA-DR antibody. The vertical axis indicates the amount of [$^3$H]-thymidine uptake (cpm) by G2 cell lines.

Peripheral blood mononuclear cells (PBMCs) were isolated by density gradient centrifugation with Ficoll-Paque from blood of an HLA-DRB1*0405-positive healthy volunteer in a manner similar to Example 1. PBMCs were then seeded in 24-well plate at $10^7$ cells/well. As medium, RPMI1640 medium containing 10% FCS and 55 μM 2ME was used. After adding medium containing Epstein-Barr virus (EBV), cultivation was continued for another 4 weeks to establish B-cell line transformed with EBV, which cell line was named as "B-LCL(−) cell". EBV was prepared from culture supernatant of B95-8 (JCRB Cell Bank No. 9123), a cell line that produces EBV. B-LCL(−) cells were adjusted to $3 \times 10^7$ cells/mL, and thereto were added medium containing virus expressing WT1 gene and then polypropylene (final concentration, 8 μg/mL), and the mixture was added to a 24-well plate at 1 ml/well. After 16-hour-cultivation, 1 ml of fresh medium was added to each well, and cultivation was continued. To each well was added G418 (neomycin) up to 0.7 μg/mL, and the plate was cultured for 5 to 7 days, when cells into which the gene was introduced were selected. The selected B-cell line expressing WT1 was named as "B-LCL(+) cell". The amount of WT1 gene expressed by B-LCL(−) and B-LCL(+) cells was measured by RT-PCR technique according to the method described in *Blood*, 89:1405, 1997. The measurements were converted by assuming the expression amount of K562 cell line as the positive control to be 1. The resulting value for B-LCL(−) cells was $1.6 \times 10^{-4}$ while that for B-LCL(+) cells 3.2, indicating that WT1 gene is highly expressed. Responsiveness of G2 cells to B-LCL(+) cells was examined in a manner similar to Example 2. In a test group, B-LCL(+) cells were treated with anti-HLA-DR antibody before mixing with G2 cells to confirm the HLA-DR-restriction. The results are shown in FIG. 3. It was revealed that G2, which is a CD4-positive T-cell line positive for the peptide, shows proliferative response when cocultured with B-LCL(+) cells expressing endogenous WT1 genes, and that said response is inhibited by anti-HLA-DR antibody. These results demonstrate that $WT1_{332-347}$ peptide is intracellularly generated from WT1 protein and endogenously presented as an antigen to HLA-DR molecule.

Example 4

Establishment of CD4-Positive T-Cell Lines E04.1 Specific for $WT1_{332-347}$ Peptide Dendritic cells were prepared using blood isolated from an HLA-DRB1*0405-positive healthy volunteer in a manner similar to Example 1 except that the final concentration of TNF-α added on day 6 was 200 IU/ml. CD4-positive T cells were prepared using blood obtained from the same healthy volunteer as that used for the preparation of dendritic cells. CD4-positive T cells were separated according to the instructions of RosetteSep (StemCell) for separation of CD4-positive T cells.

The above-described dendritic cells and CD4-positive T cells were used to induce CD4-positive T cells specific for a WT1 peptide (SEQ ID NO: 24, $WT1_{332-347}$) in a manner similar to Example 1. The resultant CD4-positive T cells specific for $WT1_{332-347}$ peptide were cultured continuously by limiting dilution technique to establish CD4-positive T-cell line E04.1. As feeder cells in the limiting dilution technique, PBMCs prepared in a manner similar to Example 1 and treated by X-ray irradiation were seeded at $1 \times 10^5$ cells/well. As medium, X-VIVO 15™ medium containing 20 IU/ml IL-2 and 5 μg/ml PHA was used.

Figure 4:
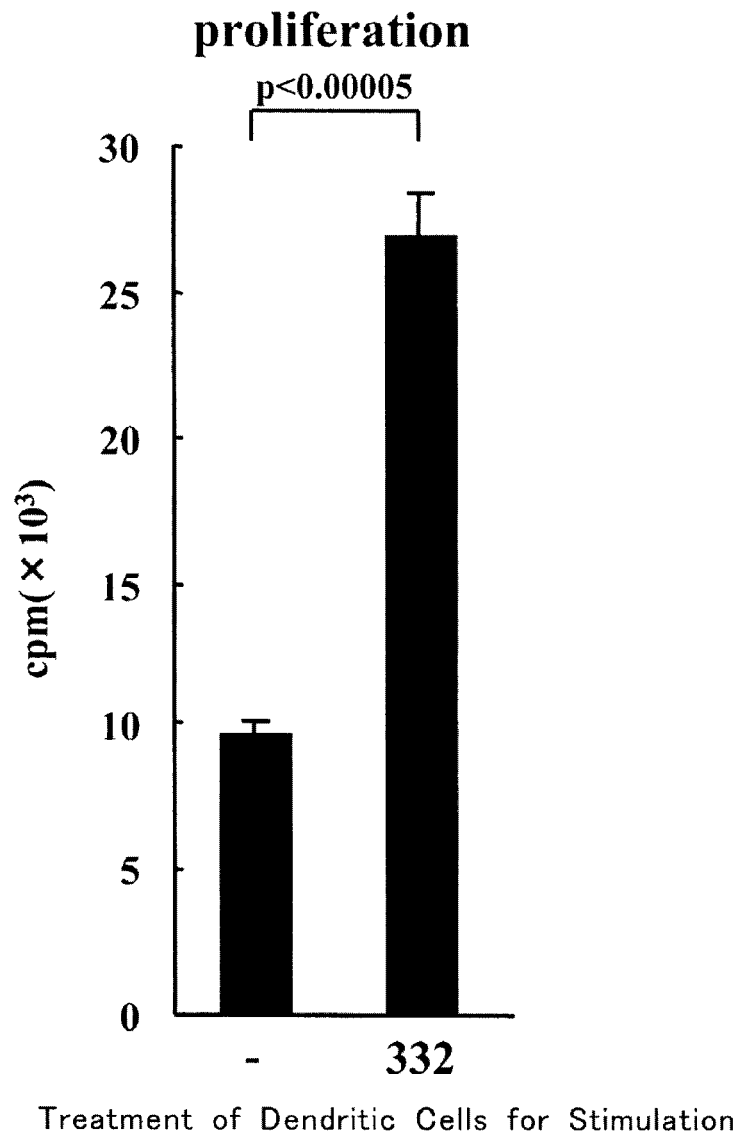
FIG. 4 shows the results of examination into responsiveness of E04.1 cell line to dendritic cells pulsed with a WT1-derived $WT1_{332-347}$ peptide. In the figure, "−" represents the results obtained using dendritic cells not pulsed with a peptide, and "332" the results obtained using dendritic cells pulsed with $WT1_{332-347}$ peptide. The vertical axis indicates the amount of [$^3$H]-thymidine uptake (cpm) by E04.1 cell lines.

Responsiveness of E04.1 cell line to dendritic cells pulsed with $WT1_{332-347}$ peptide was measured by a similar method to Example 1 except that cultivation was continued for 18 hours after adding [$^3$H]-thymidine. The results are shown in FIG. 4. E04.1 cells showed proliferative response when cocultured with dendritic cells pulsed with $WT1_{332-347}$ peptide but did not when cocultured with dendritic cells not-pulsed with the peptide. These results demonstrate that E04.1 cell is a CD4-positive T-cell line specific for $WT1_{332-347}$ peptide.

Example 5

Specific Binding of $WT1_{332-347}$ Peptide to HLA-DR

E04.1 cells established in Example 4 were seeded in 96-well culture plate at $1 \times 10^4$ cells/well. B cell line B-LCL (−) cells established from blood of an HLA-DRB1*0405-positive healthy volunteer in Example 3 were pulsed with $WT1_{332-347}$ peptide at a concentration of 20 μg/ml and treated by X-ray irradiation, seeded in 96-well plate at $3 \times 10^4$ cells/well, and cocultured with E04.1 cells. As a negative control group, B-LCL (−) cells not pulsed with the peptide were cocultured with E04.1 cells.

As test groups, B-LCL (−) cells having been pulsed with $WT1_{332-347}$ peptide and undergone X-ray irradiation were treated with 20 μg/ml of anti-HLA-DR antibody (G46.6, BD ParMingen), anti-HLA-class I antibody (G46-2.6, BD ParMingen), or anti-HLA-DQ antibody (SPVL3, Immunotech) for 30 minutes, and cocultured with E04.1 cells to confirm HLA-DR restricted nature. As a negative control group for antibody treatment, cells treated with anti-mouse IgG antibody were cocultured with E04.1 cells in a similar manner.

Figure 5:
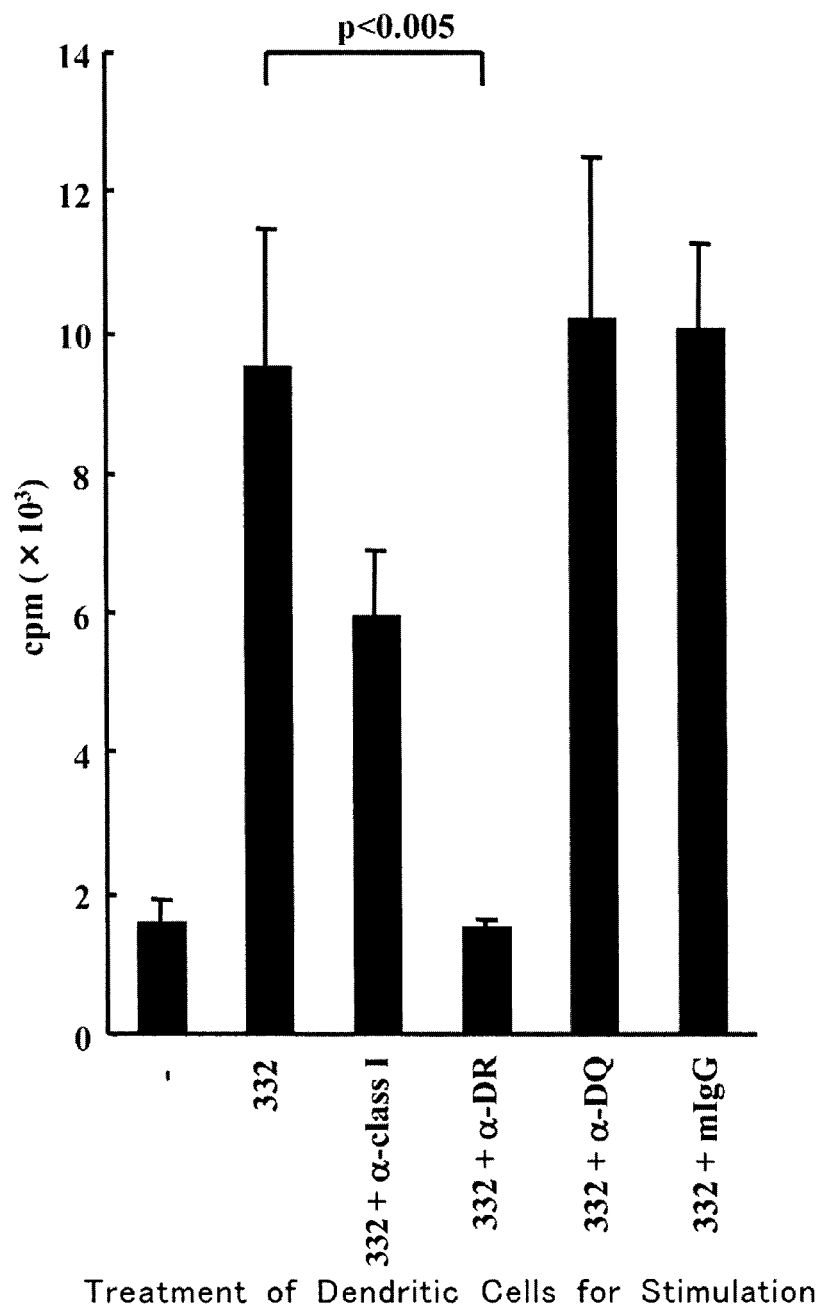
FIG. 5 shows the results of examination into responsiveness of E04.1 cell line to stimulated cells which have been pulsed with WT1-derived $WT1_{332-347}$ peptide and then treated with various anti-HLA inhibitory antibodies. The stimulated cell used is B-LCL(−) cell which is a B cell line established from blood of a healthy volunteer positive for HLA-DRB1*0405 as shown herein below in Example 3. In the figure, "-" represents the results obtained using stimulated cells not pulsed with a peptide, and "332" the results obtained using stimulated cells pulsed with $WT1_{332-347}$ peptide. Further, "332+α-classI" represents the results obtained using stimulated cells treated with $WT1_{332-347}$ peptide and anti-HLA-class I antibody, "332+α-DR" to the results obtained using stimulated cells treated with the $WT1_{332-347}$ peptide and anti-HLA-DR antibody, "332+α-DQ" to the results obtained using stimulated cells treated with $WT1_{332-347}$ peptide and anti-HLA-DQ antibody. In addition, "332+mIgG" represents the results obtained using stimulated cells treated with $WT1_{332-347}$ peptide and anti-mouse-IgG antibody as a negative control for inhibitory antibody. The vertical axis indicates the amount of [$^3$H]-thymidine uptake (cpm) by E04.1 cell lines.

Following cocultivation, growth of E04.1 cells was measured in a manner similar to Example 4. The results are shown in FIG. 5. E04.1 cells showed proliferative response when cocultured with B-LCL (−) cells pulsed with $WT1_{332-347}$ peptide. However, when $WT1_{332-347}$ peptide-pulsed B-LCL (−) cells were treated with anti-HLA-DR antibody, growth of cells was inhibited. Further, E04.1 cells showed proliferative response to $WT1_{332-347}$-peptide-pulsed B-LCL (−) cells treated with other antibody, but did not show proliferative response to B-LCL (−) cells not pulsed with the peptide. These results demonstrate that $WT1_{332-347}$ peptide specifically binds to HLA-DR among HLA molecules, and induces growth of CD4-positive E04.1 cell line specific for $WT1_{332-347}$ peptide.

Example 6

Specific Binding of $WT1_{332-347}$ Peptide to HLA-DRB1*0405

PBMCs were prepared from blood of HLA-DRB1*0405-positive or -negative healthy volunteer in a manner similar to Example 4. PBMCs were then pulsed with 20 μg/ml of $WT1_{332-347}$ peptide and subjected to X-ray irradiation, and seeded in 96-well plate at $3 \times 10^4$ cells/well. E04.1 cells were then seeded into the 96-well plate at $1 \times 10^4$ cells/well, and the cells were cocultured. As a negative control group, PBMCs not pulsed with the peptide and E04.1 cells were cocultured.

Figure 6:
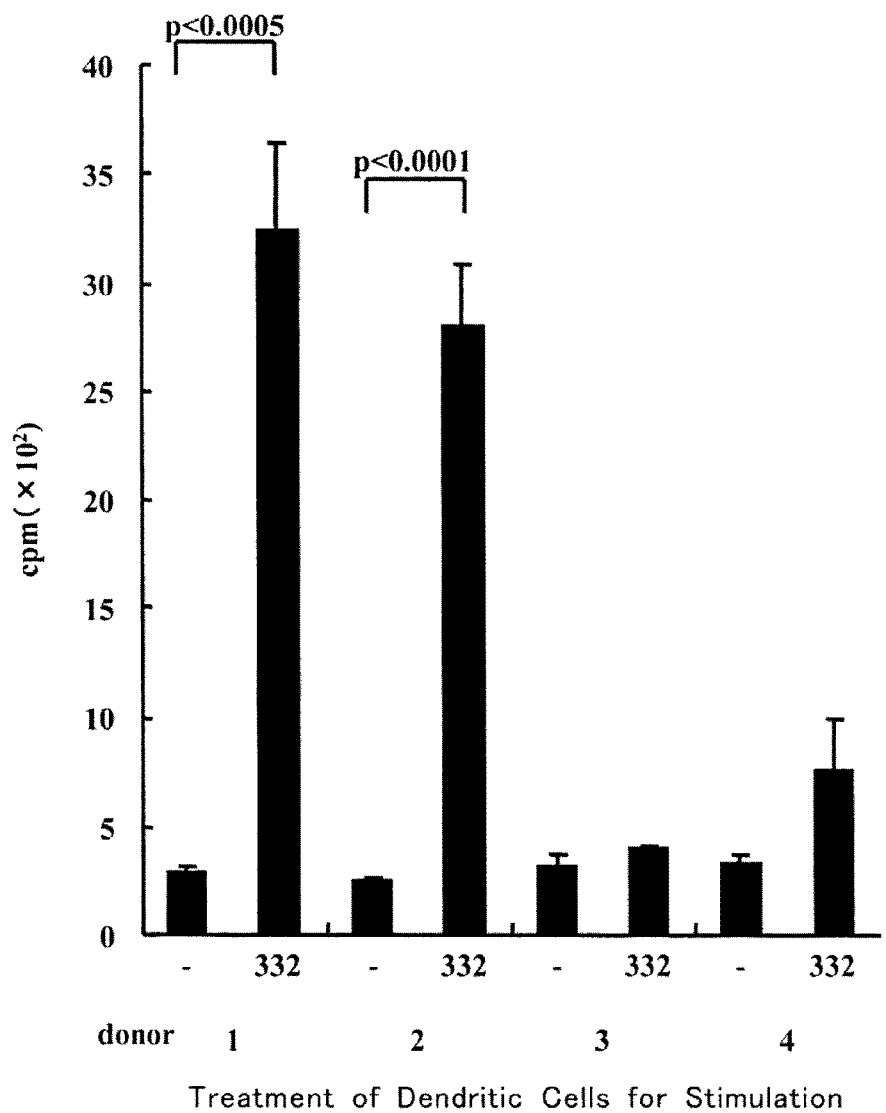
FIG. 6 shows the results of examination into responsiveness of E04.1 cell line to HLA-DRB1*0405-positive or -negative PBMC pulsed with WT1-derived $WT1_{332-347}$ peptide. In the figure, "-" represents the results obtained using PBMC not pulsed with a peptide, and "332" the results obtained using PBMC pulsed with $WT1_{332-347}$ peptide. HLA-DRB1 genotypes of respective donors are as follows. Donor 1 (HLA-DRB1*0405/0803), Donor 2 (HLA-DRB1*0405/0101), Donor3 (HLA-DRB1*0101/1001) and Donor 4 (HLA-DRB1*1201/0802). The vertical axis indicates the amount of [$^3$H]-thymidine uptake (cpm) by E04.1 cell lines.

Following cocultivation, growth of E04.1 cells was measured in a manner similar to Example 4. The results are shown in FIG. 6. Donor 1 (HLA-DRB1*0405/0803) and Donor 2 (HLA-DRB1*0405/0101) are HLA-DRB1*0405-positive, and E04.1 cells cocultured with PBMCs isolated from each donor and pulsed with $WT1_{332-347}$ peptide showed proliferative response. On the other hand, Donor 3 (HLA-DRB1*0101/1001) and Donor 4 (HLA-DRB1*1201/0802) are HLA-DRB1*0405-negative, and E04.1 cells cocultured with PBMCs isolated from each donor and pulsed with $WT1_{332-347}$ peptide did not show proliferative response. Further, in all cases, no proliferative response was observed when PBMCs not-pulsed with the peptide were used. The above results demonstrate that $WT1_{332-347}$ peptide specifically binds to HLA-DRB1*0405 among HLA-DRB1 molecules showing polymorphism, and induce the growth of $WT1_{332-347}$-specific CD4-positive cell line E04.1.

Example 7

Antigen Presentation of $WT1_{332-347}$ Peptide to HLA-DRB1*0405

Figure 7:
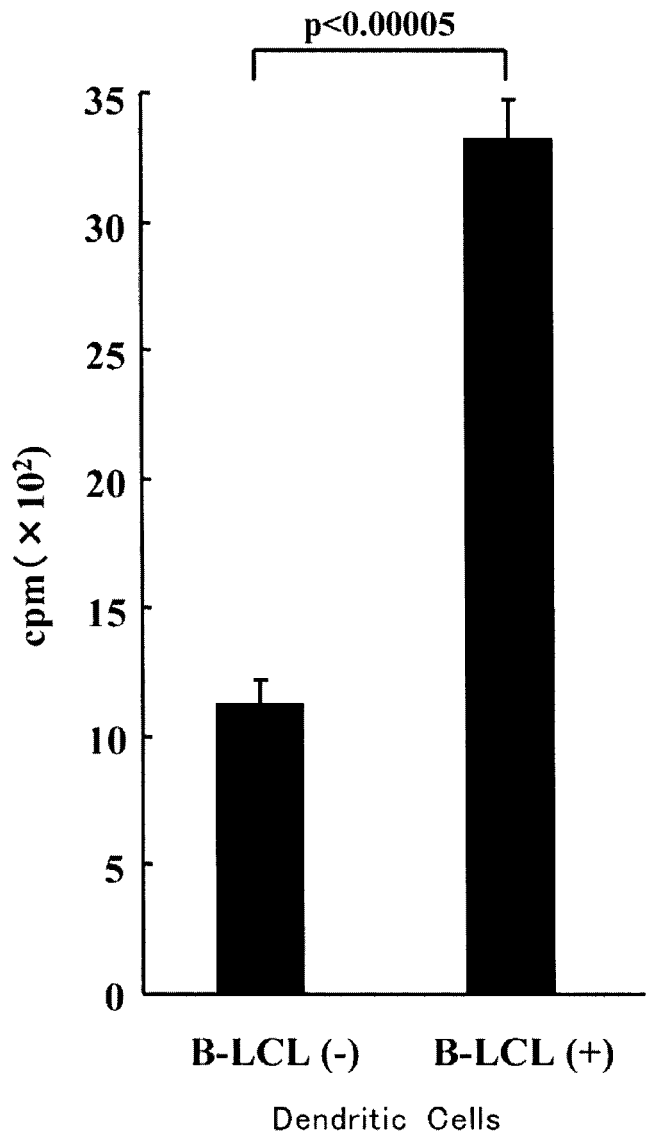
FIG. 7 shows the results of examination into responsiveness of E04.1 cell line to B-LCL(+) cells expressing WT1 gene. In the figure, "B-LCL(−)" represents the results obtained using B-LCL(−) cell not-expressing WT1 gene as stimulated cells, and "B-LCL(+)" the results obtained using B-LCL(+) cells expressing WT1 gene as stimulated cells. The vertical axis indicates the amount of [$^3$H]-thymidine uptake (cpm) by E04.1 cell lines.

B-LCL(−) cells (B-cell line) and B-LCL (+) cells (B-cell line expressing WT1), which were established from blood of an HLA-DRB1*0405-positive healthy volunteer as described in Example 3, were each subjected to X-ray irradiation and seeded in 96-well plate at $3 \times 10^4$ cells/well. E04.1 cells were seeded into each well at $1 \times 10^4$ cells and cocultured. Growth response of E04.1 cells was then measured in a manner similar to Example 4. The results are shown in FIG. 7. E04.1 cells showed proliferative response when cocultured with B-LCL (+) cells expressing WT1, but not when cocultured with B-LCL (−) cells not-expressing WT1.

Figure 8:
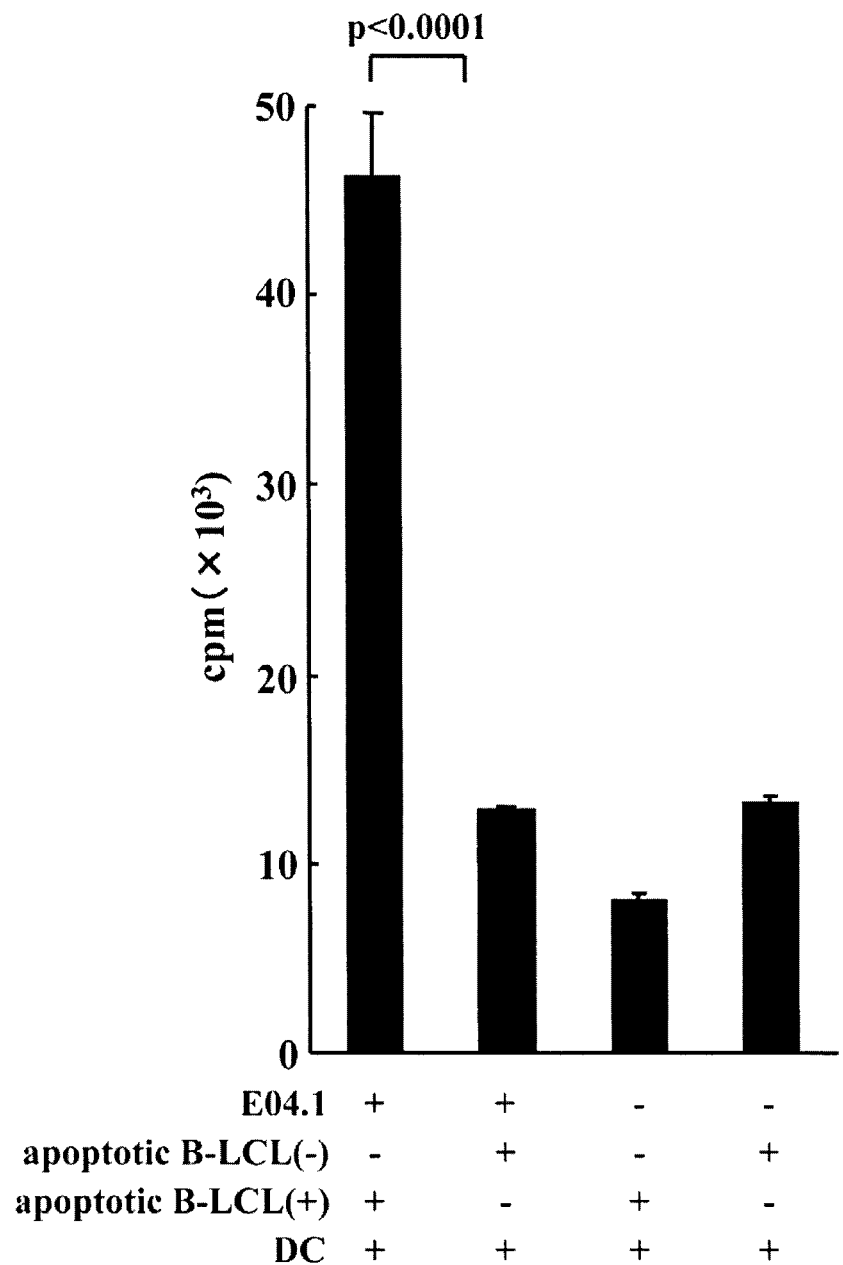
FIG. 8 shows the results of examination into responsiveness of E04.1 cell line to dendritic cells pulsed with B-LCL (+) cells in which apoptosis has been induced. In the figure, "apoptotic B-LCL (+)" represents the results obtained using dendritic cells pulsed with B-LCL(+) cells expressing WT1 gene and having been induced apoptosis, and "apoptotic B-LCL (−)" represents the results obtained using dendritic cells pulsed with B-LCL(−) cells not-expressing WT1 gene and having been induced apoptosis. Further, "E04.1+" represents the results obtained by cocultivation of E04.1 cells with dendritic cells, and "E04.1−" the results obtained by cocultivation without E04.1 cells. The vertical axis indicates the amount of [$^3$H]-thymidine uptake (cpm) by E04.1 cell lines.

Next, B-LCL(−) or B-LCL (+) cells ($1 \times 10^5$ cells each) having been induced apoptosis were cocultured for 16 hours with dendritic cells ($3 \times 10^4$ cells) prepared from blood of an HLA-DRB1*0405-positive healthy volunteer in a manner similar to Example 4, seeded in well of 96-well plate, and cocultured with E04.1 cells ($1 \times 10^4$ cells). Growth response of E04.1 cells was then measured in a manner similar to Example 1. The results are shown in FIG. 8. E04.1 cells showed proliferative response when cocultured with dendritic cells pulsed with apoptosis-induced B-LCL (+) cells, but did not when cocultured with dendritic cells pulsed with apoptosis-induced B-LCL (−) cells. These results indicate that $WT1_{332-347}$ peptide is first generated through the degradation of WT1 protein in B-LCL (+) cells, then presented to HLA-DRB1*0405 and induce proliferation of E04.1 cells.

Induction of apoptosis in B-LCL (−) and B-LCL (+) cells was conducted by osmotic shock. Namely, $1 \times 10^6$ cells were suspended in 500 µl of a hyperosmotic medium (RPMI medium containing 0.5 M sucrose, 10% w/v polyethylene glycol 1000 and 10 mM HEPES, pH 7.2), and left to stand at 37° C. for 10 minutes. The culture was then diluted by 30-times with a hypoosmotic medium (60% RPMI, 40% water) previously adjusted to 37° C., and left to stand at 37° C. for 2-3 minutes. Cells were collected by centrifuging at room temperature for 5 minutes and used as apoptosis-induced cells. Induction of apoptosis was confirmed by a fluorescent dye for staining dead cells (Propidium Iodide, and AnnexinV, i.e., a phosphatidyl serine-binding reagent).

Example 8

Activation of E04.1 Cells with $WT1_{332-347}$ Peptide

Figure 9:
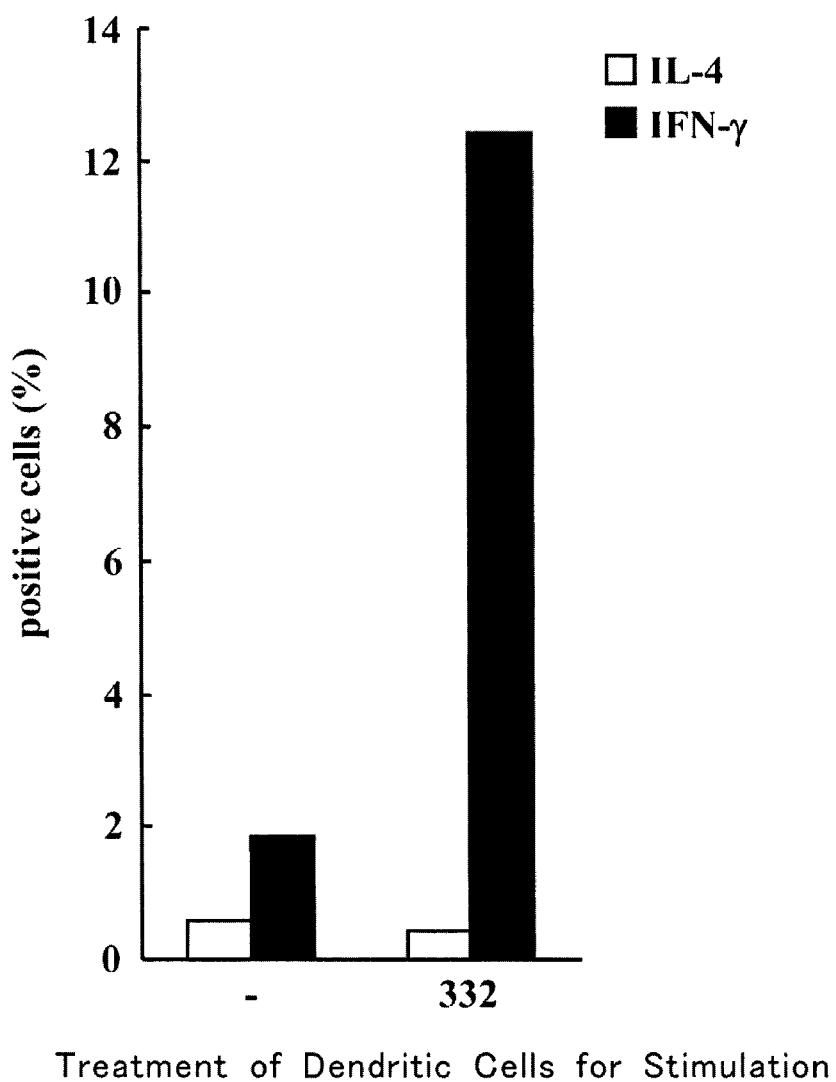
FIG. 9 shows the results of examination into cytokine production of E04.1 cell lines to dendritic cells pulsed with WT1-derived $WT1_{332-347}$ peptide. In the figure, "-" represents the results obtained using dendritic cells not pulsed with a peptide, and "332" the results obtained using dendritic cells pulsed with $WT1_{332-347}$ peptide. The vertical axis indicates the percentage (%) of E04.1 cells showing the production of IL-4 (blank bar) or IFN-γ (filled bar).

Dendritic cells prepared from blood of an HLA-DRB1*0405-positive healthy volunteer in a manner similar to Example 4 were pulsed with $WT1_{332-347}$ peptide, mixed with E04.1 cells, and cultured for 24 hours. As a negative control group, dendritic cells not pulsed with the peptide were mixed with E04.1 cells. After 24-hour-cultivation, Brefeldin A was added to a final concentration of 10 µg/ml to inhibit exocytosis of E04.1 cells. Further, CD4-positive T cells were recovered after culturing for another 6 hours, and fixed with PBC containing 2% formaldehyde, and treated by permeabilization solution containing 0.1% saponin to increase the cell membrane permeability of antibody. The treated cells were then intracellularly stained by treating with PE-labeled anti-IFN-γ antibody (BD PharMingen) and FITC-labeled anti-IL-4 antibody (BD PharMingen), and analyzed using a flow cytometer. The results are shown in FIG. 9. It was revealed that E04.1 cells, when cocultured with dendritic cells pulsed with $WT1_{332-347}$ peptide, were induced strongly to produce IFN-γ which is a Th-1-type cytokine, but not to produce IL-4 which is a Th-2-type cytokine.

Figure 10:
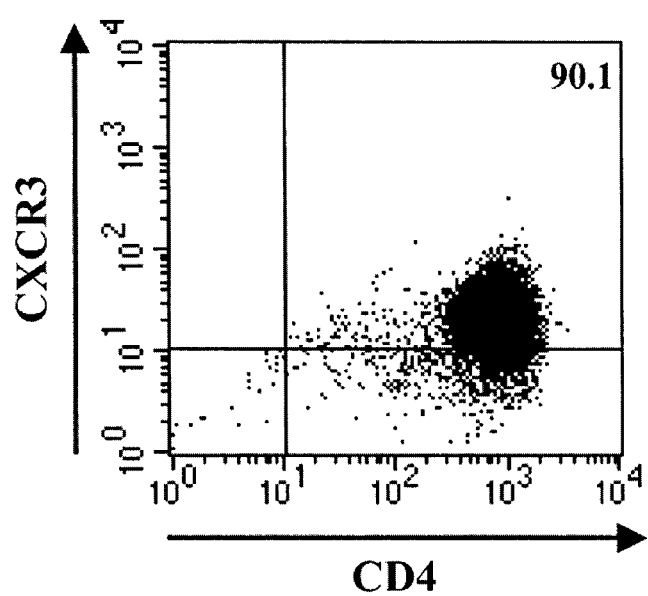
FIG. 10 shows the results of analysis of E04.1 cell line stained with anti-CD4 antibody and anti-CXCR3 antibody by flow cytometer. In the figure, the horizontal and vertical axes indicate cells positive for CD4 and for CXCR3, respectively. The percentage of cells positive for both CD4 and CXCR3 was 90.1%.
Figure 11A:
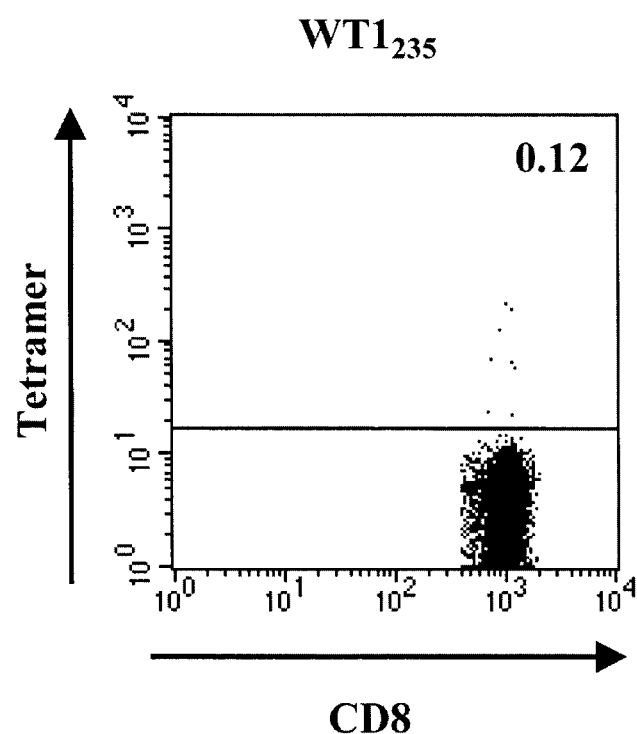
FIG. 11 shows the results of examination into influence of WT1-derived $WT1_{332-347}$ peptide on the induction of WT1-specific CTLs. PBMCs originated in a healthy volunteer (HLA-A*2402/1101, DRB1*0405/0803) were cultured for 7 days under the stimulation conditions of (A) $WT1_{235-243}$ peptide (FIG. 11A), (B) $WT1_{235-243}$ peptide+$WT1_{332-347}$ peptide (FIG. 11B), (C) $WT1_{235-243}$ peptide+E04.1 cell (FIG. 11C) and (D) $WT1_{235-243}$ peptide+$WT1_{332-347}$ peptide+E04.1 cell (FIG. 11D). Then, one half of the recovered cells were analyzed with flow cytometer to obtain the percentage of $WT1_{235-243}$-specific CTL precursors. The horizontal and vertical axes indicate the percentage of cells positive for CD8 and for $WT1_{235-243}$ peptide/HLA-A*2402, respectively.
Figure 11B:
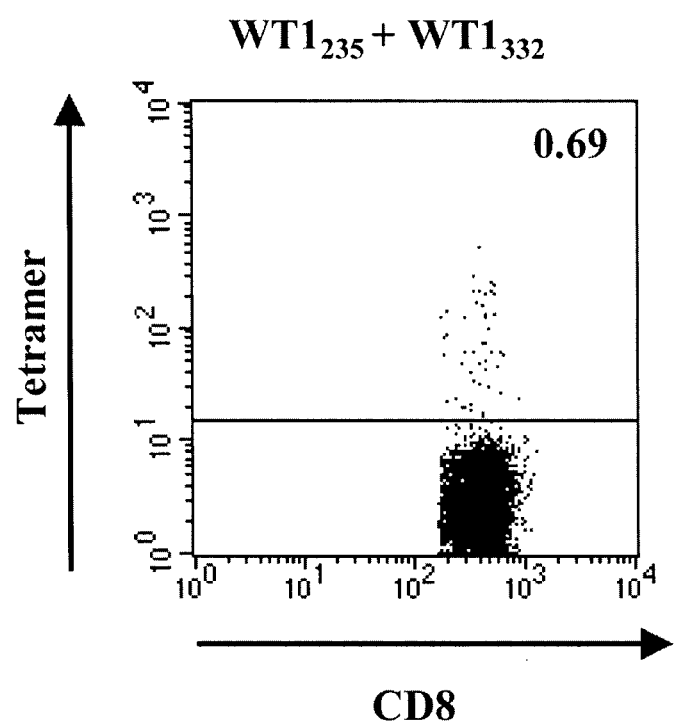
Figure 11C:
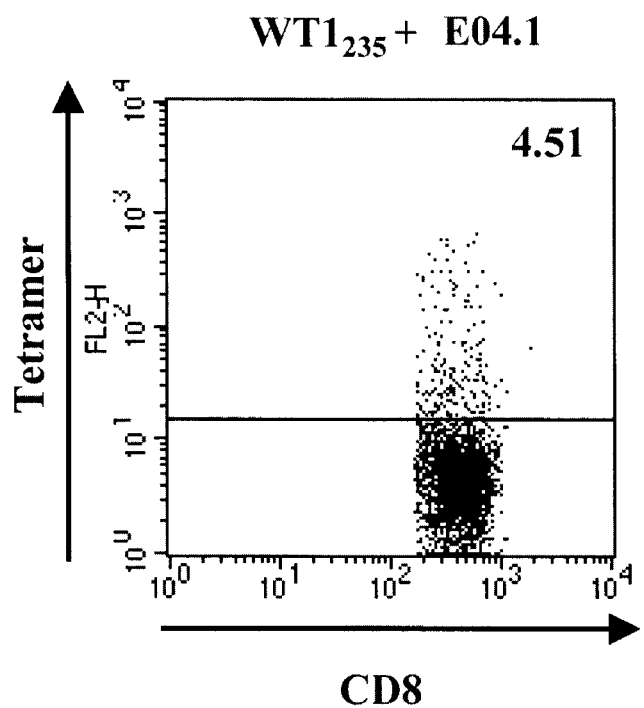
Figure 11D:
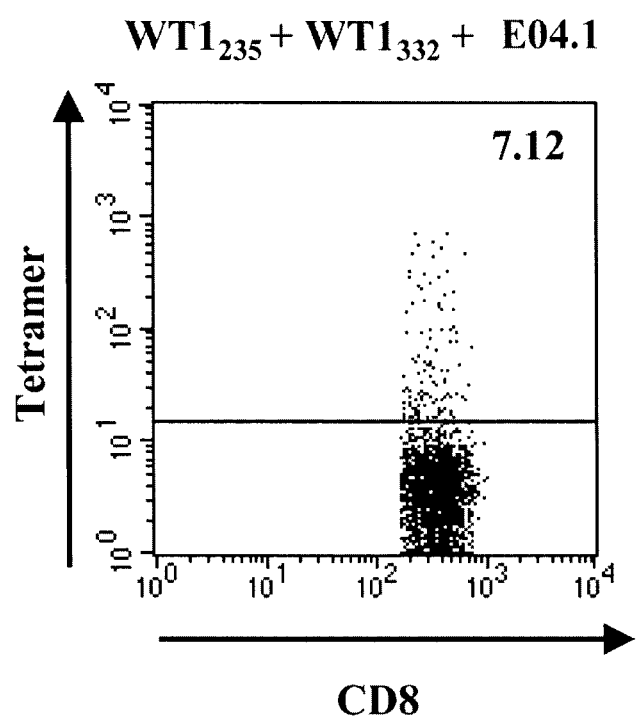
Figure 12A:
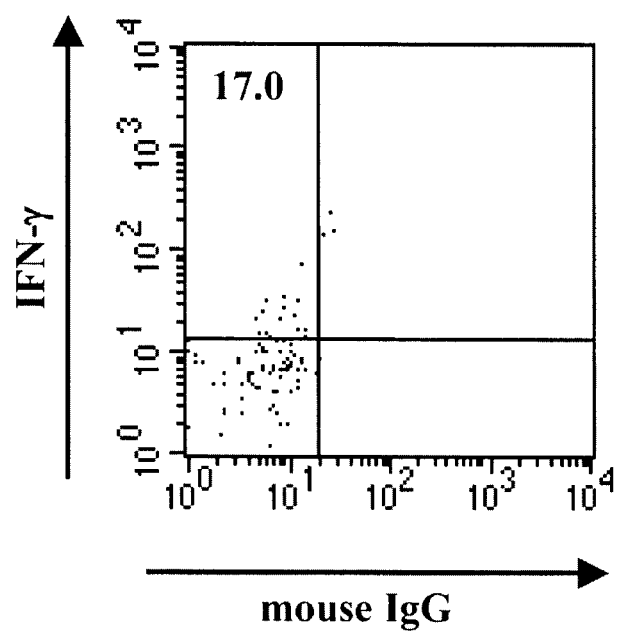
FIG. 12 shows the results of examination into influence of WT1-derived $WT1_{332-347}$ peptide on the activation of WT1-specific CTLs. Another half of the cells recovered in the experiment mentioned in FIG. 11 were stimulated with $WT1_{235-243}$ peptide for 6 hours, and intracellular IFN-γ was stained. The vertical and horizontal axes indicate the cells positive for intracellular IFN-γ and for anti-mouse IgG antibody, respectively. The figure shows the results of stimulation with (A) $WT1_{235-243}$ peptide (FIG. 12A), (B) $WT1_{235-243}$ peptide+$WT1_{332-347}$ peptide (FIG. 12B), (C)) $WT1_{235-243}$ peptide+E04.1 cell (FIG. 12C), and (D) $WT1_{235-243}$ peptide+$WT1_{332-347}$ peptide+E04.1 cell (FIG. 12D).
Figure 12B:
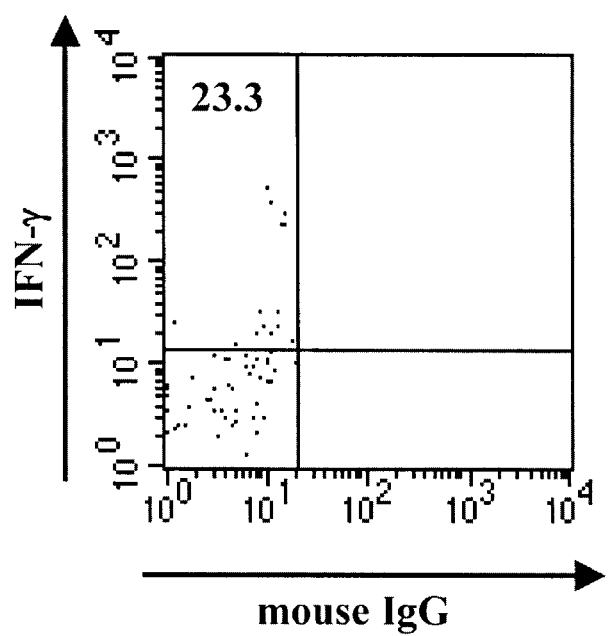
Figure 12C:
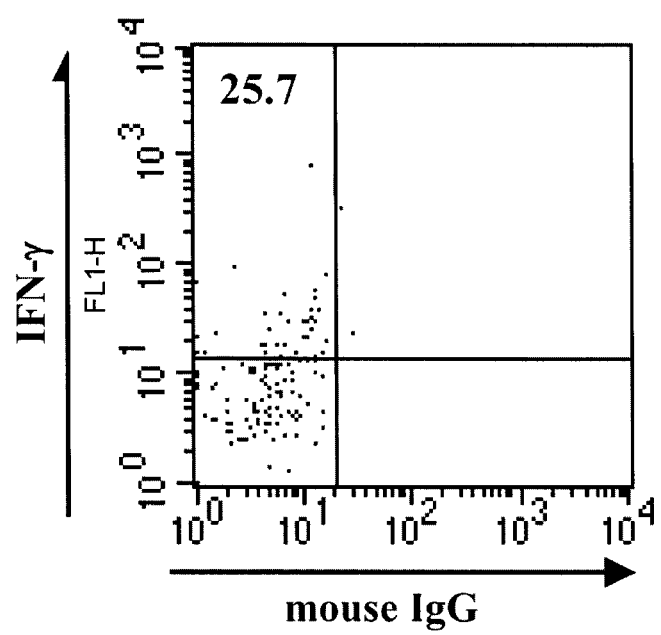
Figure 12D:
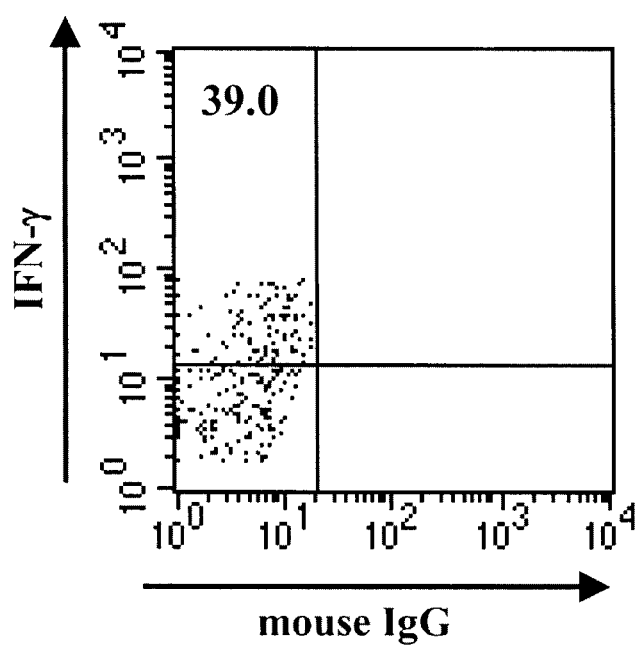

Unstimulated E04.1 cells were stained by treating with anti-CD4 antibody and anti-CXCR3 antibody, and analyzed by flow cytometer. The results are shown in FIG. 10. It was revealed that more than 90% of E04.1 cells are CD4-positive T cells of Th-1 type which are positive for CD4 and CXCR3. CXCR3 is known to be a chemokine receptor highly expressed on Th-1 type immunocytes.

The above results indicate that $WT1_{332-347}$ peptide activate E04.1 cells, $WT1_{332-347}$-specific CD4-positive cell line, and induce the cells to produce IFN-γ which is a Th-1 type cytokine. These results demonstrate that $WT1_{332-347}$ peptide activates and makes CD4-positive T cells differentiate into Th-1 type.

Example 9

Enhancement of Induction and Activation of WT1-Specific CTLs by $WT1_{332-347}$ Peptide PBMCs were prepared using blood of the same healthy volunteer (HLA-A*2402/1101, DRB1*0405/0803) as that used for establishment of E04.1 cells in a manner similar to Example 4, and seeded in 24-well culture plate at $3 \times 10^4$ cells/well. To the well were added $WT1_{235-243}$ peptide (SEQ ID NO: 27) and E04.1 cells in the following manners, and the plate was cultured at 37° C. for 7 days. $WT1_{235-243}$ peptide (20 µg/ml); $WT1_{235-243}$ peptide (20 µg/ml)+$WT1_{332-347}$ peptide (20 µg/ml); $WT1_{235-243}$ peptide (20 µg/ml)+E04.1 cells ($1.5 \times 10^6$ cells/well); or $WT1_{235-243}$ peptide (20 µg/ml)+$WT1_{332-347}$ peptide (20 µg/ml)+E04.1 cells ($1.5 \times 10^6$ cells/well). As medium, X-VIVO 15™ medium containing 10% AB serum was used. $WT1_{235-243}$ peptide used here is a cancer antigen peptide having activity of inducing HLA-A'2402-restricted CTLs (WO2004/024175).

After 7-day-cultivation, cells were recovered and one half of the cells were stained using anti-CD8 antibody (BD PharMingen) and $WT1_{235-243}$ peptide/HLA-A*2402-specific PE-labeled tetramer, and analyzed by flow cytometer. The results are shown in FIG. 11 (A-D). It has been reported that stimulation of PBMCs with $WT1_{235-243}$ peptide leads to induction of $WT1_{235-243}$ peptide-specific CTL precursors positive for both CD8 and $WT1_{235-243}$ peptide/HLA-A*2402 (Cancer Immunol Immunother, 51, p 614-620 (2002)). When PBMCs were stimulated with $WT1_{235-243}$ peptide alone, the percentage of WT1$_{235-243}$ peptide-specific CTL precursors was 0.12% (FIG. 11-A). When stimulation was conducted using WT1$_{235-243}$ peptide plus WT1$_{332-347}$ peptide, the percentage of WT1$_{235-243}$ peptide-specific CTL precursors increased to 0.69% (FIG. 11-B). When stimulation was conducted using WT1$_{235-243}$ peptide plus E04.1 cells, the percentage of WT1$_{235-243}$ peptide-specific CTL precursors further increased to 4.51% (FIG. 11-C). When stimulation was conducted using WT1$_{235-243}$ peptide plus WT1$_{332-347}$ peptide plus E04.1 cells, the percentage of WT1$_{235-243}$ peptide-specific CTL precursors still further increased to 7.12% (FIG. 11-D).

Another half of the recovered cells (3×10$^5$ cells) were cocultured for 6 hours with dendritic cells pulsed with WT1$_{235-243}$ peptide and undergone X-ray irradiation (30 Gy). One hour after the initiation of cultivation, Brefeldin A was added to inhibit exocytosis of cells. Cultivation was continued for another 5 hours and the cells were stained with anti-CD8 antibody and WT1$_{235-243}$ peptide/HLA-A*2402-specific PE-labeled tetramer. The cells were fixed and treated with a permeabilization solution to increase cell membrane permeability, and intracellularly stained by PE-labeled anti-IFN-γ antibody in a manner similar to Example 8. As a negative control group, cells were stained with APC-labeled anti-mouse IgG antibody (BD PharMingen), and cell populations positive for both IFN-γ and mouse IgG were excluded as non-specific staining.

The results are shown in FIG. 12 (A-D). When WT1$_{235-243}$ peptide-specific CTL precursors are stimulated with WT1$_{235-243}$ peptide for 6 hours, CTLs which are specific for activated WT1$_{235-243}$ peptide and are positive for CD8, WT1$_{235-243}$ peptide/HLA-A*2402 and IFN-γ are induced. When stimulation was conducted using WT1$_{235-243}$ peptide alone, the percentage of CTLs specific for activated WT1$_{235-243}$ peptide was 17.0% (FIG. 12-A). When stimulation was conducted using WT1$_{235-243}$ peptide plus WT1$_{332-347}$ peptide, the percentage of CTLs specific for activated WT1$_{235-243}$ peptide was increased to 23.3% (FIG. 12-B). When stimulation was conducted using WT1$_{235-243}$ peptide plus E04.1 cells, the percentage of CTLs specific for activated WT1$_{235-243}$ peptide was increased to 25.7% (FIG. 12-C). When stimulation was conducted using WT1$_{235-243}$ peptide plus WT1$_{332-347}$ peptide plus E04.1 cells, the percentage of CTLs specific for activated WT1$_{235-243}$ peptide was increased to 39.0% (FIG. 12-D).

From the above results, it was revealed that WT1$_{332-347}$ peptide is a helper peptide which enhances the induction and activation of WT1-specific CTL precursors. It was also revealed that E04.1 cell is a helper T cell which enhances the activation of WT1-specific CTLs and that its helper function is increased by WT1$_{332-347}$ peptide and the activation of WT1-specific CTLs is enhanced.

Example 10

Investigation into Promiscuous Nature of WT1$_{332-347}$ Peptide

WT1$_{332-347}$ peptide was examined whether it also can bind to HLA-DRB1*1502 molecule, which is said that many Japanese possess, and induce WT1$_{332-347}$-specific CD4-positive T cells as a promiscuous helper peptide.

1. Experimental Method

1) Preparation of Dendritic Cells (DC)
Peripheral blood mononuclear cells (PBMCs) were isolated from peripheral blood of a healthy volunteer (HLA-DRB1*1502/1403), and seeded in 6-well plastic plate using 1% AB-type serum (Nabi, Miami, Fla.) and X-VIVO15™ medium (Cambrex) at 1×10$^7$ cells/well, and cultured for 2 hours. After removing non-adherent cells, the remaining adherent cells were cultured in a medium containing 1000 IU/ml IL-4(PeproTech), 1000 IU/ml GM-CSF (PeproTech), 1% AB-type serum, and X-VIVO 15™ medium. On days 2 and 4, medium was changed and IL-4 and GM-CSF were added, and on day 6, TNF-α was added up to 100 IU/ml to make dendritic cells mature.

2) Induction of WT1$_{332-347}$-Specific CD4-Positive T Cells
CD4-positive T cells were isolated from blood of the same volunteer using RosetteSep (StemCell) for separating CD4-positive T cells. The resulting CD4-positive T cells were seeded in 24-well plate at 3×10$^6$ cells/well, and stimulated with autologous dendritic cells (3×10$^5$ cells) pulsed with WT1$_{332-347}$ peptide (20 µg/ml) and undergone radiation irradiation (25 Gy). On the next day from stimulation, IL-2 was added up to 20 IU/ml. In a similar manner, the stimulated CD4-positive T cells were stimulated every one week with dendritic cells pulsed with WT1$_{332-347}$ peptide (20 µg/ml). Further, medium change was conducted using IL-2-containing medium on every other day following the second stimulation. In the experiments, CD4-positive T cells induced by 3 times of stimulation in total.

3) Growth Assay
Growth assay was conducted by [$^3$H]-thymidine incorporation method. CD4-positive T cells induced by stimulation with a peptide (3×10$^4$ cells; responder) were cocultured with PBMCs pulsed with a peptide selected from WT1$_{332-347}$, WT1$_{172-186}$ and WT1$_{225-243}$ peptides and undergone radiation irradiation (1×10$^5$ cells, "stimulator") in a 96-well plate. As a negative control, DC(−) not pulsed with a peptide was used. After 80-hour-cocultivation, [$^3$H]-thymidine (Amersham Biosciences) was added at 37 kBq/well. The plate was incubated for another 16 hours and measured with β scintillation counter. Measurement unit is "count per minute (cpm)", and every assay was carried out in triplicate.

4) Analysis of Cytokine Production by Flow Cytometry
In the same manner as growth assay, CD4-positive T cells were cocultured with stimulators for 2 hours, and thereto was added Brefeldin A. Four hours later, cells were recovered, subjected to treatment for fixation and permeation, stained with FITC-labeled anti-IL-4 antibody (BD Pharmingen) and PE-labeled anti-IFN-γ antibody (BD Pharmingen), and analyzed by flow cytometry.

5) ELISA Assay
PBMCs (6×10$^5$ cells) pulsed or not pulsed with WT1$_{332-347}$ peptide were treated by radiation irradiation (25 Gy), and each group of cells was cocultured with WT1$_{332-347}$-induced CD4-positive T cells (6×10$^5$ cells). After 72-hour-cultivation, the supernatant was recovered, and 300 µl of the solution was used for measurement of IL-4 and IFN-γ.

6) TCR Repertoire Assay
Repertoire of β chain of T-cell receptor (TCR) for CD4-positive T cells induced by WT1$_{332-347}$ peptide was analyzed using TCR Vβ repertoire Kit (BECKMAN COULTER), FACsort (BECTON DICKINSON).

2. Experimental Results

Figure 13:
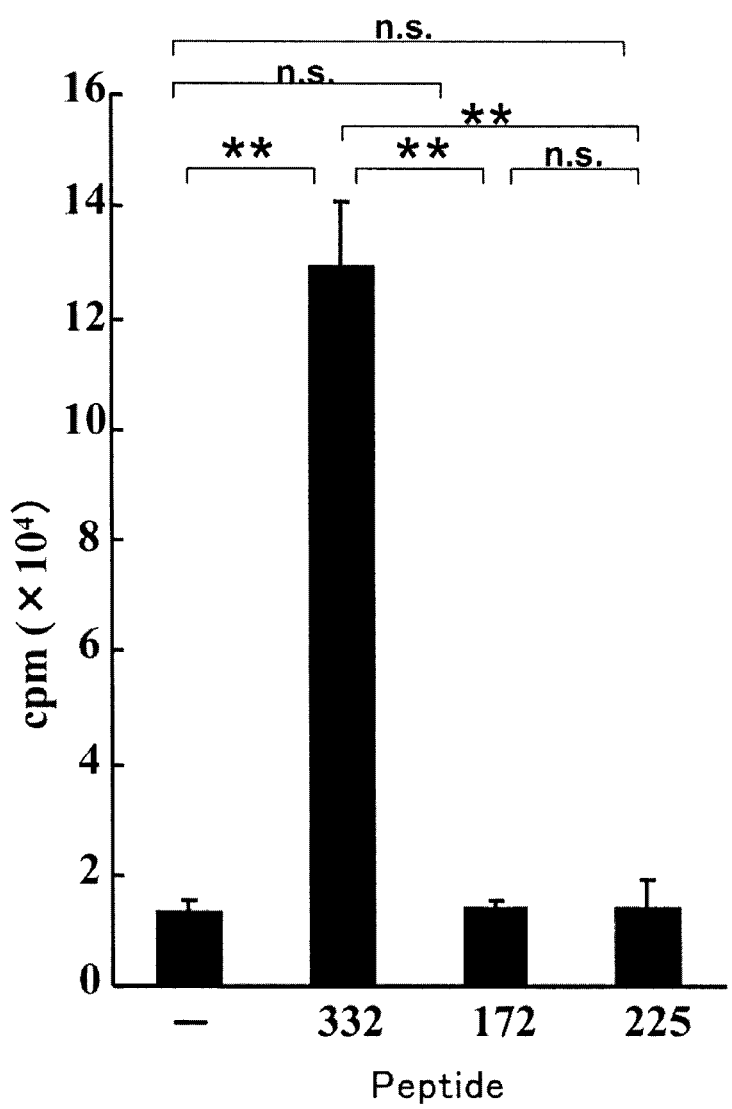
FIG. 13 shows the results of examination into responsiveness of CD4-positive T cells stimulated with WT1-derived $WT1_{332-347}$ peptide with various dendritic cells. In the figure, "-" represents the responsiveness with dendritic cells not pulsed with a peptide, "332" the responsiveness with dendritic cells pulsed with $WT1_{332-347}$ peptide, "172" the responsiveness with dendritic cells pulsed with $WT1_{172-186}$ peptide, and "225" the responsiveness with dendritic cells pulsed with $WT1_{225-243}$ peptide. The vertical axis indicates the amount of [$^3$H]-thymidine uptake (cpm) by CD4-positive T cells. The symbol "**" and "n.s." mean that the difference in the test groups is statistically significant or is not, respectively.

CD4-positive T cells isolated from blood of an healthy volunteer (HLA-DRB1*1502/1403) were stimulated three times in total with autologous dendritic cells pulsed with WT1$_{332-347}$ peptide. The so induced CD4-positive T cells were examined for the peptide specificity by growth assay using each of WT1$_{172-186}$, WT1$_{225-243}$ and WT1$_{332-347}$ peptides. As a result, CD4-positive T cells induced by WT1$_{332-347}$ peptide did not proliferate in the absence of the peptide or under the stimulation with WT1$_{172-186}$ or WT1$_{225-243}$, but proliferated to become about 10-times as much when stimulated with WT1$_{332-347}$ (FIG. 13). From these results, the induced CD4-positive T cells have specificity for WT1$_{332-347}$.

Figure 14A:
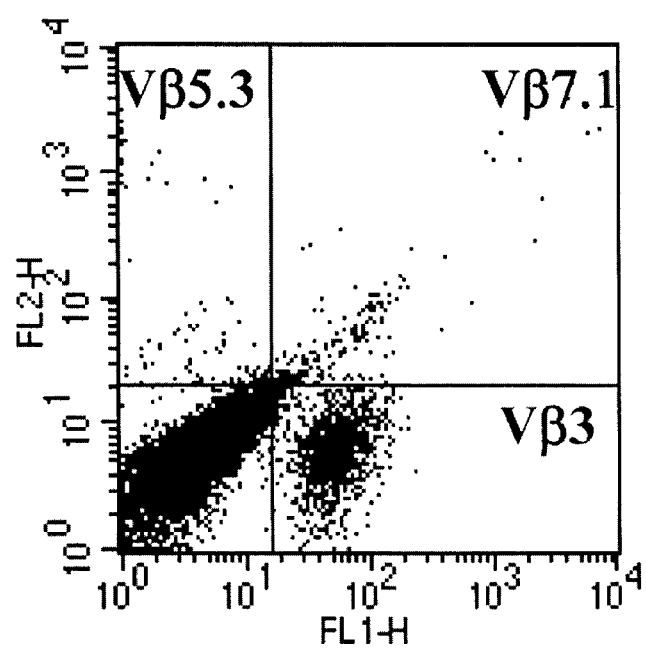
In FIG. 14A, the cell population in the lower right portion of quartered area represents Vβ3-positive cells. In panel FIG. 14B, the cell population in the lower right portion of quartered area represents Vβ20-positive cells.
Figure 14B:
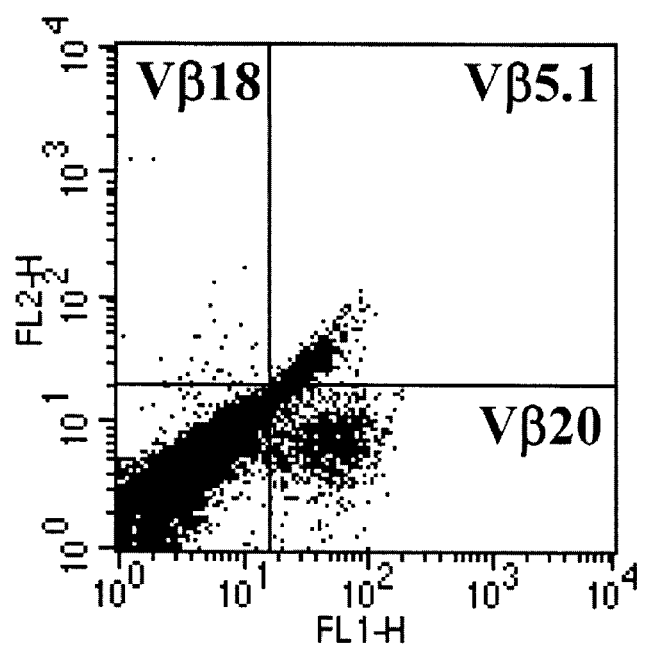
FIG. 14 shows the results of T-cell repertoire analysis of CD4-positive T cells stimulated with WT1-derived $WT1_{332-347}$ peptide. The cells were stained with different antibodies specific for respective Vβ chains of TCR and analyzed by flow cytometry.

The WT1$_{332-347}$ peptide-induced CD4-positive T cells were subjected to TCR repertoire assay. The results are shown in FIG. 14. Cells having Vβ3 and those having Vβ20 were dominant and each accounted for 10% of the total.

Figure 15A:
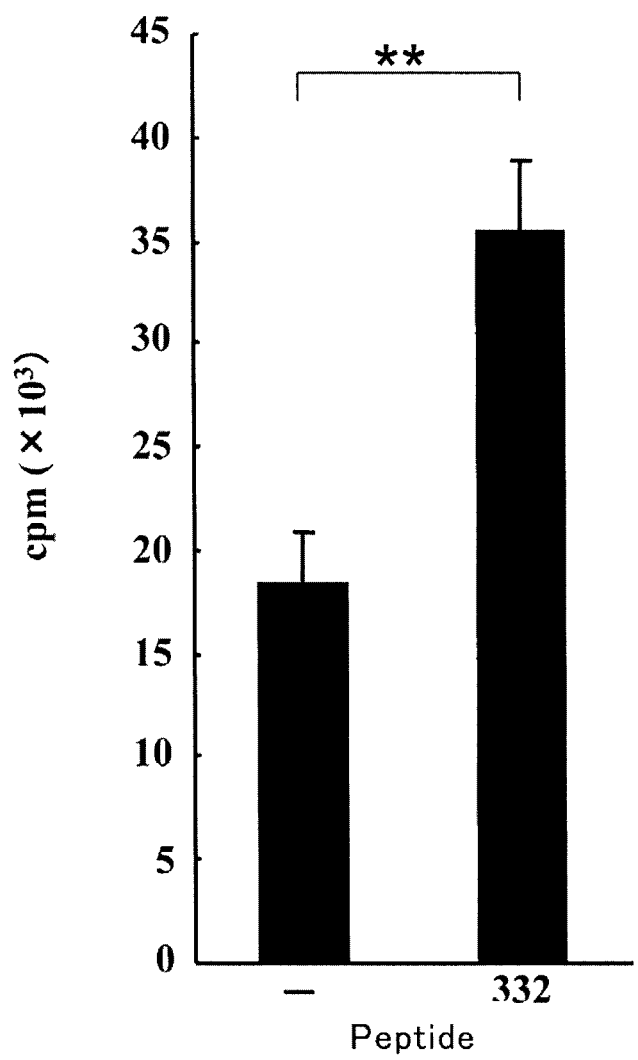
FIG. 15A and FIG. 15B show the results obtained using E15.1 cell line and E15.2 cell line, respectively. The symbol "**" means that the difference in the test groups is statistically significant.
Figure 15B:
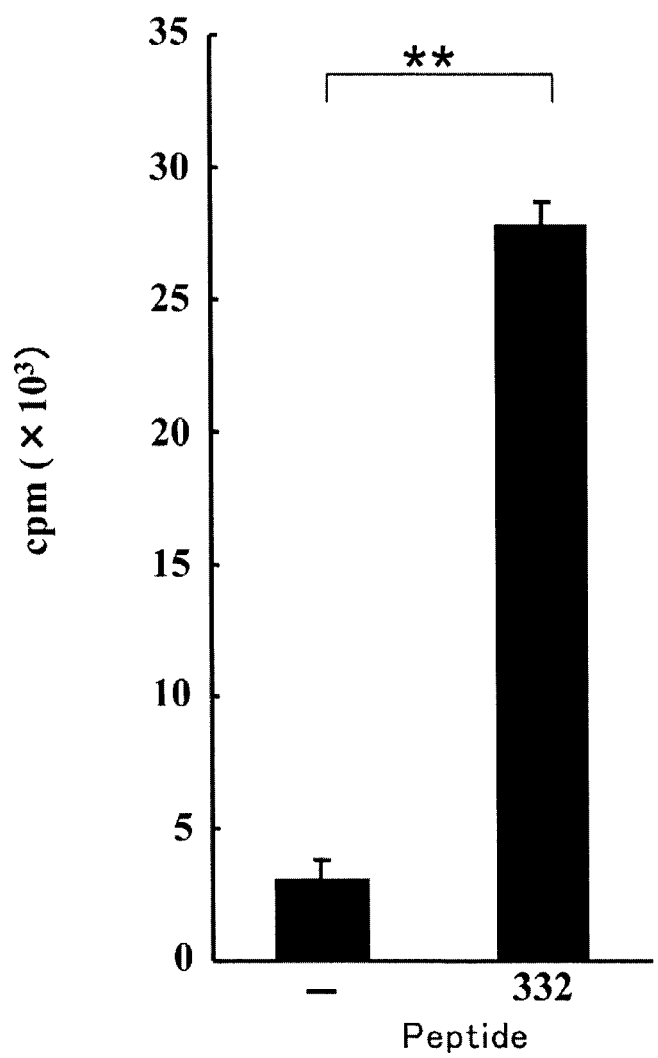

These dominant CD4-positive T cells were separated by sorting and the cell line having Vβ3 was named as E15.1 subline, while the one having Vβ20 as E15.2 subline. Of these two cell lines, E15.2 subline showed higher responsiveness to WT1$_{332-347}$ peptide (FIG. 15).

Figure 16:
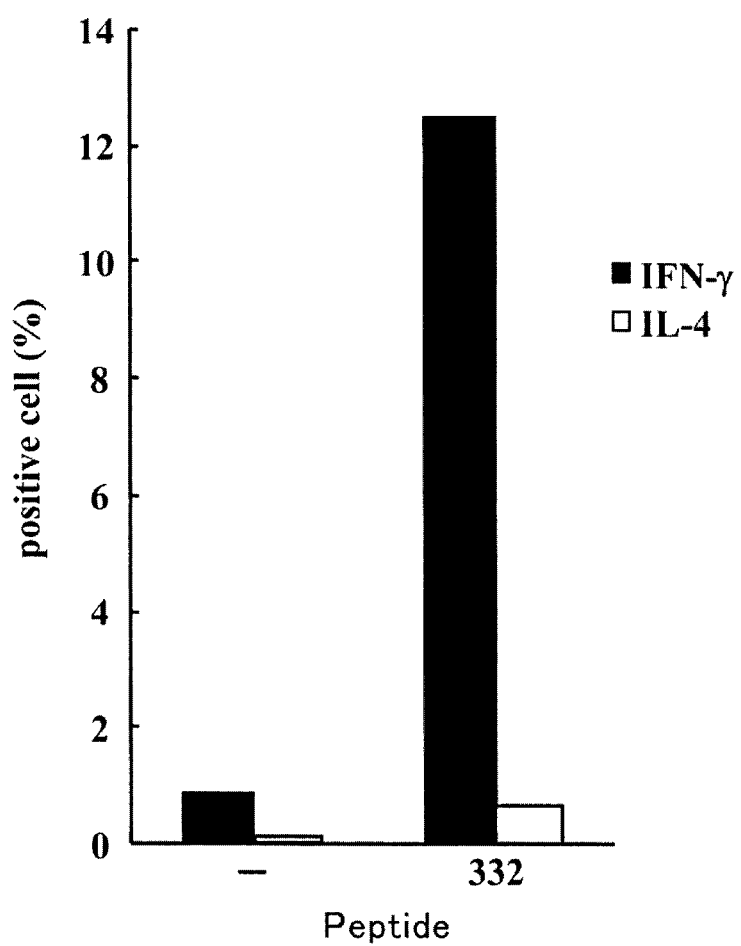
FIG. 16 shows the results of examination into cytokine production of E15.2 cell line to autologous PBMCs pulsed with WT1-derived WT1$_{332-347}$ peptide. In the figure, "-" represents the results obtained using dendritic cells not pulsed with a peptide, and "332" the results obtained using autologous PBMCs pulsed with WT1$_{332-347}$ peptide. The vertical axis indicates the percentage (%) of E15.2 cells showing the production of IL-4 (blank bar) or IFN-γ (filled bar).
Figure 17:
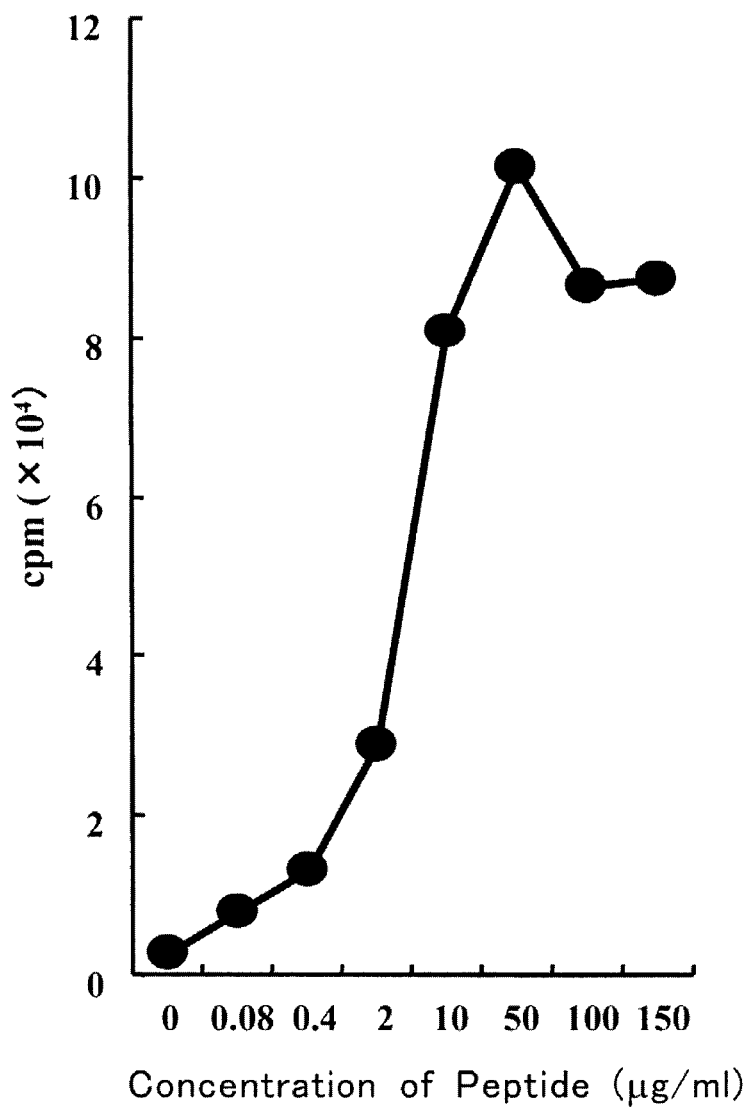
FIG. 17 shows the results of examination into the relation between the concentration of WT1-derived WT1$_{332-347}$ peptide pulsed into autologous PBMCs and the responsiveness of E15.2 cell line. The vertical axis indicates the amount of [$^3$H]-thymidine uptake (cpm) by E15.1 cell lines. The horizontal axis indicates the concentration of WT1$_{332-347}$ peptide pulsed into autologous PBMC.

E15.2 subline was then stimulated with WT1$_{332-347}$ peptide, and the secreted IL-4 and IFN-γ were measured by Intracellular stain method. As a result, it was revealed that IFN-γ (Th-1-type cytokine) and not IL-4 (Th-2-type cytokine) is dominantly produced by said cell line (FIG. 16). It was also revealed that the WT1$_{332-347}$-specific proliferative-response of E15.2 subline depends on the concentration of WT1$_{332-347}$ (FIG. 17). These results indicated that E15.2 subline is a Th-1-type CD4-positive T cell line specific for WT1$_{332-347}$.

As mentioned above, it was possible to induce Th-1-type CD4-positive T cell lines specific for WT1$_{332-347}$ from CD4-positive T cells derived from a healthy volunteer who is positive for HLA-DRB1*1502 molecule but negative for HLA-DRB1*0405 molecule. Based on these results, it is considered that said CD4-positive T cells participate in cellular immunity and can activate CTLs through the secretion of cytokines. Thus, it was shown that antitumor effects can be further enhanced by using WT1$_{332-347}$ in combination with HLA-class I-restricted WT1 peptide (cancer antigen peptide) capable of activating CTLs.

Figure 18A:
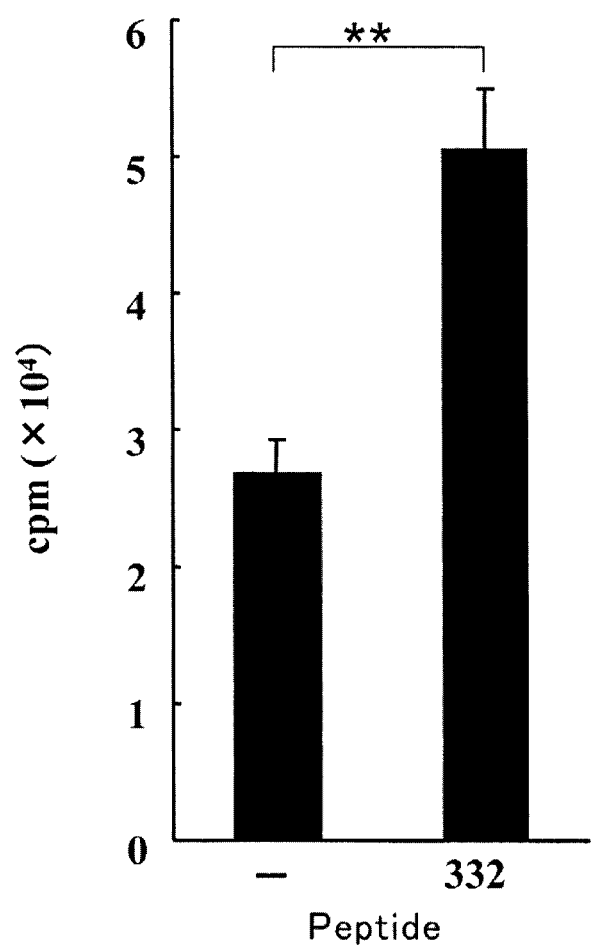
FIG. 18A shows the results obtained using PBMCs from an HLA-DRB1*1502-positive healthy volunteer and FIG. 18B the results obtained using PBMCs from an HLA-DRB1*1502-negative healthy volunteer. The vertical axis indicates the amount of [$^3$H]-thymidine uptake (cpm) by E15.2 cell lines. The symbol "**" and "n.s." mean that the difference in the test groups is statistically significant or not, respectively.
Figure 18B:
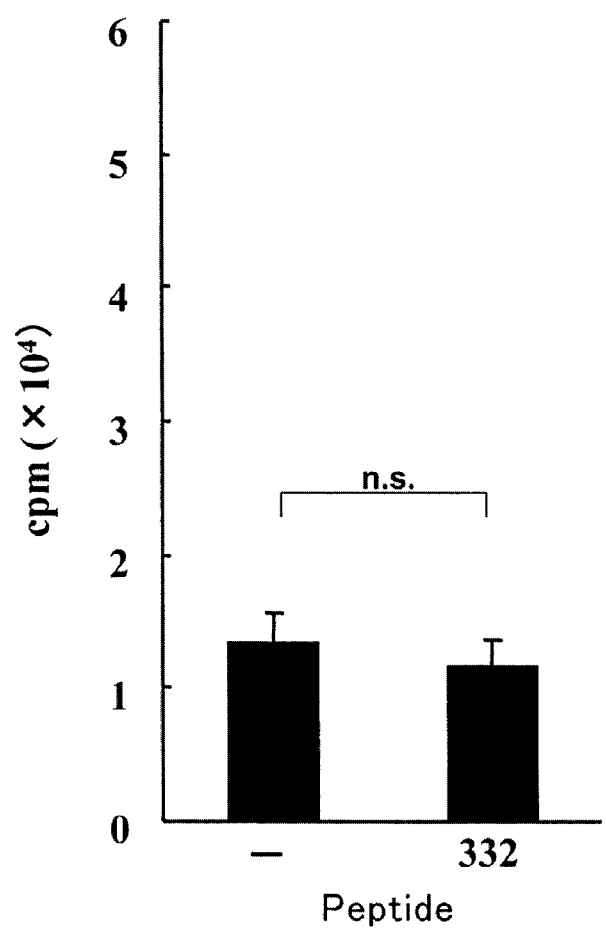
FIG. 18 shows the results of examination into responsiveness of E15.2 cell line to PBMCs positive or negative for HLA-DRB1*1502 pulsed with WT1-derived WT1$_{332-347}$ peptide. In the figure, "-" represents the results obtained by using PBMCs not pulsed with the WT1$_{332-347}$ peptide, and "332" the results obtained using PBMCs pulsed with the peptide.

PBMCs derived from an HLA-DRB1*1502-positive healthy volunteer (1502/0901) or an HLA-DRB1*1502-negative healthy volunteer (1302/0803) were pulsed with WT1$_{332-347}$ peptide to obtain stimulators. Each of stimulators was cocultured with E15.2 subline, and analyzed for WT1$_{332-347}$-specific proliferation by growth assay. The results are shown in FIG. 18. In an HLA-DRB1*1502-positive healthy volunteer, WT1$_{332-347}$-specific proliferation was observed but in an HLA-DRB1*1502-negative healthy volunteer, no proliferation was observed (FIG. 18). This indicated that the WT1$_{332-347}$-specific proliferation of E15.2 subline is restricted to HLA-DRB1*1502.

As described above, analysis conducted using E15.2 subline which is a Th-1-type CD4-positive T cell line specific for WT1$_{332-347}$ peptide demonstrated that WT1$_{332-347}$ is a promiscuous helper peptide which binds not only to HLA-DRB1*0405 molecule but also to HLA-DRB1*1502 molecule which molecules are found in the first and the third frequencies, respectively, among Japanese.

INDUSTRIAL APPLICABILITY OF THE INVENTION

The present invention provides a WT1-derived HLA-DRB1*0405-binding antigen peptide, a polynucleotide encoding said peptide, a helper T cell inducer comprising said peptide or polynucleotide, and the like. The helper T cell inducer of the present invention is useful as an enhancer of cancer vaccine efficacy. The enhancer of cancer vaccine efficacy of the present invention is applicable to many cancer patients positive for HLA-DRB1*0405, and particularly useful as an enhancer of WT1 vaccine efficacy.

The invention claimed is:

1. A method of treating WT1- and HLA-DRB1*0405-expressing cancer or a WT1- and HLA-DRB1*1502-expressing cancer in an HLA-DRB1*0405- or an HLA-DRB1*1502-positive subject, which comprises administering a peptide consisting of the amino acid sequence of SEQ ID NO: 24, an expression vector comprising a polynucleotide encoding a peptide consisting of the amino acid sequence of SEQ ID NO: 24 or a cell comprising an expression vector comprising a polynucleotide encoding a peptide consisting of the amino acid sequence of SEQ ID NO: 24 to a subject in need thereof.

2. The method of claim 1, wherein said WT1-expressing cancer is a blood cancer selected from the group consisting of leukemia, myelodysplastic syndrome, multiple myeloma, and malignant lymphoma.

3. The method of claim 1, wherein said WT1-expressing cancer is a solid cancer selected from the group consisting of gastric cancer, colon cancer, lung cancer, breast cancer, embryonal cancer, hepatic cancer, skin cancer, bladder cancer, prostate cancer, uterine cancer, cervical cancer, and ovarian cancer.

4. The method of claim 1, wherein said administering is intradermally, subcutaneously, intramuscularly, or intravenously.

5. A method of treating WT1- and HLA-DRB1*0405-expressing cancer or a WT1- and HLA-DRB1*1502-expressing cancer in an HLA-DRB1*0405- or an HLA-DRB1*1502-positive subject, which comprises administering a peptide consisting of 16-25 contiguous amino acids in the amino acid sequence of human WT1 of SEQ ID NO: 1 to a subject in need thereof, wherein said peptide comprises the amino acid sequence of SEQ ID NO: 24.

6. The method of claim 5, wherein said WT1-expressing cancer is a blood cancer selected from the group consisting of leukemia, myelodysplastic syndrome, multiple myeloma, and malignant lymphoma.

7. The method of claim 5, wherein said WT1-expressing cancer is a solid cancer selected from the group consisting of gastric cancer, colon cancer, lung cancer, breast cancer, embryonal cancer, hepatic cancer, skin cancer, bladder cancer, prostate cancer, uterine cancer, cervical cancer, and ovarian cancer.

8. The method of claim 5, wherein said administering is intradermally, subcutaneously, intramuscularly, or intravenously.

9. The method of claim 5, wherein said peptide consists of the amino acid sequence of SEQ ID NO: 24.

10. The method of claim 1, wherein said method is a method of treating WT1- and HLA-DRB1*0405-expressing cancer in an HLA-DRB1*0405-positive subject.

11. The method of claim 1, wherein said method is a method of treating WT1- and HLA-DRB1*1502-expressing cancer in an HLA-DRB1*1502-positive subject.

12. The method of claim 5, wherein said method is a method of treating WT1- and HLA-DRB1*0405-expressing cancer in an HLA-DRB1*0405-positive subject.

13. The method of claim 5, wherein said method is a method of treating WT1- and HLA-DRB1*1502-expressing cancer in an HLA-DRB1*1502-positive subject.

14. A method of treating WT1-expressing cancer in an HLA-DRB1*0405- or an HLA-DRB1*1502-positive subject, which comprises administering a peptide consisting of the amino acid sequence of SEQ ID NO: 24, an expression vector comprising a polynucleotide encoding a peptide consisting of the amino acid sequence of SEQ ID NO: 24 or a cell comprising an expression vector comprising a polynucleotide encoding a peptide consisting of the amino acid sequence of SEQ ID NO: 24, said peptide, expression vector or cell being administered in combination with an HLA-class I restricted WT1 peptide capable of activating CTLs to a subject in need thereof.

15. The method of claim 14, wherein said WT1-expressing cancer is a blood cancer selected from the group consisting of leukemia, myelodysplastic syndrome, multiple myeloma, and malignant lymphoma.

16. The method of claim 14, wherein said WT1-expressing cancer is a solid cancer selected from the group consisting of gastric cancer, colon cancer, lung cancer, breast cancer, embryonal cancer, hepatic cancer, skin cancer, bladder cancer, prostate cancer, uterine cancer, cervical cancer, and ovarian cancer.

17. The method of claim 14, wherein said administering is intradermally, subcutaneously, intramuscularly, or intravenously.

18. The method of claim 14, wherein said method is a method of treating WT1- and HLA-DRB1*0405-expressing cancer in an HLA-DRB1*0405-positive subject.

19. The method of claim 14, wherein said method is a method of treating WT1- and HLA-DRB1*1502-expressing cancer in an HLA-DRB1*1502-positive subject.

20. A method of treating WT1-expressing cancer in an HLA-DRB1*0405- or an HLA-DRB1*1502-positive subject, which comprises administering a peptide consisting of 16-25 contiguous amino acids in the amino acid sequence of human WT1 of SEQ ID NO: 1 to a subject in need thereof, wherein said peptide comprises the amino acid sequence of SEQ ID NO: 24, said peptide being administered in combination with an HLA-class I restricted WT1 peptide capable of activating CTLs to a subject in need thereof.

21. The method of claim 20, wherein said WT1-expressing cancer is a blood cancer selected from the group consisting of leukemia, myelodysplastic syndrome, multiple myeloma, and malignant lymphoma.

22. The method of claim 20, wherein said WT1-expressing cancer is a solid cancer selected from the group consisting of gastric cancer, colon cancer, lung cancer, breast cancer, embryonal cancer, hepatic cancer, skin cancer, bladder cancer, prostate cancer, uterine cancer, cervical cancer, and ovarian cancer.

23. The method of claim 20, wherein said administering is intradermally, subcutaneously, intravenously.

24. The method of claim 20, wherein said peptide consists of the amino acid sequence of SEQ ID NO: 24.

25. The method of claim 20, wherein said method is a method of treating WT1- and HLA-DRB1*0405-expressing cancer in an HLA-DRB1*0405-positive subject.

26. The method of claim 20, wherein said method is a method of treating WT1- and HLA-DRB1*1502-expressing cancer in an HLA-DRB1*1502-positive subject.

* * * * *

UNITED STATES PATENT AND TRADEMARK OFFICE
CERTIFICATE OF CORRECTION

PATENT NO. : 10,124,046 B2
APPLICATION NO. : 13/755185
DATED : November 13, 2018
INVENTOR(S) : Haruo Sugiyama Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 186 days.

Signed and Sealed this
Twenty-first Day of May, 2019

Andrei Iancu
*Director of the United States Patent and Trademark Office*